United States Patent
Hamamoto et al.

(10) Patent No.: US 8,980,912 B2
(45) Date of Patent: *Mar. 17, 2015

(54) CYCLIC AMINE COMPOUND AND ACARICIDE

(75) Inventors: Isami Hamamoto, Odawara (JP); Keiji Koizumi, Odawara (JP); Masahiro Kawaguchi, Odawara (JP); Hisashi Tanigawa, Odawara (JP); Takehiko Nakamura, Odawara (JP); Tomomi Kobayashi, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 79 days.

This patent is subject to a terminal disclaimer.

(21) Appl. No.: 13/261,398

(22) PCT Filed: Feb. 24, 2011

(86) PCT No.: PCT/JP2011/054173
§ 371 (c)(1),
(2), (4) Date: Oct. 24, 2012

(87) PCT Pub. No.: WO2011/105506
PCT Pub. Date: Sep. 1, 2011

(65) Prior Publication Data
US 2012/0309964 A1    Dec. 6, 2012

(30) Foreign Application Priority Data

Feb. 25, 2010  (JP) .................. 2010-039839
May 21, 2010  (JP) .................. 2010-117392
Oct. 4, 2010   (JP) .................. 2010-224844

(51) Int. Cl.
| | | |
|---|---|---|
| C07D 451/06 | (2006.01) | |
| A01N 43/90  | (2006.01) | |
| A01N 43/42  | (2006.01) | |
| A01N 43/54  | (2006.01) | |
| A01N 43/56  | (2006.01) | |
| A01N 43/58  | (2006.01) | |
| A01N 43/80  | (2006.01) | |
| A01N 43/88  | (2006.01) | |
| C07D 491/052| (2006.01) | |

(52) U.S. Cl.
CPC ............ *C07D 451/06* (2013.01); *A01N 43/42* (2013.01); *A01N 43/54* (2013.01); *A01N 43/56* (2013.01); *A01N 43/58* (2013.01); *A01N 43/80* (2013.01); *A01N 43/88* (2013.01); *A01N 43/90* (2013.01); *C07D 491/052* (2013.01)
USPC ........... 514/304; 546/124; 546/193; 546/194; 544/333

(58) Field of Classification Search
CPC .................. A01N 43/90; C07D 451/06
USPC ........... 514/304; 546/124, 193, 194; 544/333
See application file for complete search history.

(56) References Cited

U.S. PATENT DOCUMENTS

| | | | |
|---|---|---|---|
| 2,970,144 A *  | 1/1961  | Zirkle ........................ 544/47 |
| 4,808,645 A    | 2/1989  | Ravichandran et al. | |
| 5,187,166 A *  | 2/1993  | Kikuchi et al. .......... 514/249 |
| 5,216,156 A    | 6/1993  | Galbo et al. | |
| 5,286,865 A    | 2/1994  | Galbo et al. | |
| 5,840,654 A    | 11/1998 | Kleemann | |
| 8,349,923 B2 * | 1/2013  | Roth ......................... 524/98 |
| 2004/0014784 A1| 1/2004  | Jakobi et al. | |
| 2011/0212938 A1*| 9/2011 | Xia et al. ................ 514/210.18 |

FOREIGN PATENT DOCUMENTS

| | | |
|---|---|---|
| EP | 0 200 683 B1    | 4/1990  |
| EP | 0 456 519 B1    | 7/1994  |
| EP | 0 467 848 B1    | 1/1996  |
| EP | 1439169 A1      | 7/2004  |
| JP | 08-034784 A     | 2/1996  |
| JP | 08-508277 A     | 9/1996  |
| TW | 201127294 A     | 8/2011  |
| WO | WO 00/71536 A1  | 11/2000 |
| WO | WO 03/017764 A1 | 3/2003  |
| WO | WO 2005/095380 A1| 10/2005 |

(Continued)

OTHER PUBLICATIONS

Boehringer et al."Benzhydryl and . . . " CA54:39199 (2960).*
Klioze et al."Benzenesulfenamides . . . " CA93:46595 (1980).*
Shah et al."Preparation of bicyclci . . . " CA150:259964 (2009).*
Exhibit 1 p. 1-5 (2014).*

(Continued)

*Primary Examiner* — Celia Chang
(74) *Attorney, Agent, or Firm* — Foley & Lardner LLP

(57) ABSTRACT

The present invention provides a cyclic amine compound represented by formula (I) (in formula (I), $Cy^1$ and $Cy^2$ independently represent a C6-10 aryl group or a heterocyclyl group; $R^{1a}$ to $R^{5a}$ independently represent a hydrogen atom or an unsubstituted or substituted C1-6 alkyl group; $R^{10}$, $R^{11}$, $R^{20}$ and $R^{21}$ independently represent an unsubstituted or substituted C1-6 alkyl group, an unsubstituted or substituted C1-6 alkoxy group, a halogen atom or the like; m, n, p, and r each represent an integer of 0 to 5; and Y represents an oxygen atom or the like) or salt thereof, and an acaricide including the same.

(I)

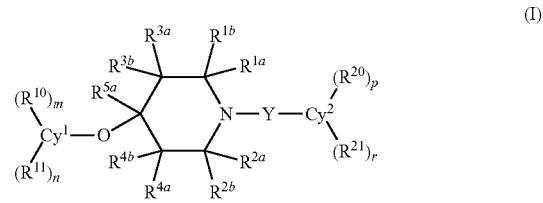

3 Claims, No Drawings

(56) References Cited

FOREIGN PATENT DOCUMENTS

| WO | WO 2007/022502 A2 | 2/2007 |
|----|-------------------|--------|
| WO | WO 2007/039563 A1 | 4/2007 |
| WO | WO 2007/040282 A1 | 4/2007 |
| WO | WO 2008/026658 A1 | 3/2008 |
| WO | WO 2008/101195 A2 | 8/2008 |
| WO | WO 2008/103613 A2 | 8/2008 |
| WO | WO 2008/126795 A1 | 10/2008 |
| WO | WO 2009/023180 A1 | 2/2009 |
| WO | WO 2009/028563 A1 | 3/2009 |
| WO | WO 2009/055331 A2 | 4/2009 |
| WO | WO 2011/078081 A1 | 6/2011 |

OTHER PUBLICATIONS

Improper Markus, Fed. Rg. v.76, p. 7162-7175, slide 1, 64067 (2011).*
Ellis et al., "The synthesis of functionalized chiral bicyclic lactam and lactone N-oxides using a tandem Cope elimination/reverse Cope elimination protocol," Tetrahedron Letters, 2007, 48:1683-1686.
Sosnovsky et al., "Preparation of 4-phosphorylated 1,4-dihydroxy-2,2,6,6-tetramethylpiperidines by reduction of nitroxyls with L-ascorbic acid," Synthesis, 1977, 9:619-622.
CAS RN 1049104-02-0, STN Entry Date Sep. 12, 2008.
CAS RN 770678-65-4, STN Entry Daet Oct. 27, 2004.
International Search Report dated Apr. 5, 2011 in PCT/JP2011/054173.
Office Action dated Dec. 26, 2012 in TW 100106336.
Office Action dated May 24, 2013 in AU 2011221128.
Sato et al., "Novel glycosylation of the nitroxyl radicals with peracetylated glycosyl fluorides using a combination of $BF_3 \cdot OEt_2$ and an amine base as promoters," Carbohydrate Research, 2001, 334:215-222.
International Search Report dated Feb. 22, 2011 in PCT/JP2010/072766.
U.S. Appl. No. 13/261,300, filed Dec. 17, 2010, Hamamoto et al.
Office Action dated May 14, 2014, in U.S. Appl. No. 13/261,330.
Exhibit 1, search result, p. 1, 2014.
Ostrowski et al,. "An Aza Analogue of *iso*-Levoglucosenone: Synthesis and Application of a New Building Block for Imino Sugars," Eur. J. Org. Chem., 2003, 1104-1110.
Paulsen et al., "Monosaccharides with nitrogen-containing rings. XXV. Preparation of N-substituted derivatives of 5,6-diamino-1,6-anhydro-5,6-dideoxy-β-L-idopyranoses," Chemischte Berichte, 1969, 102(11):3854-62.
Supplementary European Search Report dated Sep. 2, 2014, in EP 10839311.7.
Notice of Allowance in U.S. Appl. No. 13/261,330 dated Jan. 20, 2015.
Holdsworth et al., "World Association for the Advancement of Veterinary Parasitology (W.A.A.V.P) guidelines for evaluating the efficacy of acaricides against ticks (Ixodidae) on ruminants," Veterinary Parasitology, 2006, 136 29-43.
Marchiondo et al., "World Association for the Advancement of Veterinary Parasitology (W.A.A.V.P) guidlines for evaluating the efficacy of parasiticides for the treatment, prevention and control of flea and tick infestation on dogs and cats," Veterinary Parasitology 2007, 145:332-344.

* cited by examiner

CYCLIC AMINE COMPOUND AND ACARICIDE

TECHNICAL FIELD

The present invention relates to a cyclic amine compound and an acaricide. More specifically, the present invention relates to a cyclic amine compound and a acaricide which has a superior acaricidal activity, has a superior property and safety, and can be synthesized advantageously and industrially.

CROSS-REFERENCE TO RELATED APPLICATIONS

This application is a National Stage application of PCT/JP2011/054173, filed Feb. 24, 2011, which claims priority to Japanese Patent Application No. 2010-039839, filed Feb. 25, 2010, Japanese Patent Application No. 2010-117392, filed May 21, 2010, Japanese Patent Application No. 2010-224844, filed Oct. 4, 2010, the content of which is incorporated herein by reference.

BACKGROUND ART

A compound represented by formula (A), which is structurally relevant to the compound of the present invention is disclosed in Patent document 1. It is described that this compound is effective as a serotonin 4 acceptor stimulant. However, a specific synthesis process and effect of the compound represented by formula (A), wherein X represents an oxygen atom, Y represents an alkoxy group and q represents 0, is not described.

[Chemical formula 1]

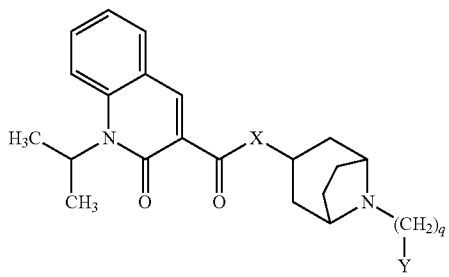

(A)

In addition, a compound represented by formula (B), a salt and an N-oxide of the compound represented by formula (B), and a pest control agent including the compound represented by formula (B) as an active ingredient are disclosed in Patent document 2 (in formula (B), $R^1$ represents a hydroxy group or the like, m represents 0 or an integer of 1 to 5, $R^2$ represents a halogen atom or the like, k represents 0 or an integer of 1 to 4, $R^3$, $R^{31}$, $R^4$, $R^{41}$, $R^5$, $R^{51}$, $R^6$, $R^{61}$ and $R^7$ independently represent a hydrogen atom or the like, X represents an oxygen atom or the like, n represents 0 or 1).

[Chemical formula 2]

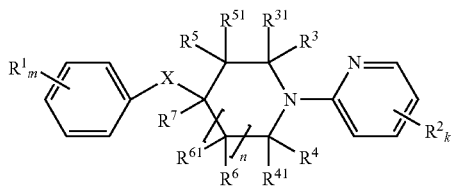

(B)

In addition, an N-pyridyl piperidine compound represented by formula (C) is disclosed in Patent document 3. It is disclosed that the compound represented by formula (C) has a miticidal activity against spider mites and rust mites (in formula (C), $R^1$ represents a halogen atom, a C1-4 haloalkyl group, a cyano group, a nitro group or a C1-4 alkoxycarbonyl group. $R^2$, $R^3$, $R^4$, $R^5$, $R^6$, $R^7$, $R^8$ and $R^9$ independently represent a hydrogen atom or a C1-4 alkyl group. $R^{10}$ represents a hydrogen atom or the like. $R^{11}$ represents a halogen atom or the like. X represents an oxygen atom or a sulfur atom. m represents an integer of 1 to 4. n represents 1 or 2).

[Chemical formula 3]

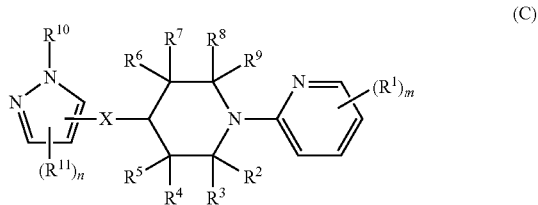

(C)

PRIOR ART LITERATURE

Patent Documents

Patent document 1: Japanese Unexamined Patent Application Publication No. Hei 8-34784
Patent document 2: WO2005/095380
Patent document 3: WO2008/026658

DISCLOSURE OF INVENTION

Problems to be Solved by the Invention

The traditional acaricides, although they can be industrially and advantageously synthesized, and safely-used, many of them lack other properties such as residual efficacy. In addition, the requirements of the safety such as lowering the harmful effect of chemicals to plants, lowering or neutralizing toxicity to humans, livestock or marine life have been growing every year.

Therefore, the objective of the present invention is to provide a novel cyclic amine compound and an acaricide, which has a superior miticidal activity, has a superior property and safety, and can be advantageously and industrially synthesized.

Furthermore, the objective of the present invention is to provide a hydroxylamine compound which is suitable for synthesizing the cyclic amine compound used as an active ingredient of the acaricide.

Means for Solving the Problems

In order to achieve the above objectives, the present inventors conducted extensive studies. As a result, the present inventors discovered that a cyclic amine compound having a specific structure, or salt thereof may be used as an acaricide having a superior miticidal activity, excellent properties and a high safety. Moreover, the present inventors discovered that a hydroxylamine compound having a specific structure, or salt thereof is suitable for an intermediate for synthesizing the cyclic amine compound having a specific structure, or salt thereof.

The present invention was achieved on the basis of this perception.

Namely, the present invention is as follows:

[1] A cyclic amine compound represented by formula (I) or salt thereof:

[Chemical formula 4]

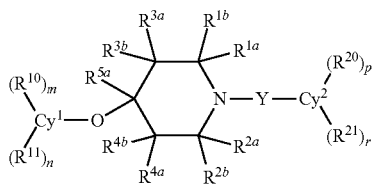

in formula (I),

Cy$^1$ and Cy$^2$ independently represent a C6-10 aryl group or a heterocyclyl group;

in formula (I), R$^{1a}$, R$^{1b}$, R$^{2a}$, R$^{2b}$, R$^{3a}$, R$^{3b}$, R$^{4a}$, R$^{4b}$ and R$^{5a}$ independently represent a hydrogen atom or an unsubstituted or substituted C1-6 alkyl group;

R$^{1a}$ and R$^{2a}$, or R$^{3a}$ and R$^{4a}$ bond together to form an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$— or a group represented by formula: —CH$_2$NR$^6$CH$_2$—, (provided that R$^6$ represents a hydrogen atom, an unsubstituted or substituted C1-6 alkyl group, an unsubstituted or substituted C1-7 acyl group or an unsubstituted or substituted C1-6 alkoxycarbonyl group);

in formula (I), R$^{10}$, R$^{11}$, R$^{20}$ and R$^{21}$ independently represent an unsubstituted or substituted C1-6 alkyl group, an unsubstituted or substituted C3-8 cycloalkyl group, an unsubstituted or substituted C2-6 alkenyl group, an unsubstituted or substituted C2-6 alkynyl group, a hydroxy group, an oxo group, an unsubstituted or substituted C1-6 alkoxy group, an unsubstituted or substituted C3-8 cycloalkoxy group, an unsubstituted or substituted C2-6 alkenyloxy group, an unsubstituted or substituted C2-6 alkynyloxy group, a carboxyl group, an unsubstituted or substituted C1-7 acyl group, an unsubstituted or substituted C1-6 alkoxycarbonyl group, an unsubstituted or substituted C3-8 cycloalkyloxycarbonyl group, an unsubstituted or substituted C2-6 alkenyloxycarbonyl group, an unsubstituted or substituted C2-6 alkynyloxycarbonyl group, an unsubstituted or substituted C6-10 aryloxycarbonyl group, an unsubstituted or substituted heterocyclyloxycarbonyl group, an unsubstituted or substituted C1-7 acyloxy group, an unsubstituted or substituted C1-6 alkoxycarbonyloxy group, an unsubstituted or substituted C3-8 cycloalkyloxycarbonyloxy group, an unsubstituted or substituted C2-6 alkenyloxycarbonyloxy group, an unsubstituted or substituted C2-6 alkynyloxycarbonyloxy group, an unsubstituted or substituted C1-6 alkyl aminocarbonyloxy group, an unsubstituted or substituted C3-8 cycloalkyl aminocarbonyloxy group, an unsubstituted or substituted C2-6 alkenyl aminocarbonyloxy group, an unsubstituted or substituted C2-6 alkynyl aminocarbonyloxy group, an unsubstituted or substituted C6-10 aryl aminocarbonyloxy group, an unsubstituted or substituted heterocyclyl aminocarbonyloxy group, an unsubstituted or substituted aminooxy group, an unsubstituted or substituted C1-6 alkylidene aminooxy group, an unsubstituted or substituted C6-10 aryl group, an unsubstituted or substituted heterocyclyl group, an unsubstituted or substituted C6-10 aryloxy group, an unsubstituted or substituted heterocyclyloxy group, a substituted sulfonyloxy group, an amino group, an unsubstituted or substituted C1-6 alkyl amino group, an unsubstituted or substituted C3-8 cycloalkyl amino group, an unsubstituted or substituted C2-6 alkenyl amino group, an unsubstituted or substituted C2-6 alkynyl amino group, an unsubstituted or substituted C6-10 aryl amino group, an unsubstituted or substituted heterocyclyl amino group, an unsubstituted or substituted hydroxyamino group, an unsubstituted or substituted C1-7 acyl amino group, an unsubstituted or substituted C1-6 alkoxycarbonyl amino group, an unsubstituted or substituted C2-6 alkenyloxycarbonyl amino group, an unsubstituted or substituted C2-6 alkynyloxycarbonyl amino group, an unsubstituted or substituted C6-10 aryloxycarbonyl amino group, an unsubstituted or substituted heterocyclyloxycarbonyl amino group, a substituted sulfonyl amino group, an unsubstituted or substituted aminocarbonyl group, a mercapto group, an unsubstituted or substituted C1-6 alkyl thio group, an unsubstituted or substituted C3-8 cycloalkyl.thio group, an unsubstituted or substituted C2-6 alkenyl thio group, an unsubstituted or substituted C2-6 alkynyl thio group, an unsubstituted or substituted C6-10 aryl thio group, an unsubstituted or substituted heterocyclyl thio group, (an unsubstituted or substituted C1-6 alkyl)thiocarbonyl group, (an unsubstituted or substituted C1-6 alkoxy)thiocarbonyl group, (an unsubstituted or substituted C1-6 alkyl thio)carbonyl group, (an unsubstituted or substituted C1-6 alkyl thio)thiocarbonyl group, a substituted sulfinyl group, a substituted sulfonyl group, a pentafluorosulfanyl group, a tri C1-6 alkyl-substituted silyl group, a tri C6-10 aryl-substituted silyl group, a cyano group, a nitro group or a halogen atom;

R$^{10}$ and R$^{11}$ of Cy$^1$ may independently form a ring, or bond together to form a ring, or bond with the atoms constituting Cy$^1$ to form a ring; R$^{20}$ and R$^{21}$ of Cy$^2$ may independently form, a ring, or bond together to form a ring, or bond with the atoms constituting Cy$^2$ to form a ring;

in formula (I), m represents the number of R$^{10}$ and represents an integer of 0 to 5, when m is 2 or more, R$^{10}$s may be the same or different;

in formula (I), n represents the number of R$^{11}$ and represents an integer of 0 to 5, when n is 2 or more, R$^{11}$s may be the same and different;

in formula (I), p represents the number of R$^{20}$ and represents an integer of 0 to 5, when p is 2 or more, R$^{20}$s may be the same or different;

in formula (I), r represents the number of R$^{21}$ and represents an integer of 0 to 5, when r is 2 or more, R$^{21}$s may be the same or different;

in formula (I), Y represents an oxygen atom or a sulfur atom.

[2] The cyclic amine compound or salt thereof according to [1], wherein in formula (I), Cy$^1$ represents a phenyl group, a pyrazolyl group, a thiadiazolyl group, a pyridyl group, a pyrimidinyl group or a pyridazinyl group, and Cy$^2$ represents a phenyl group, a pyrazolyl group, a thiadiazolyl group, a pyridyl group, a pyrimidinyl group, or a pyridazinyl.

[3] The cyclic amine compound or salt thereof according to [1] or [2], wherein in formula (I), R$^{10}$ represents a C1-6 alkyl group, a C1-6 alkoxy C1-6 alkyl group, a C1-6 alkoxy C1-6 alkoxy C1-6 alkyl group, a C2-6 alkenyl group, a hydroxy group, a C1-6 alkoxy group, a C1-6 haloalkoxy group, a C3-8 cycloalkoxy group, a C2-6 alkenyloxy group, a C2-6 haloalkenyloxy group, a C2-6 alkynyloxy group, a C2-6 haloalkynyloxy group, a C1-6 alkoxy C1-6 alkoxy group, a C3-8 cycloalkyl C1-6 alkoxy group, a cyano C1-6 alkoxy group, a C1-7 acyl C1-6 alkoxy group, a hydroxy C1-6 alkoxy group, a C1-7 acyloxy group, a C1-6 alkoxycarbonyl group, a C2-6 alkenyloxycarbonyl group, a C2-6 alkynyloxycarbonyl group, a C1-6 alkoxycarbonyloxy group, a C1-6 alkyl aminocarbonyloxy group, a C6-10 aryl group, a heterocyclyl group, a C1-6 haloalkyl sulfonyloxy group, a C1-6 alkylidene aminooxy group, a C1-6 alkoxycarbonyl amino group, an unsubstituted or substituted C7-11 aralkyl group, an unsubstituted or substituted C7-11 aralkyloxy group, a C1-6 alkyl thio group or a nitro group;

in formula (I), $R^{11}$ represents a cyano group, a halogen atom, a pentafluorosulfanyl group, a C1-6 haloalkyl group, a C2-6 haloalkenyl group or a C2-6 haloalkynyl group;

in formula (I), $R^{20}$ represents a cyano group, a halogen atom, a pentafluorosulfanyl group, a C1-6 haloalkyl group, a C2-6 haloalkenyl group or a C2-6 haloalkynyl group; and in formula (I), $R^{21}$ represents a C1-6 alkyl group, a C1-6 alkoxy C1-6 alkyl group, a C1-6 alkoxy C1-6 alkoxy C1-6 alkyl group, a hydroxy group, a C1-6 alkoxy group, a C1-6 haloalkoxy group, a C2-6 haloalkenyloxy group, a C2-6 haloalkynyloxy group, a C1-6 alkoxy C1-6 alkoxy group, a C3-8 cycloalkyl C1-6 alkoxy group, a C1-6 alkoxycarbonyl group, a C2-6 alkenyloxycarbonyl group, a C2-6 alkynyloxycarbonyl group, a C1-6 alkylidene aminooxy group, a C1-6 alkoxycarbonyl amino group, an unsubstituted or substituted C7-11 aralkyl group, an unsubstituted or substituted C7-11 aralkyloxy group or a nitro group.

[4] The cyclic amine compound or salt thereof according to any one of [1]-[3], wherein $Cy^1$ represents a phenyl group;

$R^{1b}$, $R^{2b}$, $R^{3a}$, $R^{3b}$, $R^{4a}$, $R^{4b}$ and $R^{5a}$ represent a hydrogen atom;

$R^{1a}$ and $R^{2a}$ bond together to form an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$— or a group represented by formula: —CH$_2$NR$^6$CH$_2$— (provided that $R^6$ represents a hydrogen atom, an unsubstituted or substituted C1-6 alkyl group, an unsubstituted or substituted C1-7 acyl group or an unsubstituted or substituted C1-6 alkoxycarbonyl group);

$Cy^2$ represents a pyridine-2-yl group;

Y represents an oxygen atom;

r represents 0; and p represents an integer of 0 to 4.

[5] A cyclic amine compound represented by formula (II) or salt thereof:

[Chemical formula 5]

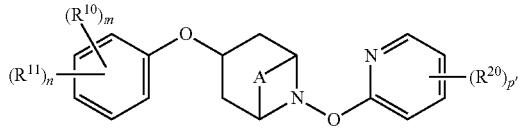

(II)

in formula (II), $R^{10}$, m, $R^{11}$, n and $R^{20}$ are the same as previously defined in formula (I).

in formula (II), A represents an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$— or a group represented by formula: —CH$_2$NR$^6$CH$_2$— (provided that $R^6$ represents a hydrogen atom, an unsubstituted or substituted C1-6 alkyl group, an unsubstituted or substituted C1-7 acyl group or an unsubstituted or substituted C1-6 alkoxycarbonyl group).

in formula (II), p' represents the number of $R^{20}$ and represents an integer of 0 to 4. When p' is 2 or more, $R^{20}$s are the same or different.

[6] The cyclic amine compound according to [5], wherein in formula (II), $R^{10}$ represents a C1-6 alkyl group, a C1-6 alkoxy C1-6 alkyl group, a C1-6 alkoxy C1-6 alkoxy C1-6 alkyl group, a C2-6 alkenyl group, a hydroxy group, a C1-6 alkoxy group, a C1-6 haloalkoxy group, a C3-8 cycloalkoxy group, a C2-6 alkenyloxy group, a C2-6 haloalkenyloxy group, a C2-6 alkynyloxy group, a C2-6 haloalkynyloxy group, a C1-6 alkoxy C1-6 alkoxy group, a C3-8 cycloalkyl C1-6 alkoxy group, a cyano C1-6 alkoxy group, a C1-7 acyl C1-6 alkoxy group, a hydroxy C1-6 alkoxy group, a C1-7 acyloxy group, a C1-6 alkoxycarbonyl group, a C2-6 alkenyloxycarbonyl group, a C2-6 alkynyloxycarbonyl group, a C1-6 alkoxycarbonyloxy group, a C1-6 alkyl aminocarbonyloxy group, a C6-10 aryl group, a heterocyclyl group, a C1-6 haloalkyl sulfonyloxy group, a C1-6 alkylidene aminooxy group, a C1-6 alkoxycarbonyl amino group, an unsubstituted or substituted C7-11 aralkyl group, an unsubstituted or substituted C7-11 aralkyloxy group, a C1-6 alkyl thio group or a nitro group;

in formula (II), $R^{11}$ represents a cyano group, a halogen atom, a pentafluorosulfanyl group, a C1-6 haloalkyl group, a C2-6 haloalkenyl group or a C2-6 haloalkynyl group; and in formula (II), $R^{20}$ represents a cyano group, a halogen atom, a pentafluorosulfanyl group, a C1-6 haloalkyl group, a C2-6 haloalkenyl group or a C2-6 haloalkynyl group.

[7] A pest control agent comprising at least one selected from the cyclic amine compound or salt thereof according to any one of [1]-[6] as an active ingredient.

[8] An acaricide comprising at least one selected from the cyclic amine compound or salt thereof according to any one of [1]-[6] as an active ingredient.

[9] A hydroxylamine compound represented by formula (III) or salt thereof:

[Chemical formula 6]

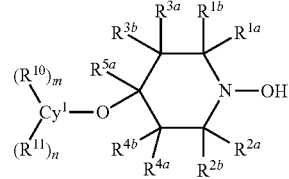

(III)

in formula (III), $Cy^1$ represents a C6-10 aryl group or a heterocyclyl group;

in formula (III), $R^{1a}$, $R^{1b}$, $R^{2a}$, $R^{2b}$, $R^{3a}$, $R^{3b}$, $R^{4a}$, $R^{3b}$ and $R^{5a}$ independently represents a hydrogen atom or an unsubstituted or substituted C1-6 alkyl group; and $R^{1a}$ and $R^{2a}$, or $R^{3a}$ and $R^{4a}$ bond together to form an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$— or a group represented by formula: —CH$_2$NR$^6$CH$_2$— (provided that $R^6$ represents a hydrogen atom, an unsubstituted or substituted C1-6 alkyl group, an unsubstituted or substituted C1-7 acyl group or an unsubstituted or substituted C1-6 alkoxycarbonyl group);

in formula (III), $R^{10}$ and $R^{11}$ independently represents an unsubstituted or substituted C1-6 alkyl group, an unsubstituted or substituted C3-8 cycloalkyl group, an unsubstituted or substituted C2-6 alkenyl group, an unsubstituted or substituted C2-6 alkynyl group, a hydroxy group, an oxo group, an unsubstituted or substituted C1-6 alkoxy group, an unsubstituted or substituted C3-8 cycloalkoxy group, an unsubstituted or substituted C2-6 alkenyloxy group, an unsubstituted or substituted C2-6 alkynyloxy group, carboxyl group, an unsubstituted or substituted C1-7 acyl group, an unsubstituted or substituted C1-6 alkoxycarbonyl group, an unsubstituted or substituted C3-8 cycloalkyloxycarbonyl group, an unsubstituted or substituted C2-6 alkenyloxycarbonyl group, an unsubstituted or substituted C2-6 alkynyloxycarbonyl group, an unsubstituted or substituted C6-10 aryloxycarbonyl group,
an unsubstituted or substituted heterocyclyloxycarbonyl group, an unsubstituted or substituted C1-7 acyloxy group, an unsubstituted or substituted C1-6 alkoxycarbonyloxy group, an unsubstituted or substituted C3-8 cycloalkyloxycarbonyloxy group, an unsubstituted or substituted C2-6 alkenyloxycarbonyloxy group, an unsubstituted or substituted C2-6 alkynyloxycarbonyloxy group, an unsubstituted or substituted C1-6 alkyl aminocarbonyloxy group, an unsubstituted or substituted C3-8 cycloalkyl aminocarbonyloxy group, an unsubstituted or substituted C2-6 alkenyl aminocarbonyloxy group, an unsubstituted or substituted C2-6 alkynyl aminocarbonyloxy group, an unsubstituted or substituted C6-10 aryl aminocarbonyloxy group, an unsubstituted or substituted heterocyclyl aminocarbonyloxy group, an unsubstituted or substituted aminooxy group, an unsubstituted or substituted C1-6 alkylidene aminooxy group, an unsubstituted or substituted C6-10 aryl group, an unsubstituted or substituted heterocyclyl group,
an unsubstituted or substituted C6-10 aryloxy group, an unsubstituted or substituted heterocyclyloxy group, a substituted sulfonyloxy group, amino group, an unsubstituted or substituted C1-6 alkyl amino group, an unsubstituted or substituted C3-8 cycloalkyl amino group, an unsubstituted or substituted C2-6 alkenyl amino group, an unsubstituted or substituted C2-6 alkynyl amino group, an unsubstituted or substituted C6-10 aryl amino group, an unsubstituted or substituted heterocyclyl amino group, an unsubstituted or substituted hydroxyamino group, an unsubstituted or substituted C1-7 acyl amino group, an unsubstituted or substituted C1-6 alkoxycarbonyl amino group, an unsubstituted or substituted C2-6 alkenyloxycarbonyl amino group, an unsubstituted or substituted C2-6 alkynyloxycarbonyl amino group, an unsubstituted or substituted C6-10 aryloxycarbonyl amino group, an unsubstituted or substituted heterocyclyloxycarbonyl amino group, a substituted sulfonyl amino group, an unsubstituted or substituted aminocarbonyl group, a mercapto group, an unsubstituted or substituted C1-6 alkyl thio group, an unsubstituted or substituted C3-8 cycloalkyl thio group, an unsubstituted or substituted C2-6 alkenyl thio group, an unsubstituted or substituted C2-6 alkynyl thio group, an unsubstituted or substituted C6-10 aryl thio group, an unsubstituted or substituted heterocyclyl thio group, (an unsubstituted or substituted C1-6 alkyl)thiocarbonyl group, (an unsubstituted or substituted C1-6 alkoxy)thiocarbonyl group, (an unsubstituted or substituted C1-6 alkyl thio)carbonyl group, (an unsubstituted or substituted C1-6 alkyl thio)thiocarbonyl group, a substituted sulfinyl group, a substituted sulfonyl group, a pentafluorosulfanyl group, a tri C1-6 alkyl-substituted silyl group, a tri C6-10 aryl-substituted silyl group, a cyano group, nitro group or a halogen atom;

$R^{10}$ and $R^{11}$ of $Cy^1$ may independently form a ring, or bond together to form a ring, or bond with the atoms constituting $Cy^1$ to form a ring;

in formula (III), m represents the number of $R^{10}$ and represents an integer of 0 to 5, when m is 2 or more, $R^{10}$s may be the same or different;

in formula (III), n represents the number of $R^{11}$ and represents an integer of 0 to 5, when n is 2 or more, $R^{11}$s may be the same and different.

[10] The hydroxylamine compound or salt thereof according to [9], wherein
in formula (III), $Cy^1$ represents a phenyl group, a pyrazolyl group, a thiadiazolyl group, a pyridyl group, a pyrimidinyl group or a pyridazinyl group.

[11] The hydroxylamine compound or salt thereof according to [9] or [10], wherein
in formula (III), $R^{10}$ represents a C1-6 alkyl group, a C1-6 alkoxy C1-6 alkyl group, a C1-6 alkoxy C1-6 alkoxy C1-6 alkyl group, a C2-6 alkenyl group, a hydroxy group, a C1-6 alkoxy group, a C1-6 haloalkoxy group, a C3-8 cycloalkoxy group, a C2-6 alkenyloxy group, a C2-6 haloalkenyloxy group, a C2-6 alkynyloxy group, a C2-6 haloalkynyloxy group, a C1-6 alkoxy C1-6 alkoxy group, a C3-8 cycloalkyl C1-6 alkoxy group, a cyano C1-6 alkoxy group, a C1-7 acyl C1-6 alkoxy group, a hydroxy C1-6 alkoxy group, a C1-7 acyloxy group, a C1-6 alkoxycarbonyl group, a C2-6 alkenyloxycarbonyl group, a C2-6 alkynyloxycarbonyl group, a C1-6 alkoxycarbonyloxy group, a C1-6 alkyl aminocarbonyloxy group, a C6-10 aryl group, a heterocyclyl group, a C1-6 haloalkyl sulfonyloxy group, a C1-6 alkylidene aminooxy group, a C1-6 alkoxycarbonyl amino group, an unsubstituted or substituted C7-11 aralkyl group, an unsubstituted or substituted C7-11 aralkyloxy group, a C1-6 alkyl thio group or a nitro group; and in formula (III), $R^{11}$ represents a cyano group, a halogen atom, a pentafluorosulfanyl group, a C1-6 haloalkyl group, a C2-6 haloalkenyl group or a C2-6 haloalkynyl group.

Effects of the Invention

The cyclic amine compound or salt thereof according to the present invention makes it possible to effectively prevent the acaricides which are harmful to agricultural crops or harmful in terms of hygiene.

The hydroxylamine compound or salt thereof according to the present invention makes it possible to easily synthesis the cyclic amine compound or salt thereof according to the present invention.

BEST MODE FOR CARRYING OUT THE INVENTION

[Cyclic Amine Compound]
The amine compound of the present invention is represented by formula (I) or (II). In addition, the salt of the cyclic amine compound of the present invention is a salt of a cyclic compound represented by formula (I) or (II).

The term "unsubstituted" in this description means that a base group is the only group constituting the group. In addition, unless specifically indicated otherwise, a group has the meaning of being "unsubstituted" when the group is not described as being "substituted" and described using the name of the base group.

On the other hand, the term "substituted" means that any of hydrogen atoms of the base group are substituted with a group that is the same as or different from the base group. The "substituted" group may be substituted with one substituent, or two or more substituents. The two or more substituents may be the same or different.

The term "C1-6", for example, means that the base group has 1 to 6 carbon atoms. This number does not include the number of carbon atoms constituting the substituents. For example, a butyl group substituted with an ethoxy group is classified into a C2 alkoxy C4 alkyl group.

The "substituent" is not particularly limited as long as it is chemically permissible and achieves the effects of the present invention.

Examples of the "substituent" include a halogen atom such as a fluorine atom, chlorine atom, bromine atom, iodine atom or the like; a C1-6 alkyl group such as a methyl group, ethyl group, n-propyl group, i-propyl group, n-butyl group, s-butyl group, i-butyl group, t-butyl group, n-pentyl group, n-hexyl group or the like; a C3-8 cycloalkyl group such as a cyclopropyl group, cyclobutyl group, cyclopentyl group, cyclohexyl group, cycloheptyl group or the like; a C2-6 alkenyl group such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group or the like; a C3-8 cycloalkenyl group such as a 2-cyclopropenyl group, 2-cyclopentenyl group, 3-cyclohexenyl group, 4-cyclooctenyl group or the like; a C2-6 alkynyl group such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group or the like;

a C1-6 alkoxy group such as a methoxy group, ethoxy group, n-propoxy group, i-propoxy group, n-butoxy group, s-butoxy group, i-butoxy group, t-butoxy group or the like; a C2-6 alkenyloxy group such as a vinyloxy group, allyloxy group, propenyloxy group, butenyloxy group or the like; a C2-6 alkynyloxy group such as an ethynyloxy group, propargyloxy group or the like; a C6-10 aryl group such as a phenyl group, naphthyl group or the like; a C6-10 aryloxy group such as a phenoxy group, 1-naphthoxy group or the like; a C7-11 aralkyl group such as a benzyl group, phenethyl group or the like; a C7-11 aralkyloxy group such as a benzyloxy group, phenethyloxy group or the like; a C1-7 acyl group such as a formyl group, acetyl group, propionyl group, benzoyl group, cyclohexyl carbonyl group or the like; a C1-7 acyloxy group such as a formyloxy group, acetyloxy group, propionyloxy group, benzoyloxy group, cyclohexyl carbonyloxy group or the like; a C1-6 alkoxycarbonyl group such as a methoxycarbonyl group, ethoxycarbonyl group, n-propoxycarbonyl group, i-propoxycarbonyl group, n-butoxycarbonyl group, t-butoxycarbonyl group or the like; a carboxyl group;

a hydroxy group; an oxo group; a C1-6 haloalkyl group such as a chloromethyl group, chloroethyl group, trifluoromethyl group, 1,2-dichloro-n-propyl group, 1-fluoro-n-butyl group, perfluoro-n-pentyl group or the like; a C2-6 haloalkenyl group such as a 2-chloro-1-propenyl group, 2-fluoro-1-butenyl group or the like; a C2-6 haloalkynyl group such as a 4,4-dichloro-1-butynyl group, 4-fluoro-1-pentynyl group, 5-bromo-2-pentynyl group or the like; a C1-6 haloalkoxy group such as a 2-chloro-n-propoxy group, 2,3-dichlorobutoxy group or the like; a C2-6 haloalkenyloxy group such as a 2-chloropropenyloxy group, 3-bromobutenyloxy group or the like; a C6-10 haloaryl group such as a 4-chlorophenyl group, 4-fluorophenyl group, 2,4-dichlorophenyl group or the like; a C6-10 haloaryloxy group such as a 4-fluorophenyloxy group, 4-chloro-1-naphthoxy group or the like; a halogen-substituted C1-7 acyl group such as a chloroacetyl group, trifluoroacetyl group, trichloroacetyl group, 4-chlorobenzoyl group or the like;

a cyano group; an isocyano group; a nitro group; an isocyanato group; a cyanato group; an amino group; a C1-6 alkyl amino group such as a methyl amino group, dimethyl amino group, diethyl amino group or the like; a C6-10 aryl amino group such as an anilino group, naphthyl amino group or the like; a C7-11 aralkyl amino group such as a benzyl amino group, phenyl ethyl amino group or the like; a C1-7 acyl amino group such as a formyl amino group, acetyl amino group, propanoyl amino group, butyryl amino group, i-propyl carbonyl amino group, benzoyl amino group or the like; a C1-6 alkoxycarbonyl amino group such as a methoxycarbonyl amino group, ethoxycarbonyl amino group, n-propoxycarbonyl amino group, i-propoxycarbonyl amino group or the like; an unsubstituted or substituted aminocarbonyl group such as an aminocarbonyl group, dimethyl aminocarbonyl group, phenyl aminocarbonyl group, N-phenyl-N-methyl aminocarbonyl group or the like; an imino-substituted C1-6 alkyl group such as an iminomethyl group, (1-imino)ethyl group, (1-imino)-n-propyl group or the like; a hydroxyimino-substituted C1-6 alkyl group such as a hydroxyiminomethyl group, (1-hydroxyimino)ethyl group, (1-hydroxyimino)propyl group, methoxyiminomethyl group, (1-methoxyimino)ethyl group or the like;

a mercapto group; an isothiocyanato group; a thiocyanato group; a C1-6 alkyl thio group such as a methyl thio group, ethyl thio group, n-propyl thio group, i-propyl thio group, n-butyl thio group, i-butyl thio group, s-butyl thio group, t-butyl thio group or the like; a C2-6 alkenyl thio group such as a vinyl thio group, allyl thio group or the like; a C2-6 alkynyl thio group such as an ethynyl thio group, propargyl thio group or the like; a C6-10 aryl thio group such as a phenyl thio group, naphthyl thio group or the like; a heterocyclyl thio group such as a thiazolyl thio group, pyridyl thio group or the like; a C7-11 aralkyl thio group such as a benzyl thio group, phenethyl thio group or the like; a (C1-6 alkyl thio)carbonyl group such as a (methyl thio)carbonyl group, (ethyl thio) carbonyl group, (n-propyl thio)carbonyl group, (i-propyl thio)carbonyl group, (n-butyl thio)carbonyl group, (i-butyl thio)carbonyl group, (s-butyl thio)carbonyl group, (t-butyl thio)carbonyl group or the like;

a C1-6 alkyl sulfinyl group such as methyl sulfinyl group, ethyl sulfinyl group, t-butyl sulfinyl group or the like; a C2-6 alkenyl sulfinyl group such as an allyl sulfinyl group or the like; a C2-6 alkynyl sulfinyl group such as a propargyl sulfinyl group or the like; a C6-10 aryl sulfinyl group such as a phenyl sulfinyl group or the like; a heterocyclyl sulfinyl group such as a thiazolyl sulfinyl group, pyridyl sulfinyl group or the like; a C7-11 aralkyl sulfinyl group such as a benzyl sulfinyl group, phenethyl sulfinyl group or the like; a C1-6 alkyl sulfonyl group such as a methyl sulfonyl group, ethyl sulfonyl group, t-butyl sulfonyl group or the like; a C2-6 alkenyl sulfonyl group such as an allyl sulfonyl group or the like; a C2-6 alkynyl sulfonyl group such as a propargyl sulfonyl group or the like; a C6-10 aryl sulfonyl group such as a phenyl sulfonyl group or the like; a heterocyclyl sulfonyl group such as a thiazolyl sulfonyl group, pyridyl sulfonyl group or the like; a C7-11 aralkyl sulfonyl group such as a benzyl sulfonyl group, phenethyl sulfonyl group or the like;

a 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like; a 6-membered heteroaryl group such as a pyridyl group, pyrazinyl group, pyrimidinyl group, pyridazinyl group, triazinyl group or the like; a saturated heterocyclyl group such as an aziridinyl group, epoxy group, pyrrolidinyl group, tetrahydrofuranyl group, piperidyl group, piperazinyl group, morpholinyl group or the like; a tri C1-6 alkyl-substituted silyl group such as a trimethyl silyl group, triethyl silyl group, t-butyl dimethyl silyl group or the like; a triphenyl silyl group or the like; or the like.

In addition, these "substituents" may be substituted with other "substituents".

[$Cy^1$, $Cy^2$]

In formula (I), $Cy^1$ and $Cy^2$ independently represent a C6-10 aryl group or a heterocyclic group.

The "C6-10 aryl group" of $Cy^1$ and $Cy^2$ may be a monocyclic or polycyclic C6-10 aryl group. In the polycyclic aryl group, as long as it includes at least one aromatic ring, other rings may be a saturated alicyclic ring, an unsaturated alicyclic ring or an aromatic ring. Examples of the C6-10 aryl group include a phenyl group, naphthyl group, azulenyl group, indenyl group, indanyl group, tetralinyl group or the like. Among these groups, a phenyl group is preferable as the "C6-10 aryl group" of $Cy^1$ or $Cy^2$.

The "heterocyclyl group" of $Cy^1$ and $Cy^2$ is as group in which 1-4 hetero atoms selected from a nitrogen atom, oxygen atom and sulfur atom are included as the atoms constituting the ring. The heterocyclyl group may be a monoheterocyclyl group or a polyheterocyclyl group.

Examples of the heterocyclyl group include a 5-membered heteroaryl group, 6-membered heteroaryl group, condensed heteroaryl group, saturated heterocylclyl group, partially-unsaturated heterocyclyl group or the like.

Examples of the 5-membered heteroaryl group include a pyrrolyl group such as a pyrrole-1-yl group, pyrrole-2-yl group, pyrrole-3-yl group or the like; a furyl group such as a furan-2-yl group, furan-3-yl group or the like; a thienyl group such as a thiophene-2-yl group, thiophene-3-yl group or the like; a imidazolyl group such as an imidazole-1-yl group, imidazole-2-yl group, imidazole-4-yl group, imidazole-5-yl group or the like; a pyrazolyl group such as a pyrazole-1-yl group, pyrazole-3-yl group, pyrazole-4-yl group, pyrazole-5-yl group or the like; an oxazolyl group such as an oxazole-2-yl group, oxazole-4-yl group, oxazole-5-yl group or the like; an isoxazolyl group such as an isoxazole-3-yl group, isoxazole-4-yl group, isoxazole-5-yl group or the like; a thiazolyl group such as a thiazole-2-yl group, thiazole-4-yl group, thiazole-5-yl group or the like; an isothiazolyl group such as an isothiazole-3-yl group, isothiazole-4-yl group, isothiazole-5-yl group or the like; a triazolyl group such as a 1,2,3-triazole-1-yl group, 1,2,3-triazole-4-yl group, 1,2,3-triazole-5-yl group, 1,2,4-triazole-1-yl group, 1,2,4-triazole-3-yl group, 1,2,4-triazole-5-yl group or the like; an oxadiazolyl group such as a 1,2,4-oxadiazole-3-yl group, 1,2,4-oxadiazole-5-yl group, 1,3,4-oxadiazole-2-yl group or the like; a thiadiazolyl group such as a 1,2,4-thiadiazole-3-yl group, 1,2,4-thiadiazole-5-yl group, 1,3,4-thiadiazole-2-yl group or the like; a tetrazolyl group such as a tetrazole-1-yl group, tetrazole-2-yl group or the like; or the like.

Examples of the 6-membered heteroaryl group include a pyridyl group such as a pyridine-2-yl group, pyridine-3-yl group, pyridine-4-yl group or the like; a pyrazinyl group such as a pyrazine-2-yl group, pyrazine-3-yl group or the like; a pyrimidinyl group such as a pyrimidine-2-yl group, pyrimidine-4-yl group, pyrimidine-5-yl group or the like; a pyridazinyl group such as a pyridazine-3-yl group, pyridazine-4-yl group or the like; a triazinyl group or the like; or the like.

Examples of the condensed heteroaryl group include an indole-1-yl group, indole-2-yl group, indole-3-yl group, indole-4-yl group, indole-5-yl group, indole-6-yl group, indole-7-yl group; a benzofuran-2-yl group, benzofuran-3-yl group, benzofuran-4-yl group, benzofuran-5-yl group, benzofuran-6-yl group, benzofuran-7-yl group; a benzothiophene-2-yl group, benzothiophene-3-yl group, benzothiophene-4-yl group, benzothiophene-5-yl group, benzothiophene-6-yl group, benzothiophene-7-yl group; a benzimidazole-1-yl group, benzimidazole-2-yl group, benzimidazole-4-yl group, benzimidazole-5-yl group, benzoxazole-2-yl group, benzoxazole-4-yl group, benzoxazole-5-yl group, benzothiazole-2-yl group, benzothiazole-4-yl group, benzothiazole-5-yl group; a quinoline-2-yl group, quinoline-3-yl group, quinoline-4-yl group, quinoline-5-yl group, quinoline-6-yl group, quinoline-7-yl group, quinoline-8-yl group or the like; or the like.

Examples of other heterocyclyl group include an aziridine-1-yl group, aziridine-2-yl group, epoxy group; a pyrrolidine-1-yl group, pyrrolidine-2-yl group, pyrrolidine-3-yl group, tetrahydrofuran-2-yl group, tetrahydrofuran-3-yl group; a [1,3]dioxirane-2-yl group, [1,3]dioxirane-4-yl group; a piperidine-1-yl group, piperidine-2-yl group, piperidine-3-yl group, piperidine-4-yl group, piperazine-1-yl group, piperazine-2-yl group, morpholine-2-yl group, morpholine-3-yl group, morpholine-4-yl group; a 1,3-benzodioxole-4-yl group, 1,3-benzodioxole-5-yl group, 1,4-benzodioxane-5-yl group, 1,4-benzodioxane-6-yl group, 3,4-dihydro-2H-1,5-benzodioxepine-6-yl group, 3,4-dihydro-2H-1,5-benzodioxepine-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group; or the like.

Among these groups, the heterocyclyl group of $Cy^1$ or $Cy^2$ is preferably a 5-membered heteroaryl group or a 6-membered heteroaryl group, more preferably a pyrazolyl group, a thiadiazolyl group, pyridyl group, pyrimidinyl group, or a pyridazinyl group.

In the cyclic amine compound of the present invention, $Cy^1$ is preferably a phenyl group, $Cy^2$ is preferably a pyridyl group.

[$R^{1a}$, $R^{1b}$, $R^{2a}$, $R^{2b}$, $R^{3a}$, $R^{3b}$, $R^{4a}$, $R^{4b}$ and $R^{5a}$]

In formula (I), $R^{1a}$, $R^{1b}$, $R^{2a}$, $R^{2b}$, $R^{3a}$, $R^{3b}$, $R^{4a}$, $R^{4b}$ and $R^{5a}$ (hereinafter, may be referred to as "$R^{1a}$ or the like") independently represents a hydrogen atom or an unsubstituted or substituted C1-6 alkyl group; $R^{1a}$ and $R^{2a}$, or $R^{3a}$ and $R^{4a}$ bond together to form an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$—, or a group represented by formula: —CH$_2$NR$^6$CH$_2$— (provided that $R^6$ represents a hydrogen atom, an unsubstituted or substituted C1-6 alkyl group, an unsubstituted or substituted C1-7 acyl group, or an unsubstituted or substituted C1-6 alkoxycarbonyl group). In addition, the group formed by boding $R^{1a}$ with $R^{2a}$, $R^{3a}$ with $R^{4a}$ may be referred to as "cross-linking moiety".

The "C1-6 alkyl group" of $R^{1a}$ or the like may be a linear alkyl group or a branched alkyl group. Examples of the alkyl group include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methyl butyl group, 2,2-dimethyl propyl group, i-hexyl group or the like.

Examples of the "substituted C1-6 alkyl group" of $R^{1a}$ or the like include a C3-8 cycloalkyl C1-6 alkyl group such as a cyclopropyl methyl group, 2-cyclopropyl ethyl group, cyclopentyl methyl group, 2-cyclohexyl ethyl group, 2-cyclooctyl ethyl group or the like; a C1-6 haloalkyl group such as a fluoromethyl group, chloromethyl group, bromomethyl group, difluoromethyl group, dichloromethyl group, dibromomethyl group, trifluoromethyl group, trichloromethyl group, tribromomethyl group, 2,2,2-tolufluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethyl ethyl group, perfluorohexyl group, perchlorohexyl group, perfluorooctyl group, perchlorooctyl group, 2,4,6-trichlorohexyl group, hexafluoroisopropyl group, pentafluoroisopropyl group, perfluoromethoxy group or the like;

a hydroxy C1-6 alkyl group such as a hydroxymethyl group, 2-hydroxyethyl group or the like; a C1-6 alkoxy C1-6 alkyl group such as a methoxymethyl group, ethoxymethyl group, methoxyethyl group, ethoxyethyl group, methoxy-n-propyl group, n-propoxymethyl group, i-propoxymethyl group, i-propoxyethyl group, s-butoxymethyl group, t-butoxyethyl group or the like; a C1-6 alkoxy C1-6 alkoxy C1-6 alkyl group such as a methoxymethoxymethyl group, 1-methoxyethoxymethyl group, 2-methoxyethoxymethyl group, 2-(1-methoxyethoxy)ethyl group, 2-(2-methoxyethoxy)ethyl group or the like; a di C1-6 alkoxy C1-6 alkyl group such as a dimethoxymethyl group, diethoxymethyl group, 2,2-dimethoxyethyl group, 1,2-dimethoxyethyl group, 3,3-dimethoxy n-propyl group, 2,2-diethoxyethyl group or the like; a C1-7 acyloxy C1-6 alkyl group such as a formyloxymethyl group, acetoxymethyl group, 2-acetoxyethyl group, propionyloxymethyl group, propionyloxyethyl group or the like; an imino-substituted C1-6 alkyl group such as a iminomethyl group, (1-imino)ethyl group, (1-imino)propyl group or the like;

a hydroxyimino-substituted C1-6 alkyl group such as a hydroxyiminomethyl group, (1-hydroxyimino)ethyl group, (1-hydroxyimino)-n-propyl group, methoxyiminomethyl group, (1-methoxyimino)ethyl group or the like;

an unsubstituted or substituted C7-11 aralkyl group such as an unsubstituted or substituted benzyl group, an unsubstituted or substituted phenethyl group or the like; or the like.

Examples of the "C3-6 alkylene group" formed by bonding $R^{1a}$ with $R^{2a}$, or $R^{3a}$ with $R^{4a}$ include a trimethylene group, a tetramethylene group, propylene group or the like. Among these groups, a C3-4 alkylene group is preferable.

In addition, examples of the "C3-6 alkenylene group" include a propenylene group, a 2-butenylene group or the like. Among these groups, a C3-4 alkenylene group is preferable.

Examples of the possible "substituent" include a halogen atom such as a fluorine atom, chlorine atom, bromine atom, iodine atom or the like; a C1-6 alkyl group such as a methyl group, ethyl group, n-propyl group, i-propyl group, n-butyl group, s-butyl group, i-butyl group, t-butyl group, n-pentyl group, n-hexyl group or the like; a C3-6 cycloalkyl group such as a cyclopropyl group, cyclobutyl group, cyclopentyl group, cyclohexyl group or the like; a C1-6 alkoxy group such as a methoxy group, ethoxy group, n-propoxy group, i-propoxy group, n-butoxy group, s-butoxy group, i-butoxy group, t-butoxy group or the like; a hydroxy group; a C1-6 haloalkyl group such as a chloromethyl group, chloroethyl group, trifluoromethyl group, 1,2-dichloro-n-propyl group, 1-fluoro-n-butyl group, perfluoro-n-pentyl group or the like; or the like.

In formula $-CH_2NR^6CH_2-$, $R^6$ represents a hydrogen atom, an unsubstituted or substituted C1-6 alkyl group, an unsubstituted or substituted C1-7 acyl group, or an unsubstituted or substituted C1-6 alkoxycarbonyl group.

Examples of the "unsubstituted or substituted C1-6 alkyl group" of $R^6$ are the same as those listed as examples of $R^{1a}$ or the like.

Examples of the "C1-7 acyl group" of $R^6$ include a formyl group, acetyl group, propionyl group, benzoyl group, cyclohexyl carbonyl group or the like.

Examples of the "substituted C1-7 acyl group" of $R^6$ include a chloroacetyl group, trifluoroacetyl group, trichloroacetyl group, 4-chlorobenzoyl group or the like.

Examples of the "C1-6 alkoxycarbonyl group" of $R^6$ include a methoxycarbonyl group, ethoxycarbonyl group, n-propoxycarbonyl group, i-propoxycarbonyl group, n-butoxycarbonyl group, t-butoxycarbonyl group or the like.

Examples of the "substituted C1-6 alkoxycarbonyl group" of $R^6$ include a C3-8 cycloalkyl C1-6 alkoxycarbonyl group such as a cyclopropyl methoxycarbonyl group, cyclobutyl methoxycarbonyl group, cyclopentyl methoxycarbonyl group, cyclohexyl methoxycarbonyl group, 2-methyl cyclopropyl methoxycarbonyl group, 2,3-dimethyl cyclopropyl methoxycarbonyl group, 2-chlorocyclopropyl methoxycarbonyl group, 2-cyclopropyl ethoxycarbonyl group or the like; a C1-6 haloalkoxycarbonyl group such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group, 2,2,2-trichloroethoxycarbonyl group, pentafluoroethoxycarbonyl group, 4-fluorobutoxycarbonyl group, 3,3,3-trifluoropropoxycarbonyl group, 2,2,2-trifluoro-1-trifluoromethyl ethoxycarbonyl group, perfluorohexyloxycarbonyl group or the like; or the like.

The following partial structural formulas (a1)-(a4) are shown for explaining the cross-liking moiety specifically. In formulas (a1)-(a4), *1 represents the position bonding with Y, *2 represents the position bonding with oxygen atom. X's independently represents $-CH_2-$, an oxygen atom, a sulfur atom, $-NR^6-$, a carbonyl group or the like. The present invention also includes isomers in which the cross-liking moiety has exo-relation or endo-relation with $R^{5a}$, or mixtures thereof.

[Chemical formula 7]

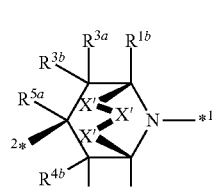

(a1)

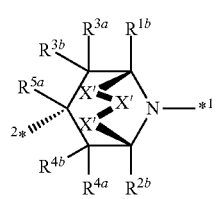

(a2)

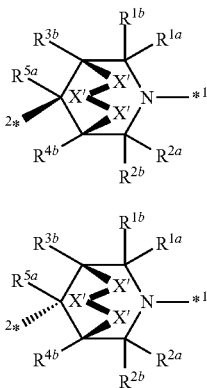

[$R^{10}$, $R^{11}$, $R^{20}$, $R^{21}$]

In formula (I), $R^{10}$, $R^{11}$, $R^{20}$ and $R^{21}$ (hereafter, may be referred to as "$R^{10}$ or the like") independently represent an unsubstituted or substituted C1-6 alkyl group, an unsubstituted or substituted C3-8 cycloalkyl group, an unsubstituted or substituted C2-6 alkenyl group, an unsubstituted or substituted C2-6 alkynyl group, a hydroxy group, an oxo group, an unsubstituted or substituted C1-6 alkoxy group, an unsubstituted or substituted C3-8 cycloalkoxy group, an unsubstituted or substituted C2-6 alkenyloxy group, an unsubstituted or substituted C2-6 alkynyloxy group, a carboxyl group, an unsubstituted or substituted C1-7 acyl group, an unsubstituted or substituted C1-6 alkoxycarbonyl group, an unsubstituted or substituted C3-8 cycloalkyloxycarbonyl group, an unsubstituted or substituted C2-6 alkenyloxycarbonyl group, an unsubstituted or substituted C2-6 alkynyloxycarbonyl group, an unsubstituted or substituted C6-10 aryloxycarbonyl group, an unsubstituted or substituted heterocyclyloxycarbonyl group, an unsubstituted or substituted C1-7 acyloxy group, an unsubstituted or substituted C1-6 alkoxycarbonyloxy group, an unsubstituted or substituted C3-8 cycloalkyloxycarbonyloxy group, an unsubstituted or substituted C2-6 alkenyloxycarbonyloxy group, an unsubstituted or substituted C2-6 alkynyloxycarbonyloxy group, an unsubstituted or substituted C1-6 alkyl aminocarbonyloxy group, an unsubstituted or substituted C3-8 cycloalkyl aminocarbonyloxy group, an unsubstituted or substituted C2-6 alkenyl aminocarbonyloxy group, an unsubstituted or substituted C2-6 alkynyl aminocarbonyloxy group, an unsubstituted or substituted C6-10 aryl aminocarbonyloxy group, an unsubstituted or substituted heterocyclyl aminocarbonyloxy group, an unsubstituted or substituted aminooxy group, an unsubstituted or substituted C1-6 alkylidene aminooxy group, an unsubstituted or substituted C6-10 aryl group, an unsubstituted or substituted heterocyclyl group, an unsubstituted or substituted C6-10 aryloxy group, an unsubstituted or substituted heterocyclyloxy group, a substituted sulfonyloxy group, an amino group, an unsubstituted or substituted C1-6 alkyl amino group, an unsubstituted or substituted C3-8 cycloalkyl amino group, an unsubstituted or substituted C2-6 alkenyl amino group, an unsubstituted or substituted C2-6 alkynyl amino group, an unsubstituted or substituted C6-10 aryl amino group, an unsubstituted or substituted heterocyclyl amino group, an unsubstituted or substituted hydroxyamino group, an unsubstituted or substituted C1-7 acyl amino group, an unsubstituted or substituted C1-6 alkoxycarbonyl amino group, an unsubstituted or substituted C2-6 alkenyloxycarbonyl amino group, an unsubstituted or substituted C2-6 alkynyloxycarbonyl amino group, an unsubstituted or substituted C6-10 aryloxycarbonyl amino group, an unsubstituted or substituted heterocyclyloxycarbonyl amino group, a substituted sulfonyl amino group, an unsubstituted or substituted aminocarbonyl group, a mercapto group, an unsubstituted or substituted C1-6 alkyl thio group, an unsubstituted or substituted C3-8 cycloalkyl thio group, an unsubstituted or substituted C2-6 alkenyl thio group, an unsubstituted or substituted C2-6 alkynyl thio group, an unsubstituted or substituted C6-10 aryl thio group, an unsubstituted or substituted heterocyclyl thio group, (an unsubstituted or substituted C1-6 alkyl)thiocarbonyl group, (an unsubstituted or substituted C1-6 alkoxy)thiocarbonyl group, (an unsubstituted or substituted C1-6 alkyl thio)carbonyl group, (an unsubstituted or substituted C1-6 alkyl thio)thiocarbonyl group, a substituted sulfinyl group, a substituted sulfonyl group, pentafluorosulfanyl group, a tri C1-6 alkyl-substituted silyl group, a tri C6-10 aryl-substituted silyl group, a cyano group, nitro group or a halogen atom.

$R^{10}$ and $R^{11}$ of $Cy^1$ may independently form a ring, or bond together to form a ring, or bond with the atoms constituting $Cy^1$ to form a ring; $R^{20}$ and $R^{21}$ of $Cy^2$ may independently form a ring, or bond together to form a ring, or bond with the atoms constituting $Cy^2$ to form a ring.

m represents the number of $R^{10}$ and represents an integer of 0-5, preferably represents 1. When m is 2 or more, $R^{10}$s may be the same or different.

n represents the number of $R^{11}$ and represents an integer of 0-5, preferably represents 1. When n is 2 or more, $R^{11}$s may be the same or different.

p represents the number of $R^{20}$ and represents an integer of 0 to 5, preferably represents 1. When p is 2 or more, $R^{20}$s may be the same or different.

r represents the number of $R^{21}$ and represents an integer of 0 to 5, preferably represents 1. When r is 2 or more, $R^{21}$s may be the same or different.

Examples of the "unsubstituted or substituted C1-6 alkyl group" of $R^{10}$ or the like are the same as those listed as examples of $R^{1a}$ or the like.

In addition, other than the examples of $R^{1a}$ or the like, the examples of the "unsubstituted or substituted C1-6 alkyl group" also include a substituted C3-8 cycloalkoxy C1-6 alkyl group such as a chlorocyclohexyloxymethyl group, bromocyclohexyloxymethyl group, 2-methyl cyclopropyloxymethyl group, 2,3-dimethyl cyclopropyloxymethyl group, spiro[2.2]penta-1-yloxymethyl group, 1-methyl-spiro[2.2]penta-1-yloxymethyl group, 1-hydroxymethyl spiro[2.2]penta-1-yloxymethyl group, 4,4-difluoro-spiro[2.2]penta-1-yloxymethyl group, bicyclopropyl-2-yl group oxymethyl group or the like; a substituted C3-8 cycloalkyl C1-6 alkoxy C1-6 alkyl group such as a chlorocyclohexyl methoxymethyl group, bromocyclohexyl methoxymethyl group, 2-methyl cyclopropyl methoxymethyl group, 2,3-dimethyl cyclopropyl methoxymethyl group, spiro[2.2]penta-1-yl methoxymethyl group, 1-methyl-spiro[2.2]penta-1-yl methoxymethyl group, 1-hydroxymethyl spiro[2.2]penta-1-ylmethoxymethyl group, 4,4-difluoro-spiro[2.2]penta-1-ylmethoxymethyl group, bicyclopropyl-2-yl group methoxymethyl group or the like; or the like.

Examples of the "C3-8 cycloalkyl group" of $R^{10}$ include a cyclopropyl group, cyclobutyl group, cyclopentyl group, cyclohexyl group, cycloheptyl group or the like.

Examples of the "substituted C3-8 cycloalkyl group" include a chlorocyclohexyl group, bromocyclohexyl group, 2-methyl cyclopropyl group, 2,3-dimethyl cyclopropyl group, spiro[2.2]penta-1-yl group, 1-methyl-spiro[2.2]penta- 1-yl group, 1-hydroxymethyl spiro[2.2]penta-1-yl group, 4,4-difluoro-spiro[2.2]penta-1-yl group, bicyclopropyl-2-yl group or the like.

Examples of the "C2-6 alkenyl group" of $R^{10}$ or the like include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group or the like.

Examples of the "substituted C2-6 alkenyl group" of $R^{10}$ or the like include a C2-6 haloalkenyl group such as a 2-chloro-1-propenyl group, 2-fluoro-1-butenyl group or the like; or the like.

Examples of the "C2-6 alkynyl group" of $R^{10}$ or the like include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group or the like.

Examples of the "substituted C2-6 alkynyl group" of $R^{10}$ or the like include a C2-6 haloalkynyl group such as a 4,4-dichloro-1-butynyl group, 4-fluoro-1-pentynyl group, 5-bromo-2-pentynyl group or the like; or the like.

Examples of the "C1-6 alkoxy group" of $R^{10}$ or the like include a methoxy group, ethoxy group, n-propoxy group, i-propoxy group, n-butoxy group, i-butoxy group, s-butoxy group, t-butoxy group, n-pentyloxy group, i-pentyloxy group, 2-methyl butoxy group, neopentyl group, n-hexyloxy group or the like. Among these alkoxy groups, a C3-6 alkoxy group is preferable.

Examples of the "substituted C1-6 alkoxy group" of $R^{10}$ or the like include a C1-6 haloalkoxy group such as a fluoromethoxy group, chloromethoxy group, bromomethoxy group, difluoromethoxy group, dichloromethoxy group, dibromomethoxy group, trifluoromethoxy group, trichloromethoxy group, tribromomethoxy group, 2,2,2-trifluoroethoxy group, 2,2,2-trichloroethoxy group, pentafluoroethoxy group, 4-fluorobutoxy group, 3,3,3-trifluoropropoxy group, 2,2,2-trifluoro-1-trifluoromethyl ethoxy group, perfluorohexyloxy group or the like; a hydroxy C1-6 alkoxy group such as a 2-hydroxyethoxy group, 2-hydroxypropoxy group or the like; a C1-6 alkoxy C1-6 alkoxy group such as a methoxymethoxy group, 1-methoxyethoxy group, 2-methoxyethoxy group, ethoxymethoxy group, 1-ethoxyethoxy group, 2-ethoxyethoxy group, 1-methoxy-n-propoxy group, 2-methoxy-n-propoxy group, 3-methoxy-n-propoxy group or the like; a C3-8 cycloalkyl C1-6 alkoxy group such as a cyclopropyl methoxy group, cyclobutyl methoxy group, cyclopentyl methoxy group, cyclohexyl methoxy group, 2-methyl cyclopropyl methoxy group, 2,3-dimethyl cyclopropyl methoxy group, 2-cyclopropyl ethoxy group or the like; a C7-11 aralkyloxy group such as a benzyloxy group, phenethyloxy group or the like; a C1-7 acyl C1-6 alkoxy group such as an acetyl methoxy group, 2-acetyl ethoxy group or the like; a cyano C1-6 alkoxy group such as a cyanomethoxy group, 2-cyanoethoxy group or the like; a substituted C3-8 cycloalkyl C1-6 alkoxy group such as a chlorocyclohexyl methoxy group, bromocyclohexyl methoxy group, 2-methyl cyclopropyl methoxy group, 2,3-dimethyl cyclopropyl methoxy group, spiro[2.2]penta-1-yl methoxy group, 1-methyl-spiro[2.2]penta-1-yl methoxy group, 1-hydroxymethyl spiro[2.2]penta-1-yl methoxy group, 4,4-difluoro-spiro[2.2]penta-1-yl methoxy group, bicyclopropyl-2-yl group methoxy or the like; or the like.

Examples of the "C3-8 cycloalkoxy group" of $R^{10}$ or the like include a cyclopropyloxy group, cyclobutyloxy group, cyclopentyloxy group, cyclohexyloxy group, cycloheptyloxy group or the like.

Examples of the "substituted C3-8 cycloalkyloxy group" of $R^{10}$ or the like include a chlorocyclohexyloxy group, bromocyclohexyloxy group, 2-methyl cyclopropyloxy group, 2,3-dimethyl cyclopropyloxy group, spiro[2.2]penta-1-yloxy group, 1-methyl-spiro[2.2]penta-1-yloxy group, 1-hydroxymethyl spiro[2.2]penta-1-yloxy group, 4,4-difluoro-spiro[2.2]penta-1-yloxy group, bicyclopropyl-2-yloxy group or the like.

Examples of the "C2-6 alkenyloxy group" of $R^{10}$ or the like include a vinyloxy group, 1-propenyloxy group, 2-propenyloxy group, 1-butenyloxy group, 2-butenyloxy group, 3-butenyloxy group, 1-methyl-2-propenyloxy group, 2-methyl-2-propenyloxy group, 1-pentenyloxy group, 2-pentenyloxy group, 1-methyl-2-butenyloxy group, 2-methyl-2-butenyloxy group, 3-methyl-2-butenyloxy group, 1-hexenyloxy group, 2-hexenyloxy group or the like.

Examples of the "substituted C2-6 alkenyloxy group" of $R^{10}$ or the like include a C2-6 haloalkenyloxy group such as a 2-chloro-1-propenyloxy group, 3,3-dichloro-2-propenyloxy group, 2-fluoro-1-butenyloxy group or the like; or the like.

Examples of the "C2-6 alkynyloxy group" of $R^{10}$ or the like include an ethynyloxy group, 1-propynyloxy group, 2-propynyloxy group, 1-butynyloxy group, 2-butynyloxy group, 3-butynyloxy group, 1-methyl-2-propynyloxy group, 2-methyl-3-butynyloxy group, 1-pentynyloxy group, 2-pentynyloxy group, 1-methyl-2-butynyloxy group, 2-methyl-3-pentynyloxy group, 1-hexynyloxy group or the like.

Examples of the "substituted C2-6 alkynyloxy group" of $R^{10}$ or the like include a C2-6 haloalkynyloxy group such as a 4,4-dichloro-1-butynyloxy group, 4-fluoro-1-pentynyloxy group, 5-bromo-2-pentynyloxy group or the like; or the like.

Examples of the "C1-7 acyl group" of $R^{10}$ or the like include a formyl group, acetyl group, propionyl group, benzoyl group or the like.

Examples of the "substituted C1-7 acyl group" of $R^{10}$ or the like include a halogen-substituted C1-7 acyl group such as a chloroacetyl group, trifluoroacetyl group, trichloroacetyl group, 4-chlorobenzoyl group or the like;

Examples of the "C1-6 alkoxycarbonyl group" of $R^{10}$ or the like include a methoxycarbonyl group, ethoxycarbonyl group, n-propoxycarbonyl group, i-propoxycarbonyl group or the like.

Examples of the "substituted C1-6 alkoxycarbonyl group" of $R^{10}$ or the like include a C3-8 cycloalkyl C1-6 alkoxycarbonyl group such as a cyclopropyl methoxycarbonyl group, cyclobutyl methoxycarbonyl group, cyclopentyl methoxycarbonyl group, cyclohexyl methoxycarbonyl group, 2-methyl cyclopropyl methoxycarbonyl group, 2,3-dimethyl cyclopropyl methoxycarbonyl group, 2-chlorocyclopropyl methoxycarbonyl group, 2-cyclopropyl ethoxycarbonyl group or the like; a C1-6 haloalkoxycarbonyl group such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group, 2,2,2-trichloroethoxycarbonyl group, pentafluoroethoxycarbonyl group, 4-fluorobutoxycarbonyl group, 3,3,3-trifluoropropoxycarbonyl group, 2,2,2-trifluoro-1-trifluoromethyl ethoxycarbonyl group, perfluorohexyloxycarbonyl group or the like; a C6-10 aryl C1-6 alkyloxycarbonyl group such as a benzyloxycarbonyl group, 1-phenyl ethoxycarbonyl group or the like; a heterocyclyl C1-6 alkoxycarbonyl group such as a tetrahydrofuran-2-yl methoxycarbonyl group, pyrazolyl methoxycarbonyl group, thiadiazolyl methoxycarbonyl group, pyridyl methoxycarbonyl group, pyrimidinyl methoxycarbonyl group, pyridazinyl methoxycarbonyl group or the like;

Examples of the "C3-8 cycloalkyloxycarbonyl group" of $R^{10}$ or the like include a cyclopropyloxycarbonyl group, cyclobutoxycarbonyl group or the like.

Examples of the "C2-6 alkenyloxycarbonyl group" of $R^{10}$ or the like include an ethenyloxycarbonyl group, 2-propenyloxycarbonyl group, 1-propenyloxycarbonyl group or the like.

Examples of the "substituted C2-6 alkenyloxycarbonyl group" of $R^{10}$ or the like include a 1-methyl-2-propenyloxycarbonyl group, 2-methyl-1-propenyloxycarbonyl group or the like.

Examples of the "C2-6 alkynyloxycarbonyl group" of $R^{10}$ or the like include an ethynyloxycarbonyl group, propargyloxycarbonyl group, 2-butynyloxycarbonyl group or the like.

Examples of the "substituted C2-6 alkynyloxycarbonyl group" of $R^{10}$ or the like include a 1-methyl propargyloxycarbonyl group or the like.

Examples of the "C6-10 aryloxycarbonyl group" of $R^{10}$ or the like include a phenyloxycarbonyl group, naphthoxycarbonyl group or the like.

Examples of the "heterocyclyloxycarbonyl group" of $R^{10}$ or the like include a pyridyloxycarbonyl group, pyridazinyloxycarbonyl group or the like.

Examples of the "C1-7 acyloxy group" of $R^{10}$ or the like include a formyloxy group, acetyloxy group, propionyloxy group or the like.

Examples of the "substituted C1-7 acyloxy group" of $R^{10}$ or the like include a halogen-substituted C1-7 acyloxy group such as a chloroacetyloxy group, trifluoroacetyloxy group, trichloroacetyloxy group, 4-chlorobenzoyloxy group; or the like; or the like.

Examples of the "C1-6 alkoxycarbonyloxy group" of $R^{10}$ or the like include a methoxycarbonyloxy group, ethoxycarbonyloxy group, i-propoxycarbonyloxy group or the like.

Examples of the "C3-8 cycloalkyloxycarbonyloxy group" of $R^{10}$ or the like include a cyclopropyloxycarbonyloxy group, cyclobutyloxycarbonyloxy group, cyclopentyloxycarbonyloxy group, cyclohexyloxycarbonyloxy group or the like.

Examples of the "C2-6 alkenyloxycarbonyloxy group" of $R^{10}$ or the like include a vinyloxycarbonyloxy group, 1-propenyloxycarbonyloxy group, 2-propenyloxycarbonyloxy group, 1-butenyloxycarbonyloxy group, 2-butenyloxycarbonyloxy group, 3-butenyloxycarbonyloxy group, 1-methyl-2-propenyloxycarbonyloxy group or the like.

Examples of the "C2-6 alkynyloxycarbonyloxy group" of $R^{10}$ or the like include an ethynyloxycarbonyloxy group, 1-propynyloxycarbonyloxy group, 2-propynyloxycarbonyloxy group, 1-butynyloxycarbonyloxy group, 2-butynyloxycarbonyloxy group, 3-butynyloxycarbonyloxy group or the like.

Examples of the "C1-6 alkyl aminocarbonyloxy group of $R^{10}$ or the like include a methyl aminocarbonyloxy group, dimethyl aminocarbonyloxy group, diethyl aminocarbonyloxy group, i-propyl aminocarbonyloxy group, i-butyl aminocarbonyloxy group or the like.

Examples of the "C3-8 cycloalkyl aminocarbonyloxy group" of $R^{10}$ or the like include a cyclopropyl aminocarbonyloxy group, cyclobutyl aminocarbonyloxy group, cyclopentyl aminocarbonyloxy group, cyclohexyl aminocarbonyloxy group or the like.

Examples of the "C2-6 alkenyl aminocarbonyloxy group" of $R^{10}$ or the like include a vinyl aminocarbonyloxy group, 1-propenyl aminocarbonyloxy group, 2-propenyl aminocarbonyloxy group, 1-butenyl aminocarbonyloxy group or the like.

Examples of the "C2-6 alkynyl aminocarbonyloxy group" of $R^{10}$ or the like include an ethynyl aminocarbonyloxy group, 1-propynyl aminocarbonyloxy group, 2-propynyl aminocarbonyloxy group, 1-butynyl aminocarbonyloxy group or the like.

Examples of the "C6-10 aryl aminocarbonyloxy group" of $R^{10}$ or the like include an anilinocarbonyloxy group, naphthyl aminocarbonyloxy group or the like.

Examples of the "heterocyclyl aminocarbonyloxy group" of $R^{10}$ or the like include a pyridyl aminocarbonyloxy group, pyridazinyl aminocarbonyloxy group or the like.

Examples of the "substituted aminooxy group" of $R^{10}$ or the like include a C1-6 alkyl aminooxy group such as a methyl aminooxy group, ethyl aminooxy group or the like; a C1-7 acyl aminooxy group such as a formyl aminooxy group, acetyl aminooxy group or the like; or the like.

Examples of the "C1-6 alkylidene aminooxy group" of $R^{10}$ or the like include a methylidene aminooxy group, ethylidene aminooxy group, n-propylidene aminooxy group, i-propylidene aminooxy group, n-butylidene aminooxy group, i-butylidene aminooxy group, s-butylidene aminooxy group or the like.

Examples of the "C6-10 aryl group" of $R^{10}$ or the like are the same as those listed as the examples of $Cy^1$ or the like.

Examples of the "heterocyclyl group" of $R^{10}$ or the like are the same as those listed as examples of $Cy^1$ or the like.

Examples of the "C6-10 aryloxy group" of $R^{10}$ or the like include a phenoxy group, naphthoxy group or the like.

Examples of the "heterocyclyloxy group" of $R^{10}$ or the like include a pyridyloxy group, pyridazinyloxy group or the like.

Examples of the "substituted sulfonyloxy group" of $R^{10}$ or the like include a C1-6 alkyl sulfonyloxy group such as a methyl sulfonyloxy group, ethyl sulfonyloxy group or the like; a C1-6 haloalkyl sulfonyloxy group such as a trifluoromethyl sulfonyloxy group, 2,2,2-trifluoroethyl sulfonyloxy group or the like; a C6-10 aryl sulfonyloxy group such as a phenyl sulfonyloxy group or the like; or the like.

Examples of the "C1-6 alkyl amino group" of $R^{10}$ or the like include a methyl amino group, dimethyl amino group, diethyl amino group, i-butyl amino group or the like.

Examples of the "C3-8 cycloalkyl amino group" of $R^{10}$ or the like include a cyclopropyl amino group, cyclobutyl amino group, cyclopentyl amino group, cyclohexyl amino group or the like.

Examples of the "C2-6 alkenyl amino group" of $R^{10}$ or the like include a vinyl amino group, 1-propenyl amino group, 2-propenyl amino group, 1-butenyl amino group or the like.

Examples of the "C2-6 alkynyl amino group" of $R^{10}$ or the like include an ethynyl amino group, 1-propynyl amino group, 2-propynyl amino group, 1-butynyl amino group or the like.

Examples of the "C6-10 aryl amino group" of $R^{10}$ or the like include an anilino group, naphthyl amino group or the like.

Examples of the "heterocyclyl amino group" of $R^{10}$ or the like include a pyridyl amino group, pyridazinyl amino group or the like.

Examples of the "substituted hydroxyamino group" of $R^{10}$ or the like include a C1-6 alkoxyamino group such as a methoxyamino group, ethoxyamino group or the like; a C1-7 acyloxyamino group such as an acetoxyamino group, propionyloxyamino group or the like; or the like.

Examples of the "C1-7 acyl amino group" of $R^{10}$ or the like include a formyl amino group, acetyl amino group, propanoyl amino group, butyryl amino group, i-propyl carbonyl amino group, benzoyl amino group or the like.

Examples of the "C1-6 alkoxycarbonyl amino group" of $R^{10}$ or the like include a methoxycarbonyl amino group, ethoxycarbonyl amino group, n-propoxycarbonyl amino group, i-propoxycarbonyl amino group or the like.

Examples of the "C2-6 alkenyloxycarbonyl amino group" of $R^{10}$ or the like include a vinyl aminocarbonyl amino group, 1-propenyl aminocarbonyl amino group, 2-propenyl aminocarbonyl amino group, 1-butenyl aminocarbonyl amino group or the like.

Examples of the "C2-6 alkynyloxycarbonyl amino group" of $R^{10}$ or the like include an ethynyl aminocarbonyl amino group, 1-propynyl aminocarbonyl amino group, 2-propynyl aminocarbonyl amino group, 1-butynyl aminocarbonyl amino group or the like.

Examples of the "C6-10 aryloxycarbonyl amino group" of $R^{10}$ or the like include an anilinocarbonyl amino group, naphthyl aminocarbonyl amino group or the like.

Examples of the "heterocyclyloxycarbonyl amino group" of $R^{10}$ or the like include a pyridyl aminocarbonyl amino group, pyridazinyl aminocarbonyl amino group or the like.

Examples of the "substituted sulfonyl amino group" of $R^{10}$ or the like include a C1-6 alkyl sulfonyl amino group such as a methyl sulfonyloxy group, ethyl sulfonyl amino group or the like; a C1-6 haloalkyl sulfonyl amino group such as a trifluoromethyl sulfonyl amino group, 2,2,2-trifluoroethyl sulfonyl amino group or the like; a C6-10 aryl sulfonyl amino group such as a phenyl sulfonyl amino group or the like; or the like.

Examples of the "substituted aminocarbonyl group" of $R^{10}$ or the like include a dimethyl aminocarbonyl group, phenyl aminocarbonyl group, N-phenyl-N-methyl aminocarbonyl group or the like.

Examples of the "C1-6 alkyl thio group" of $R^{10}$ or the like include a methyl thio group, ethyl thio group, n-propyl thio group, i-propyl thio group, n-butyl thio group, i-butyl thio group, s-butyl thio group, t-butyl thio group or the like.

Examples of the "C3-8 cycloalkyl thio group" of $R^{10}$ or the like include a cyclopropyl thio group, cyclobutyl thio group, cyclopentyl thio group, cyclohexyl thio group, cycloheptyl thio group or the like.

Examples of the "C2-6 alkenyl thio group" of $R^{10}$ or the like include a vinyl thio group, 1-propenyl thio group, 2-propenyl thio group, 1-butenyl thio group, 2-butenyl thio group, 3-butenyl thio group or the like.

Examples of the "C2-6 alkynyl thio group" of $R^{10}$ or the like include an ethynyl thio group, 1-propynyl thio group, 2-propynyl thio group, 1-butynyl thio group, 2-butynyl thio group, 3-butynyl thio group or the like.

Examples of the "C6-10 aryl thio group" of $R^{10}$ or the like include a phenyl thio group, naphthyl thio group or the like.

Examples of the "heterocyclyl thio group" of $R^{10}$ or the like include a pyridyl thio group, pyridazinyl thio group or the like.

Examples of the "(C1-6 alkyl)thiocarbonyl group" of $R^{10}$ or the like include a methyl(thiocarbonyl) group, ethyl(thiocarbonyl) group, n-propyl(thiocarbonyl) group, i-propyl(thiocarbonyl) group, n-butyl(thiocarbonyl) group, i-butyl(thiocarbonyl) group, s-butyl(thiocarbonyl) group, t-butyl(thiocarbonyl) group or the like.

Examples of the "(C1-6 alkoxy)thiocarbonyl group" of $R^{10}$ or the like include a methoxy(thiocarbonyl) group, ethoxy(thiocarbonyl) group, n-propoxy(thiocarbonyl) group, i-propoxy(thiocarbonyl) group, n-butoxy(thiocarbonyl) group, i-butoxy(thiocarbonyl) group, s-butoxy(thiocarbonyl) group, t-butoxy(thiocarbonyl) group or the like.

Examples of the "(C1-6 alkyl thio)carbonyl group" of $R^{10}$ or the like include a (methyl thio)carbonyl group, (ethyl thio)carbonyl group, (n-propyl thio)carbonyl group, (i-propyl thio)carbonyl group, (n-butyl thio)carbonyl group, (i-butyl thio)carbonyl group, (s-butyl thio)carbonyl group, (t-butyl thio)carbonyl group or the like.

Examples of the "(C1-6 alkyl thio)thiocarbonyl group" of $R^{10}$ or the like include a (methyl thio)thiocarbonyl group, (ethyl thio)thiocarbonyl group, (n-propyl thio)thiocarbonyl group, (i-propyl thio)thiocarbonyl group, (n-butyl thio)thiocarbonyl group, (i-butyl thio)thiocarbonyl group, (s-butyl thio)thiocarbonyl group, (t-butyl thio)thiocarbonyl group or the like.

Examples of the "substituted sulfinyl group" of $R^{10}$ or the like include a C1-6 alkyl sulfinyl group such as a methyl sulfinyl group, ethyl sulfinyl group or the like; a C1-6 haloalkyl sulfinyl group such as a trifluoromethyl sulfinyl group, 2,2,2-trifluoroethyl sulfinyl group or the like; a C6-10 aryl sulfinyl group such as a phenyl sulfinyl group or the like; or the like.

Examples of the "substituted sulfonyl group" of $R^{10}$ or the like include a C1-6 alkyl sulfonyl group such as a methyl sulfonyl group, ethyl sulfonyl group or the like; a C1-6 haloalkyl sulfonyl group such as a trifluoromethyl sulfonyl group, 2,2,2-trifluoroethyl sulfonyl group or the like; a C6-10 aryl sulfonyl group such as a phenyl sulfonyl group or the like; a C1-6 alkoxysulfonyl group such as a methoxysulfonyl group, ethoxysulfonyl group or the like; or the like.

Examples of the "tri C1-6 alkyl-substituted silyl group" of $R^{10}$ or the like include a trimethyl silyl group, triethyl silyl group, t-butyl dimethyl silyl group or the like.

Examples of the "tri C6-10 aryl-substituted silyl group" of $R^{10}$ or the like include a triphenyl silyl group or the like.

Examples of the "halogen atom" of $R^{10}$ or the like include a chlorine atom, bromine atom, fluorine atom, iodine atom or the like.

$R^{10}$ and $R^{11}$ of $Cy^1$ may independently form a ring, or bond together to form a ring, or bond with the atoms constituting $Cy^1$ to form a ring; $R^{20}$ and $R^{21}$ of $Cy^2$ may independently form a ring, or bond together to form a ring, or may bond with the atoms constituting $Cy^2$ to form a ring.

Examples of the ring that may be formed include an aromatic hydrocarbon ring such as a benzene ring or the like; a C5-7 cycloalkene ring such as a cyclopentene ring, cyclohexene ring, cycloheptene ring or the like; a 5- to 7-membered aromatic heteroring such as a furan ring, thiophene ring, pyrrole ring, imidazole ring, pyrazole ring, thiazole ring, oxazole ring, isoxazole ring, pyridine ring, pyrazine ring, pyrimidine ring, pyridazine ring, azepine ring, diazepine ring or the like; an unsaturated 5- to 7-membered heteroring such as a dihydro-2H-pyran ring, dihydro-2H-thiopyran ring, tetrahydropyridine ring or the like; or the like.

These rings may have substituents on the rings.

Examples of the substituents include a halogen atom such as a fluorine atom, chlorine atom, bromine atom, iodine atom or the like; a C1-6 alkyl group such as a methyl group, ethyl group, n-propyl group, i-propyl group, n-butyl group, s-butyl group, i-butyl group, t-butyl group, n-pentyl group, n-hexyl group or the like; a C3-6 cycloalkyl group such as a cyclopropyl group, cyclobutyl group, cyclopentyl group, cyclohexyl group or the like; a C1-6 alkoxy group such as a methoxy group, ethoxy group, n-propoxy group, i-propoxy group, n-butoxy group, s-butoxy group, i-butoxy group, t-butoxy group or the like; a hydroxy group; a C1-6 haloalkyl group such as a chloromethyl group, chloroethyl group, trifluoromethyl group, 1,2-dichloro-n-propyl group, 1-fluoro-n-butyl group, perfluoro-n-pentyl group or the like; or the like.

In formula (I), $R^{10}$ preferably represents a C1-6 alkyl group, a C1-6 alkoxy C1-6 alkyl group, a C1-6 alkoxy C1-6 alkoxy C1-6 alkyl group, a C2-6 alkenyl group, a hydroxy group, a C1-6 alkoxy group, a C1-6 haloalkoxy group, a C3-8 cycloalkoxy group, a C2-6 alkenyloxy group, a C2-6 haloalkenyloxy group, a C2-6 alkynyloxy group, a C2-6 haloalkynyloxy group, a C1-6 alkoxy C1-6 alkoxy group, a C3-8 cycloalkyl C1-6 alkoxy group, a cyano C1-6 alkoxy group, a C1-7 acyl C1-6 alkoxy group, a hydroxy C1-6 alkoxy group, a C1-7 acyloxy group, a C1-6 alkoxycarbonyl group, a C2-6 alkenyloxycarbonyl group, a C2-6 alkynyloxycarbonyl group, a C1-6 alkoxycarbonyloxy group, a C1-6 alkyl aminocarbonyloxy group, a C6-10 aryl group, a heterocyclyl group, a C1-6 haloalkyl sulfonyloxy group, a C1-6 alkylidene aminooxy group, a C1-6 alkoxycarbonyl amino group, an unsubstituted or substituted C7-11 aralkyl group, an unsubstituted or substituted C7-11 aralkyloxy group, a C1-6 alkyl thio group, or a nitro group.

In formula (I), $R^{11}$ preferably represents a cyano group, a halogen atom, pentafluorosulfanyl group, a C1-6 haloalkyl group, a C2-6 haloalkenyl group, or a C2-6 haloalkynyl group.

In formula (I), $R^{20}$ preferably represents a cyano group, a halogen atom, a pentafluorosulfanyl group, a C1-6 haloalkyl group, a C2-6 haloalkenyl group, or a C2-6 haloalkynyl group.

In formula (I), $R^{21}$ preferably represents a C1-6 alkyl group, a C1-6 alkoxy C1-6 alkyl group, a C1-6 alkoxy C1-6 alkoxy C1-6 alkyl group, a hydroxy group, a C1-6 alkoxy group, a C1-6 haloalkoxy group, a C2-6 haloalkenyloxy group, a C2-6 haloalkynyloxy group, a C1-6 alkoxy C1-6 alkoxy group, a C3-8 cycloalkyl C1-6 alkoxy group, a C1-6 alkoxycarbonyl group, a C2-6 alkenyloxycarbonyl group, a C2-6 alkynyloxycarbonyl group, a C1-6 alkylidene aminooxy group, a C1-6 alkoxycarbonyl amino group, an unsubstituted or substituted C7-11 aralkyl group, an unsubstituted or substituted C7-11 aralkyloxy group, or a nitro group.

In formula (I), Y represents an oxygen atom or a sulfur atom.

[Chemical formula 8]

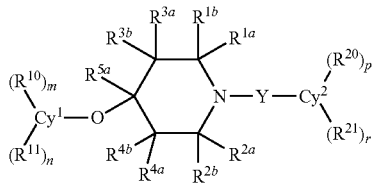

(I)

In the cyclic amine compound of the present invention, it is preferable that $Cy^1$ is a phenyl group, $Cy^2$ is a pyridine-2-yl group, $R^{1b}$, $R^{2b}$, $R^{3a}$, $R^{3b}$, $R^{4a}$, $R^{4b}$, and $R^{5a}$ are a hydrogen atom, $R^{1a}$ and $R^{2a}$ bond together to form an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$—, or a group represented by formula: —CH$_2$NR$^6$CH$_2$— (provided that $R^6$ is a hydrogen atom, an unsubstituted or substituted C1-6 alkyl group, an unsubstituted or substituted C1-7 acyl group, or an unsubstituted or substituted C1-6 alkoxycarbonyl group), Y is an oxygen atom, r is 0, and p is an integer of 0 to 4. Namely, the cyclic amine compound of the present invention is preferably a cyclic amine compound represented by formula (II).

[Chemical formula 9]

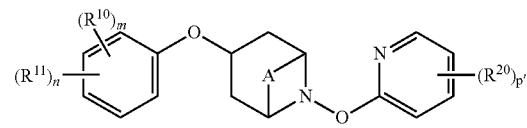

(II)

In addition, $R^{10}$, m, $R^{11}$, n and $R^{20}$ of formula (II) are the same as previously defined in formula (I). In formula (II), p' represents the number of $R^{20}$ and represents an integer of 0 to 4. When p' is 2 or more, $R^{20}$s may be the same or different. In formula (II), A represents an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$— or a group represented by formula: —CH$_2$NR$^6$CH$_2$— (provided that $R^6$ represents a hydrogen atom, an unsubstituted or substituted C1-6 alkyl group, an unsubstituted or substituted C1-7 acyl group, or an unsubstituted or substituted C1-6 alkoxycarbonyl group).

[Salt of Cyclic Amine Compound]

There are no particular limitations on the salts of the cyclic amine compound of the present invention provided it is an agriculturally and horticulturally allowable salt. Examples of the salt include salts of inorganic acids such as hydrochloric acid or sulfuric acid; salts of organic acids such as acetic acid or lactic acid; salts of alkaline metals such as lithium, sodium or potassium; salts of alkaline earth metals such as calcium or magnesium; salts of transition metals such as iron or copper; and salts of organic bases such as ammonia, triethylamine, tributylamine, pyridine or hydrazine. The salt of cyclic amine compound of the present invention may be produced by a well-known method using the cyclic amine compound represented by formula (I) or (II).

[Production Method]

There are no particular limitations on the production method of the cyclic amine compound or salt thereof.

First, a production method of a hydroxylamine compound of the present invention, wherein Y is an oxygen atom will be explained. When Y is an oxygen atom, a production method that goes through a compound represented by the following formula (3) as an intermediate is preferable.

[Chemical formula 10]

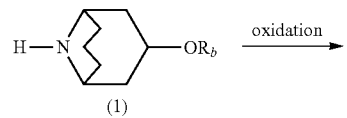

(1)

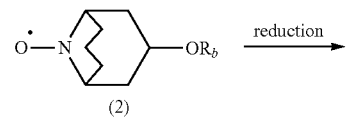

(2)

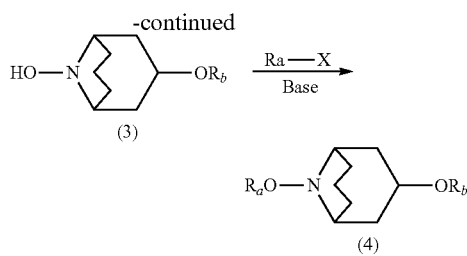

First, a secondary amine compound represented by formula (I) (hereafter, may be referred to as "compound (1)") is prepared. An aminoxyl compound represented by formula (2) (hereafter, may be referred to as "compound (2)") can then be synthesized by oxidizing the compound (1) with a suitable oxidizing agent. Specific examples of the oxidation reaction method include a method in which an oxidizing agent such as hydrogen peroxide, sodium hypochlorite or an organic oxidizing agent are allowed to act in a suitable solvent such as an anhydrous or hydrous alcohol such as methanol, ethanol, propanol or isopropanol, an ether such as dioxane or tetrahydrofuran (THF) or acetonitrile, and a method in which a tungstate-hydrogen peroxide urea complex is allowed to act. In addition, another example of a method that can be used includes blowing a gas containing oxygen or active oxygen such as ozone into a reaction mixture.

Next, the aminoxyl group is converted to a hydroxyamino group by reducing compound (2) under suitable conditions. A hydroxyamine compound represented by formula (3) (hereafter, may be referred to as "compound (3)") is formed by this reduction reaction.

Following the reduction reaction, a heterocyclyl halide is reacted with compound (3) in the presence of a base. As a result, a heterocyclyloxyamine compound represented by formula (4) can be obtained. This reaction is described in, for example, U.S. Pat. No. 5,286,865.

Furthermore, in the aforementioned formulas (1) to (4), $R_b$ represents a substituted phenyl group, $R_a$ represents a substituted heterocyclyl group, and X represents a halogen atom.

In addition, compound (3) can also be obtained by, for example, the production method indicated below.

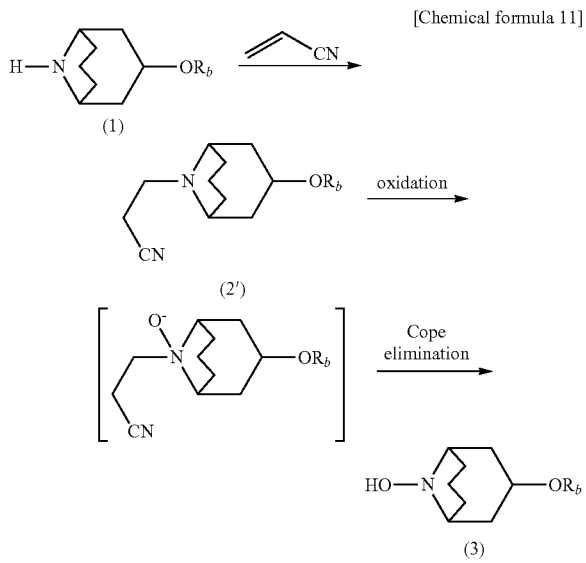

An alkylamino compound represented by formula (2') (hereafter, may be referred to as "compound (2')") is obtained by N-alkylating the aforementioned compound (1) with acrylonitrile. Continuing, compound (3) can be obtained by oxidizing with a suitable oxidizing agent to obtain an N-oxide form within the reaction system and then subjecting this to a Cope elimination reaction. This reaction is described in, for example, Tetrahedron Letters, 48 (2007), pp. 1683-1686.

On the other hand, a compound of the present invention, wherein Y is a sulfur atom may be produced by the following production method.

[Chemical formula 12]

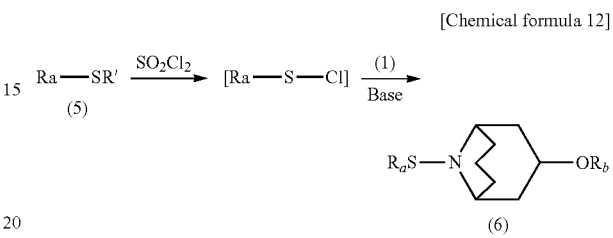

First, a sulfenyl compound represented by formula (5) (hereafter, may be referred to as "compound (5)") (in the formula, R' represents a hydrogen atom or a benzyl group) is prepared. Then, sulfuryl chloride is added and reacted with the compound (5) to obtain a sulfenyl chloride compound, followed by reacting compound (1) in the presence of a base to obtain a heterocyclylthioxyamine compound represented by formula (6). The production method of sulfenyl chloride compound is described in Synthesis 1994; volume 1994 (1): 21-22 or the like.

[Hydroxyamine Compound]

The hydroxyamine compound according to the present invention is a compound represented by formula (III). In addition, a salt of the hydroxyamine compound according to the present invention is a salt of a compound represented by formula (III). A compound represented by formula (III) or a salt thereof is preferable as a production intermediate of a compound represented by formula (I) or formula (II) or a salt thereof In formula (III), $Cy^1$, $R^{10}$, $R^{11}$, m, n, $R^{1a}$, $R^{1b}$, $R^{2a}$, $R^{2b}$, $R^{3a}$, $R^{3b}$, $R^{4a}$, $R^{4b}$ and $R^{5a}$ are the same as previously defined in formula (I).

In formula (III), $R^{1a}$ and $R^{2a}$, or $R^{3a}$ and $R^{4a}$ bond together to form an unsubstituted or substituted C3-6 alkylene group, an unsubstituted or substituted C3-6 alkenylene group, a group represented by formula: —$CH_2OCH_2$—, a group represented by formula: —$CH_2SCH_2$—, a group represented by formula: —$CH_2C(=O)CH_2$—, or a group represented by formula: —$CH_2NR^6CH_2$— (provided that $R^6$ represents a hydrogen atom, an unsubstituted or substituted C1-6 alkyl group, an unsubstituted or substituted C1-7 acyl group, or an unsubstituted or substituted C1-6 alkoxycarbonyl group). Examples of these divalent organic groups are the same as previously defined in formula (I).

In formula (III), $Cy^1$ is preferably a phenyl group, a pyrazolyl group, a thiadiazolyl group, a pyridyl group, a pyrimidinyl group or a pyridazinyl group.

In formula (III), $R^{10}$ preferably represents a C1-6 alkyl group, a C1-6 alkoxy C1-6 alkyl group, a C1-6 alkoxy C1-6 alkoxy C1-6 alkyl group, a C2-6 alkenyl group, a hydroxy group, a C1-6 alkoxy group, a C1-6 haloalkoxy group, a C3-8 cycloalkoxy group, a C2-6 alkenyloxy group, a C2-6 haloalkenyloxy group, a C2-6 alkynyloxy group, a C2-6 haloalkynyloxy group, a C1-6 alkoxy C1-6 alkoxy group, a C3-8 cycloalkyl C1-6 alkoxy group, a cyano C1-6 alkoxy group, a C1-7 acyl C1-6 alkoxy group, a hydroxy C1-6 alkoxy group, a C1-7 acyloxy group, a C1-6 alkoxycarbonyl group, a C2-6 alkenyloxycarbonyl group, a C2-6 alkynyloxycarbonyl group, a C1-6 alkoxycarbonyloxy group, a C1-6 alkyl aminocarbonyloxy group, a C6-10 aryl group, a heterocyclyl group, a C1-6 haloalkyl sulfonyloxy group, a C1-6 alkylidene aminooxy group, a C1-6 alkoxycarbonyl amino group, an unsubstituted or substituted C7-11 aralkyl group, an unsubstituted or substituted C7-11 aralkyloxy group, a C1-6 alkyl thio group, or a nitro group.

In formula (III), $R^{11}$ preferably represents a cyano group, a halogen atom, a pentafluorosulfanyl group, a C1-6 haloalkyl group, a C2-6 haloalkenyl group, or a C2-6 haloalkynyl group.

There are no particular limitations on the salt of the hydroxyamine compound according to the present invention provided it does not inhibit the reaction with heterocyclyl halide in the presence of base. Examples of the salts include alkaline metal salts such as lithium salts, sodium salts or potassium salts. A salt of the hydroxyamine compound according to the present invention can be obtained by a well-known method using a hydroxyamine compound represented by formula (III).

Since the cyclic amine compound of the present invention, or salt thereof, demonstrates insecticidal action on adult insects, immature insects, larvae, insect eggs and the like, it can be used to control harmful organisms such as harmful insects present on agricultural crops, mites, ticks, sanitarily harmful insects, stored grain harmful insects, clothing harmful insects and household harmful insects.

Examples of the insects include the following:

lepidopteran pests such as, for example, *Spodoptera litura, Mamestra brassicae, agrotis ipsilon*, green caterpillars, *Autographa nigrisigna, Plutella xylostella, Adoxophyes honmai, Homona magnanima, Carposina sasakii, Grapholita molesta, Phyllocnistis citrella, Caloptilia theivora, Phyllonorycter ringoniella, Lymantria dispar, Euproctis pseudoconspersa, Chilo suppressalis, Cnaphalocrocis medinalis, Ostrinia nubilasis, Hyphantria cunea, Cadra cautella*, genus *Heliothis*, genus *Helicoverpa*, genus *Agrothis, Tinea translucens, Cydia pomonella*, and *Pectinophora gossypiella;* hemipteran pests such as, for example, *Myzus persicae, Aphis gossypii, Lipaphis erysimi, Rhopalosiphum padi, Riptortus clavatus, Nezara antennata, Unaspis yanonensis, Pseudococcus comstocki, Trialeurodes vaporariorum, Bemisia tabaci, Bemisia argentifolii, Psylla pyrisuga, Stephanitis nashi, Nilaparuata lugens, Laodelphax stratella, Sogatella furcifera*, and *Nephotettix cincticeps;* coleopteran pests such as, for example, *Phyllotreta striolata, Aulacophora femoralis, Leptinotarsa decemlineata, Lissorhoptrus oryzophilus, Sitophilis zeamais, Callosobruchus chinensis, Popillia japonica, Anomala rufocuprea*, genus *Diabrotica, Lasioderma serricorne, Lyctus brunneus, Monochamus alternatus, Anoplophora malasiaca*, genus *Agriotis, Epilachna vigintioctopunctata, Tenebroides mauritanicus*, and *Anthonomus grandis;* dipteran pests such as, for example, *Musca domestica, Calliphora lata, Boettcherisca peregrine, Zeugodacus cucurbitae, Bactrocera dorsalis, Delia platura, Agromyza oryzae, Drosophila melanogaster, Stomoxys calcitrans, Culex tritaeniorhynchus, Aedes aegypti*, and *Anopheles sinensis;* thysanopteran pests such as, for example, *Thrips palmi*, and *Scirtothrips dorsalis;* hymenopteran pests such as, for example, *Monomorium pharaonis, Vespa simillima xanthoptera*, and *Athalia rosae ruficornis;* orthopteran pests such as, for example, *Locusta migratoria, Blattella germanica, Periplaneta americana*, and *Periplaneta fuliginosa;* isopteran pests such as, for example, *Coptotermes formosanus* and *Reticulitermes speratus;* siphonapteran pests such as, for example, *Pulex irritans* and *Ctenocephalides felis;* phthirapteran pests such as, for example, *Pediculus humanus;* plant parasitic nematodes such as *Meloidogyne incognita, Pratylenchus* spp., *Heterodera glycines, Aphelenchoides besseyi*, and *Bursaphelenchus xylophilus;* and acarina.

Among these insects, the cyclic amine compound of the present invention or salt thereof is useful as an active ingredient of an acaricide since it is particularly effective in controlling acari.

Examples of acari targeted for control are indicated below:

acari belonging to the Tetranychidae family, including *Brevipalpus lewisi, Brevipalpus obovatus, Brevipalpus phoenicis, Bryobia praetiosa, Bryobia rubrioculus, Dolichotetranychus floridanus, Eotetranychus boreus, Eotetranychus geniculatus, Eotetranychus pruni, Eotetranychus sexmanaculatus, Eotetranychus smithi, Eotetranychus uncatus, Oligonychus hondoensis, Oligonychus ilicis, Oligonychus karamatus, Oligonychus shinkajii, Panonychus citri, Panonychus mori, Panonychus ulmi, Tenuipalpus zhizhilashviliae, Tetranychus cinnabarinus, Tetranychus kanzawai, Tetranychus urticae, Tetranychus viennensis* or *Tuckerella pavoniformis;* acari belonging to the Eriophyidae family, such as *Acaphylla theavagrans, Aceria paradianthi, Aceria tulipae, Aculops lycopersici, Aculops pelekassi, Aculus fockeui, Aculus schlechtendali, Calacarus carinatus, Calepitrimerus vitis, Colomerus vitis, Epitrimerus pyri, Eriophes kuko* or *Eriophyes chibaensis;* acari belonging to the Astigmata family, such as *Acarus siro, Aleuroglyphus ovatus, Carpoglyphus lactis, Lardoglyphus konoi, Rhizoglyphus echinopus, Rhizoglyphus robini, Tyrophagus putrescentiae* or *Tyrophagus similis;* acari belonging to the Tarsonemidae family, such as *Phytonemus pallidus, Polyphagotarsonemus latus, Tarsonemus bilobatus* or *Tarsonemus waitei;* acari belonging to the Eupodidae family, such as *Penthaleus erythrocephalus* or *Penthaleus major;* acari belonging to the Ixodidaefamily, such as *Haemaphysalis longicornis, Haemaphysalis japonica, Boophilus microplus, Dermacentor recticulatus, Dermacentor taiwanensis, Haemaphysalis flava, Ixodes ovatus, Ixodes persulcatus, Dermacentor reticulatus* or the like.

In addition, resistant acari having resistance to conventionally known acaricides is also included in the above examples of acari.

The cyclic amine compound of the present invention or salt thereof causes little chemical damage, demonstrates low levels of toxicity in fish and warm-blooded animals, and is a compound having a particularly high degree of safety.

[Acaricide]

The acaricide of the present invention contains as an active ingredient thereof at least one type selected from the group consisting of a cyclic amine compound represented by formula (I) or formula (II) or a salt thereof. In the acaricide of the present invention, one type of the cyclic amine compound represented by formula (I) or formula (II) or a salt thereof can be contained alone, or two or more types can be contained in combination.

In addition, although the acaricide of the present invention may contain only the cyclic amine compound represented by formula (I) or formula (II) of the present invention, or a salt thereof, it may also contain a carrier such as a solid carrier, liquid carrier or gaseous carrier. In addition, the acaricide of the present invention may have the cyclic amine compound represented by formula (I) or formula (II), or a salt thereof, impregnated in a base material such as a porous ceramic plate or non-woven fabric. Moreover, a surfactant or other adjunct may be added as necessary.

The acaricide according to the present invention can be formulated into a form able to be typically adopted by agricultural chemicals, namely in the form of a water-dispersible powder, granules, powder, emulsion, water soluble powder, suspension, granular water-dispersible powder, flowable preparation, aerosol, fog, heat transpiration agent, fumigant, poison bait or microcapsules.

Examples of additives and carriers used when formulating a solid preparation include vegetable powders such as soybean powder or flour, mineral fine powders such as diatomaceous earth, apatite, plaster, talc, bentonite, pyrophyllite or clay; and organic and inorganic compounds such as sodium benzoate, urea or sodium sulfate.

Examples of solvents used when formulating liquid preparations include petroleum fractions such as kerosene, xylene or solvent naphtha; cyclohexane, cyclohexanone, dimethylformamide, dimethylsulfoxide, alcohols, acetone, methyl isobutyl ketone, mineral oils, vegetable oils and water.

Examples of gaseous carriers used when formulating propellants include butane gas, LPG, dimethyl ether and carbon dioxide gas.

Examples of base materials of poison bait include bait components such as grain powder, vegetable oil, sugar or crystalline cellulose, antioxidants such as dimethylhydroxytoluene or nordihydroguaiaretic acid, preservatives such as dehydroacetic acid, accidental swallowing preventives for small children and pets such as cayenne pepper powder, insect-attracting fragrances such as cheese fragrance or onion fragrance.

A surfactant can be added in order to obtain a uniform and stable form during formulation. Examples of surfactants include nonionic surfactants such as polyoxyethylene alkyl ethers, polyoxyethylene higher fatty acid esters, polyoxyethylene sorbitan higher fatty acid esters or polyoxyethylene tristyryl phenyl ethers, sulfate esters of polyoxyethylene alkyl phenyl ethers, alkylnaphthalene sulfonates, polycarboxylates, lignin sulfonates, formaldehyde condensates of alkylnaphthalene sulfonates and isobutylene-maleic anhydride copolymers.

In the case of using the acaricide of the present invention in agricultural applications, the content of the cyclic amine compound of the present invention or salt thereof in a preparation is preferably 0.01% by weight to 90% by weight and more preferably 0.05% by weight to 85% by weight.

An acaricide for agricultural use that is supplied in the form of a water-dispersible powder, emulsion, suspension, flowable preparation, water-soluble powder or granular water-dispersible powder can be prepared in the form of a solution, suspension or emulsion by diluting to a prescribed concentration with water and then sprayed onto plants or soil. In addition, an acaricide for agricultural use that is supplied in the form of a powder or granules can be sprayed directly onto plants or soil.

In addition, an acaricide for epidemic prevention that is supplied in the form of an emulsion, water-dispersible powder or flowable preparation and the like can be applied by diluting to a prescribed concentration with water. In addition, an acaricide for epidemic prevention that is supplied in the form of an oil solution, aerosol, fog, poison bait or miticidal sheet can be used directly.

In the case of using the acaricide of the present invention to control animal parasitic acari of livestock such as cows or pigs and pets such as dogs or cats, the cyclic amine compound of the present invention can be used at a ratio of 0.01 mg to 1000 mg per 1 kg of host animal.

An acaricide for controlling animal parasitic acari can be applied using a known veterinary method. Examples of such methods include methods in which the acaricide is administered to an animal by a tablet, capsule, immersion liquid, food additive, suppository or injection (intramuscular, subcutaneous, intravenous or intraabdominal injection) when administered for the purpose of systemic control, methods in which an oily or aqueous liquid preparation is administered by spraying, pouring on or spotting on when administered for the purpose of non-systemic control, and methods in which the acaricide is mixed with a resin and the kneaded product is molded into a suitable shape such as that of a collar or ear tag which is then attached to the animal.

The acaricide of the present invention can be mixed or used in combination with fungicides, other insecticides or acaricides, nematocides, soil pesticides, plant regulators, synergists, fertilizers, soil improvers or animal feeds and the like.

The following lists typical examples of fungicides, other insecticides or acaricides, nematocides, soil pesticides and plant regulators able to be used by mixing with the compound of the present invention.

Fungicides:

1) benzimidazole-based: benomyl, carbendazim, fuberidazole, thiabendazole, methyl thiophanate or the like;

2) dicarboxylmide-based fungicides: chlozolinate, iprodione, procymidone, vinclozolin or the like;

3) DMI fungicides: imdazalil, oxpoconazole, pefurazoate, prochloraz, triflumizole, triforine, pyrifenox, fenarimol, nuarimol, azaconazole, bitertanol, bromconazole, cyproconazole, difenoconazole, diniconazole, epoxyconazole, fenbuconazole, fluquinconazole, flusilazole, flutriafol, hexaconazole, imibenconazole, ipuconazole, metconazole, myclobutanil, penconazole, propiconazole, prothioconazole, simeconazole, tebuconazole, tetraconazole, triadimefon, triadimenol, triticonazole, etaconazole, furconazole-cis or the like;

4) phenylamide-based: benalaxyl, furalaxyl, metalaxyl, metalaxyl-M, oxadixyl, ofurace or the like;

5) amine-based: aldimorph, dodemorph, fenpropimorph, tridemorph, fenpropidine, piperalin, spiroxamine or the like;

6) phosphothiolate-based: EDDP, iprobenfos, pyrazophos or the like;

7) dithiolane-based: isoprothiolane or the like;

8) carboxamide-based: benodanil, boscalid, carboxin, fenfuran, flutolanil, furametpyr, mepronil, oxycarboxin, penthiopyrad, thifluzamide or the like;

9) hydroxy(2-amino)pyrimidine-based: bupirimate, dimethirimol, ethirimol or the like;

10) AP fungicides (anilinopyrimidines-based): cyprodinil, mepanipyrim, pyrimethanil or the like;

11) N-phenylcarbamate-based: diethofencarb or the like;

12) QoI fungicides (Qo inhibitor-based): azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen or the like;

13) PP fungicides (phenylpyrrole-based): fenpiconil, fludioxonil or the like;

14) quinoline-based: quinoxyfen or the like;

15) AH fungicides (aromatic hydrocarbon-based): biphenyl, chloroneb, dichloran, quintozene, tecnazene, tolclofos-methyl or the like;

16) MBI-R-based: fthalide, pyroquilon, triciclazole or the like;

17) MBI-D-based: carpropamid, diclocymet, fenoxanil or the like;

18) SBI agents: fenhexamid, pyributicarb, terbinafine or the like;

19) phenylureas: pencycuron or the like;

20) QiI fungicides (Qi inhibitors): cyazofamid or the like;

21) benzamide-based: zoxamide or the like;

22) enopyranurone-based: blasticidin, mildiomycin or the like;

23) hexopyranosyl-based: kasugamycin or the like;

24) glucopyranosyl-based: streptomycin, validamycin or the like;

25) cyanoacetoamide-based: cymoxanil or the like;

26) carbamate-based: idocarb, propamocarb, prothiocarb, polycarbamate or the like;

27) uncoupling agents: binapacryl, dinocap, ferimzone, fluazinam or the like;

28) organic tin compounds: triphenyltin acetate, triphenyltin chloride, triphenyltin hydroxide or the like;

29) phosphate esters: phosphonic acid, tolclofos-methyl, fosetyl or the like;

30) phthalamide-based: tecloftalam or the like;

31) benzotriazine-based: triazoxide or the like;

32) benzene sulfonamide-based: flusulfamide or the like;

33) pyridazinones: diclomezine or the like;

34) CAA fungicide (carboxylic amide)-based: dimethomorph, flumorph, benthiavalicarb, iprovalicarb, mandipropamide or the like;

35) tetracyclines: oxytetracycline or the like;

36) thiocarbamate-based: methasulfocarb or the like; and, 37) other compounds: etridiazole, polyoxins, oxolinic acid, hydroxyisoxazole, octinoline, silthiofam, diflumetorim, acibenzolar-s-methyl, probenazole, tiadinil, ethaboxam, cyflufenamid, proquinazid, metrafenone, fluopicolide, cupric hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine acetate, iminoctadine dodecylbenzene sulfonate, anilazine, dithianon, chloropicrin, dazomet, metam sodium salt, chinomethionat, cyprofuram, silthiofam, *agrobacterium*, fluoroimide.

Examples of insecticides, acaricides, nematocides and soil pesticides include:

1) organic (thio)phosphate-based: such as acephate, azamethiphos, azinphos-methyl, chlorpyriphos, chlorpyriphos-methyl, chlorfenvinphos, diazinon, dichlorvos, dicrotophos, dimethoate, disulfoton, ethion, EPN, fenamiphos, fenitrothion, fenthion, isoxathion, malathion, methamidophos, methidathion, methyl parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprofos, tetrachlorvinphos, terbufos, triazophos, trichlorfon, fosthiazate, phosphocarb, cadusafos, disulfoton, demeton-s-methyl, BRP, CYAP, ethoprophos, quinalphos, dimethylvinphos, vamidothion, pyraclofos, or the like;

2) carbamate-based: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridafenthion, furathiocarb, XMC or the like;

3) pyrethroid-based: allethrin, bifenthrin, cyfluthrin, cyhalothrin, cyphenothrin, cypermethrin, alphacypermethrin, betacypermethrin, zetacypermethrin, deltamethrin, esfenvalerate, etofenprox, fenpropathrin, fenvalerate, imiprothrin, lambdacyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, acrinathrin, cycloprothrin, halfenprox, flucythrinate or the like;

4) growth regulators:

a) chitin synthesis inhibitors: chlorfluazuron, diflubenzuron, flucycloxuron, flufenoxuron, hexaflumuron, lufenuron, novaluron, teflubenzuron, triflumuron, bistrifluoron, nobifumuron, buprofezin, diofenolan, hexythiazox, etoxazole, clofentezine or the like;

b) ecdysone antagonists: halofenozide, methoxyfenozide, tebufenozide, azadirachtin, chromafenozide or the like;

c) juvenile hormone-like substances: pyriproxyfen, methoprene or fenoxycarb;

d) lipid biosynthesis inhibitors: spirodiclofen, spiromesifen, spirotetramat or the like;

5) nicotine receptor agonist/antagonist compounds: acetamiprid, clothianidine, dinotefuran, imidacloprid, nitenpyram, thiacloprid, thiamethoxam or the like;

6) GABA antagonist compounds: acetochlor, endosulfan, ethiprole, fipronil, vaniliprole, pyrafluprole, pyriprole or the like;

7) macrocyclic lactone insecticides: abamectin, emamectin, milbemectin, lepimectin, spinosad, ivermectin or the like;

8) METI I compounds: fenazaquin, pyridaben, tebufenpyrad, tolfenpyrad, flufenirim or the like;

9) METI II and III compounds: acequinocyl, fluacyprim, hydramethylnon or the like;

10) uncoupling agent compounds: chlorfenapyr or the like;

11) oxidative phosphorylation inhibitor compounds: cyhexitin, diafenthiuron, fenbutatin oxide, propargite or the like;

12) molting disruption compounds: cyromazine or the like;

13) mixed function oxidase inhibitor compounds: piperonyl butoxide or the like;

14) sodium channel blocker compounds: indoxacarb, metaflumizone;

15) microbial pesticides: BT agents, insect pathogen viral agents, insect pathogen fungal agents, nematode pathogen fungal agents or the like;

16) other compounds: benclothiaz, bifenazate, cartap, flonicamid, pyradalyl, pymetrozine, sulfur, thiocyclam, flubendiamide, cyenopyrafen, flupyrazofos, cyflumetofen, amidoflumet, bensultap, dicofol, tetradifon, fenpyroximate, amitraz, chlordimeform, triazamate, pymetrozine, pyrimidifen, 1,3-dichloropropene, clofentenzine, fluacrypyrim, rotenone, DCIP, phenisobromolate, benzomate, methaldehyde, chlorantraniliprole, spinetoram, pyrifluquinzaon or the like.

Examples of plant growth regulators include:

abscisic acid, indole butyric acid, uniconazole, ethychlozate, ethephon, cloxyfonac, chlormequat, *chlorella* extract, calcium peroxide, cyanamide, dichlorprop, gibberellin, daminozide, decyl alcohol, trinexapac-ethyl, mepiquat-chloride, paclobutrazol, paraffin wax, piperonyl butoxide, pyraflufen ethyl, flurprimidol, prohydrojasmon, prohexadione-calcium, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene, aviglycine hydrochloride and the like.

EXAMPLES

The following provides a more detailed explanation of the present invention by indicating examples thereof. However, the scope of the present invention is not limited by the following examples.

Example 1

Production of 3-endo-[2-i-butoxy-4-(trifluoromethyl) phenoxy]-9-[5-(trifluoromethyl)-2-pyridyloxy]-9-azabicyclo[3.3.1]nonane (Compound No. H-1)

[Chemical formula 13]

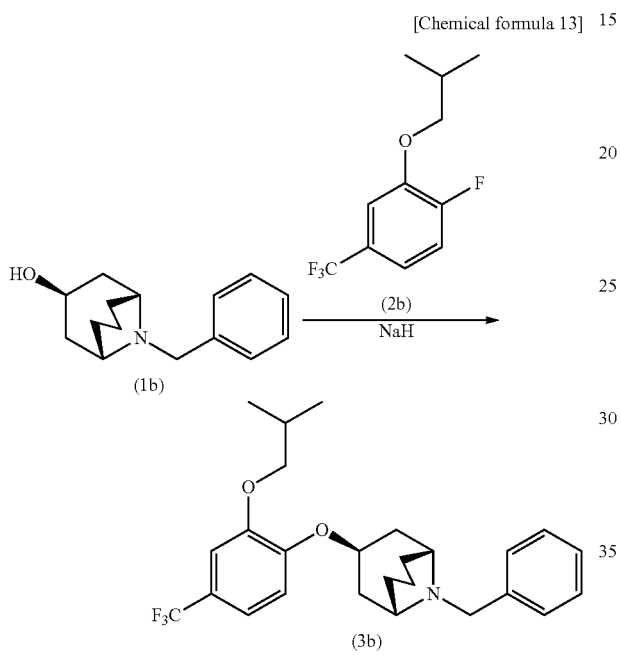

3-endo-9-benzyl-9-azabicyclo[3.3.1]nonane-3-ol (Compound (1b)) was synthesized by the method described in WO 2007/039563.

An N,N-dimethyl formamide (14 ml) solution of compound (1b) (1.35 g) and 4-fluoro-3-i-butoxybenzotrifluoride (compound (2b)) (1.38 g) was heated to 90° C., followed by adding 60% sodium hydride (0.35 g) and stirring for 2 hours. The resulting mixture was then cooled to room temperature, poured into water, and extracted with ethyl acetate. The organic layer was washed with water, dried with anhydrous magnesium sulfate, filtered, and concentrated under reduced pressure. The residue was purified by column chromatography to obtain the target compound (3b) (2.04 g).

[Chemical formula 14]

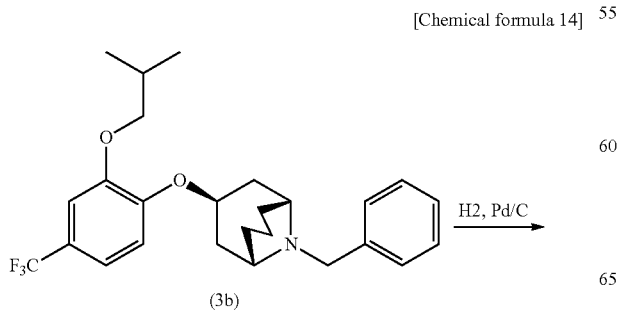

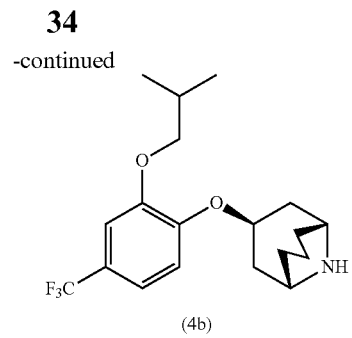

A 10% palladium-carbon (0.4 g) was added to an ethanol (20 ml) solution of compound (3b) (2.04 g). The resulting suspension was heated at 50° C. under a hydrogen atmosphere for 5 hours. The suspension was then cooled and filtered over elite, and the filtrate was distilled off under reduced pressure. The obtained compound (4b) was used in the next reaction without purifying further.

[Chemical formula 15]

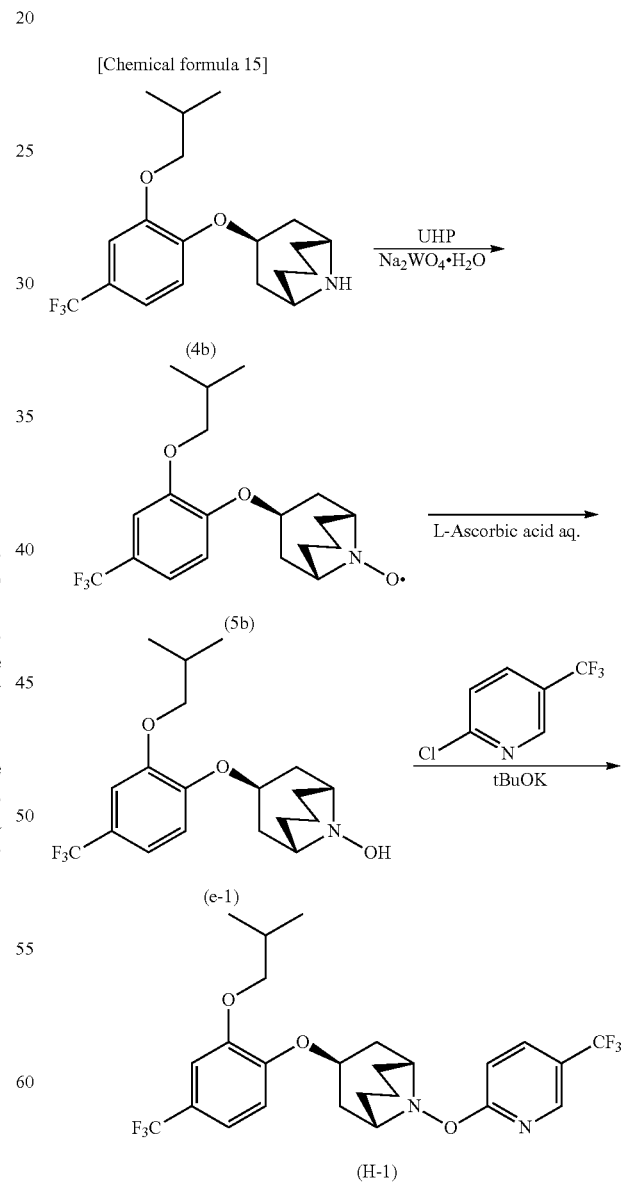

A tungstic acid sodium hydrate (0.13 g) was added to an acetonitrile (14 ml) solution of the crude compound (4b)

(1.41 g) at room temperature, followed by stirring for 30 minutes. The resulting mixture was then cooled to 0° C., followed by adding an urea-hydrogen peroxide adduct (UHP, 0.75 g). The resulting mixture was stirred at 0° C. for 45 minutes and further stirred at room temperature for 2 hours. Water was added to the mixture, followed by extracting with chloroform. The organic layer was dried and concentrated with anhydrous potassium carbonate. The residue was purified by column chromatography to obtain compound (5b) (0.57). Compound (5b) was then diluted with chloroform and treated with an ascorbic acid aqueous to obtain a crude compound (e-1) (0.37 g). Next, t-butoxypotassium (1M tetrahydrofuran, 1.11 ml) was added to a tetrahydrofuran (4 ml) solution of the crude compound (e-1) (0.37 g) and 2-chloro-5-(trifluoromethyl)pyridine (0.18 g) at 0° C. under a nitrogen atmosphere, followed by warming to room temperature and stirring for 2 hours. Water was added to the resulting mixture, and the resulting mixture was extracted with ethyl acetate. The organic layer was washed with water, dried with anhydrous magnesium sulfate, filtered, and concentrated under reduced pressure. The residue was purified by column chromatography to obtain the target compound H-1 (0.27 g).

Example 2

Production of 3-endo-[2-i-butoxy-4-(trifluoromethyl)phenoxy]-9-hydroxy-9-azabicyclo[3.3.1]nonane (compound No. e-1)

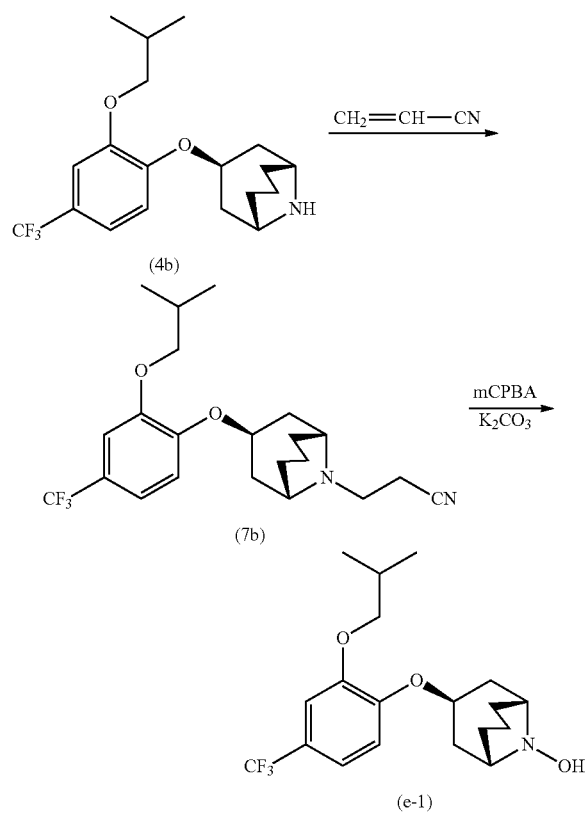

[Chemical formula 16]

Acrylonitrile (9.07 g) was added to a methanol solution (300 ml) of the crude compound (4b) (30.23 g) at room temperature, followed by stirring overnight. The solvent was concentrated under reduced pressure, and the residue was purified by silica gel column chromatography (hexane:ethyl acetate=4:1 to 6:4) to obtain compound (7b) (30.4 g, viscous oil).

Potassium carbonate (15.5 g) and metachloroperbenzoic acid (purity of 70%, 23.71 g) were added to a methylene chloride solution (600 ml) of compound (7b) (30.4 g) at room temperature, followed by stirring the resulting mixture for 4 hours. Anhydrous magnesium sulfate (10 g) was added to the mixture and the mixture was filtered, followed by concentrating the solvent under reduced pressure. The residue was diluted with ethyl acetate, washed with ascorbic acid aqueous, then water, dried with anhydrous magnesium sulfate, filtered, and concentrated under reduced pressure. Hexane was added to the residue to cure and thereby obtaining a crude compound (e-1) (17.79 g). Furthermore, the mother liquid thereof was purified by column chromatography to obtain a crystalline compound (e-1) (8.12 g, melting point of 112-115° C.).

Example 3

Production of 3-endo-[2-i-butoxy-4-(trifluoromethyl)phenoxy]-9-[5-(trifluoromethyl)-2-pyridyl thio]-9-azabicyclo[3.3.1]nonane (compound No. N-1)

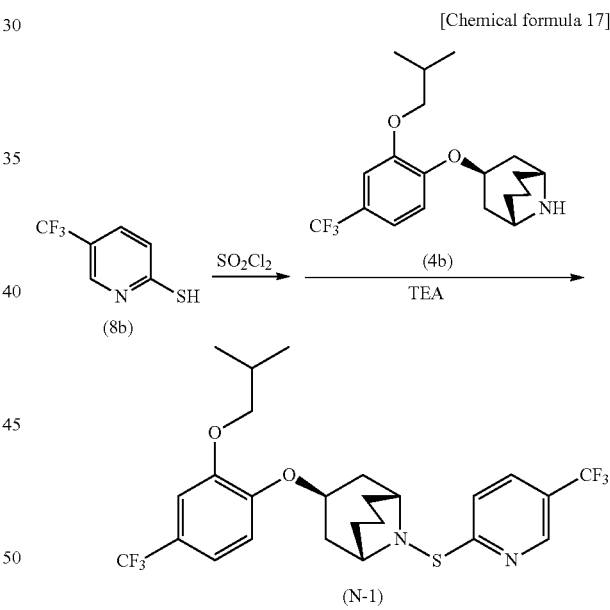

[Chemical formula 17]

A methylene chloride (10 ml) solution of compound (8b) (0.55 g) that can be produced by well-known methods was cooled to 0° C. under a nitrogen atmosphere followed by adding sulfryl chloride (0.46 g). The resulting mixture was stirred for 1 hour, followed by concentrating under reduced pressure. A solution obtained by diluting the residue with methylene chloride (10 ml) was dropped into a methylene chloride (10 ml) solution of the crude compound (4b) (1.0 g) and triethylamine (0.34 g) while cooling with ice, followed by slowly warming to room temperature and just stirring overnight. The resulting mixture was poured into water, followed by extracting with chloroform. The organic layer was washed with water, dried with anhydrous magnesium sulfate, filtered, and concentrated under reduced pressure. The residue was purified by silica gel column chromatography (hexane:ethyl acetate=9:1) to obtain the target compound (N-1) (1.36 g, viscous oil).

Example 4

Production of 3-oxa-7-endo-[5-(trifluoromethyl)-2-pyridyloxy]-9-[2-isopropoxycarbonyl-4-(trifluoromethyl)phenoxy]-9-azabicyclo[3.3.1]nonane (compound No. (K-12))

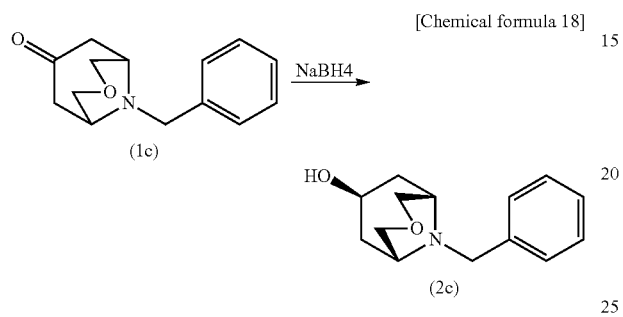

9-benzyl-3-oxa-9-azabicyclo[3.3.1]nonane-7-one (1c) was synthesized by the method described in WO2007/022502. Sodium boron hydride (0.785 g) was added to an ethanol (50 ml) solution of compound (1c) (4 g) at room temperature, followed by stirring the resulting mixture for 3 hours. The mixture was then cooled, and concentrated under reduced pressure, followed by pouring into water and extracting with ethyl acetate. The organic layer was washed with water, dried with anhydrous magnesium sulfate, filtered, and concentrated under reduced pressure. The residue was purified by column chromatography to obtain compound (2c) (3.62 g).

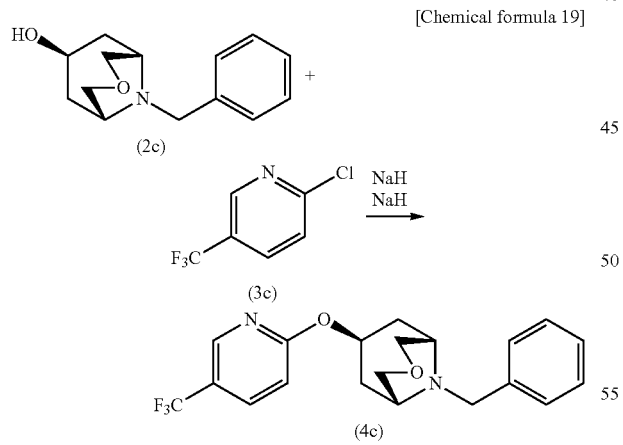

A DMF (30 ml) solution of compound (2c) (2.45 g) and 2-chloro-5-(trifluoromethyl)pyridine (2.86 g) was heated to 80° C., followed by adding 60% sodium hydride (0.42 g) to the solution. The resulting mixture was stirred for 30 minutes, followed by adding 60% sodium hydride (0.42 g). The resulting mixture was then just stirred for 2 hours. Then, the mixture was cooled to room temperature, poured into water, followed by extracting with ethyl acetate. The organic layer was washed with water, dried with anhydrous magnesium sulfate, filtered, and concentrated under reduced pressure. The residue was purified by column chromatography to obtain compound (4c) (3.05 g).

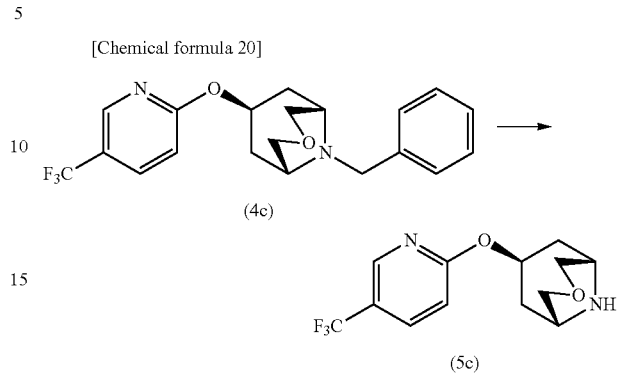

A 20% palladium hydroxide-carbon (0.92 g) was added to an ethanol (50 ml) solution of compound (4c) (3.05 g), followed by heating the resulting suspension at 50° C. for 6 hours. The resulting mixture was then cooled and filtered over celite, and the filtrate was distilled off under reduced pressure. The obtained compound (5c) was used in the next reaction without purifying further.

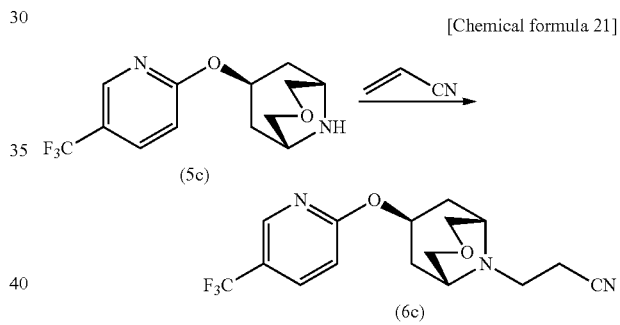

Acrylonitrile (1.06 g) was added to a methanol (50 ml) solution of the crude compound (5c) (2.3 g) at room temperature, followed by stirring overnight. The solvent was concentrated under reduced pressure, and the residue was purified by silica gel column chromatography to obtain compound (6c) (2.11 g).

Compound (6c): mp. 87-90° C.

1H-NMR (CDCl3, δppm) 8.41 (s, 1H), 7.73 (d, 1H), 6.81 (d, 1H), 5.47-5.40 (m, 1H), 3.87 (d, 2H), 3.60 (d, 2H), 2.98 (t, 2H), 2.84 (d, 2H), 2.50-2.42 (m, 4H), 1.87 (d, 1H), 1.82 (d, 1H)

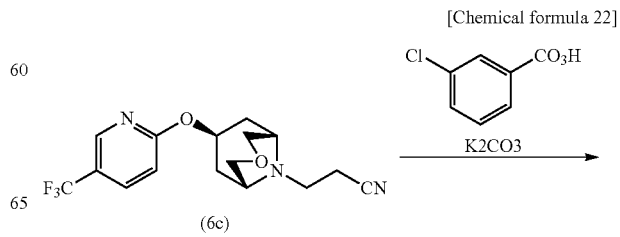

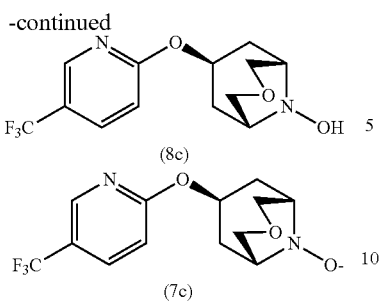

Meta-chloroperbenzoic acid (purity of 70%, 0.58 g) and potassium carbonate (0.4 g) were added to a methylene chloride (20 ml) solution of compound (6c) (0.76 g) at room temperature, followed by stirring for an hour. Anhydrous magnesium sulfate was added to the mixture and the mixture was filtered over celite, followed by concentrating the solvent under reduced pressure. The residue was purified by column chromatography to obtain compound (7c) (0.38) and compound (8c) (0.2 g).

Compound (8c): mp. 110-113° C.

1H-NMR (CDCl3, δppm, measuring temperature 21.2° C.) 8.43 (s, 1H), 7.73 (d, 1H), 6.80 (d, 1H), 5.68-5.61 (m, 0.7H), 5.39-5.36 (m, 0.3H), 4.38 (d, 0.5H), 3.79 (s, 3H), 3.37 (d, 0.5H), 3.24 (d, 1.5H), 3.11 (d, 0.5H), 2.75-2.53 (m, 2H), 2.17-2.05 (brd, 0.5H), 1.78-1.72 (d, d, 1.5H)

[Chemical formula 23]

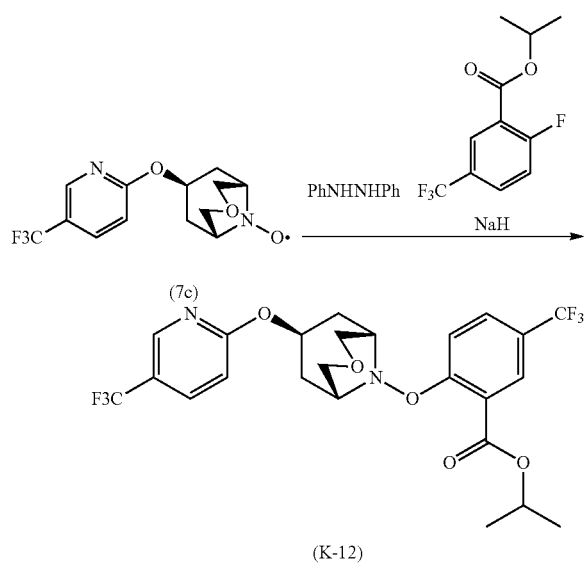

1,2-diphenyl hydrazine (0.14 g) was added to a THF (5 ml) solution of compound (7c) (0.38 g) at room temperature, followed by stirring the resulting mixture for 30 minutes. A 60% sodium hydride (0.06 g) was added to the mixture followed by stirring for 10 minutes. Then, a THF (5 ml) solution of 2-fluoro-5-(trifluoromethyl)benzoic acid isopropyl (0.314 g) was added to the resulting mixture, followed by stirring for an hour. The mixture was then poured into water, and extracted with ethyl acetate. The organic layer was washed with water, dried with anhydrous magnesium sulfate, filtered, and concentrated under reduced pressure. The residue was purified by column chromatography to obtain the target compound (compound No. (K-12)) (0.27 g, viscous oil).

Example 5

Production of 3-endo-[2-butoxy-4-(trifluoromethyl)phenoxy]-9-[5-(trifluoromethyl)-2-pyridyloxy]-9-azabicyclo[3.3.1]nonane (compound No. (H-54))

[Chemical formula 24]

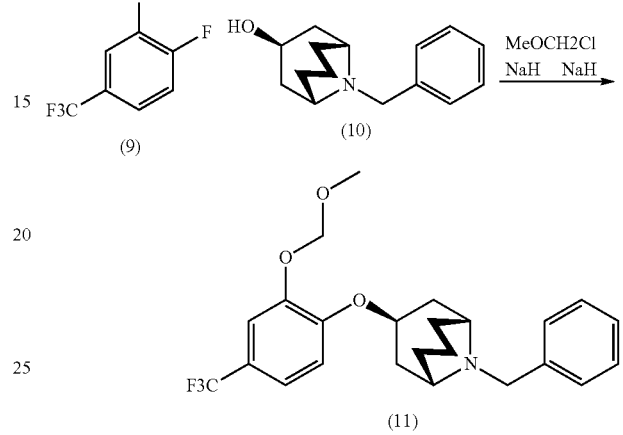

A 60% sodium hydride (0.75 g) was added to a DMF (20 ml) solution of 2-fluoro-5-(trifluoromethyl)phenol (2.83 g) while cooling with ice. The resulting mixture was stirred at room temperature for 30 minutes, and chloromethylether (1.39 g) was dropped into the mixture while cooling with ice. The mixture was then warmed to room temperature and stirred for 30 minutes, and then heated to 80° C. and further stirred for an hour. Compound (10) (4 g) and a 60% sodium hydride (0.94 g) were added to the resulting mixture, followed by stirring for 3 hours. The mixture was then cooled to room temperature, poured into water, and extracted with ethyl acetate. The organic layer was washed with water, dried with anhydrous magnesium sulfate, filtered, and concentrated under reduced pressure. The residue was purified by column chromatography to obtain the target compound (11) (6.29 g).

[Chemical formula 25]

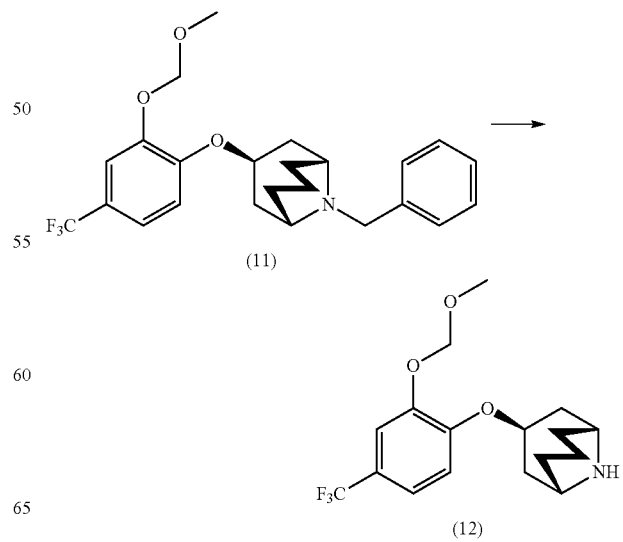

A 20% palladium hydroxide-carbon (1.25 g) was added to an ethanol (100 ml) solution of compound (11) (6.27 g). The resulting suspension was heated at 50° C. under a hydrogen atmosphere for 2 hours, followed by stirring at room temperature overnight. The mixture was then filtered over celite, and the filtrate was distilled off under reduced pressure. The obtained compound (12) was used in the next reaction without purifying further.

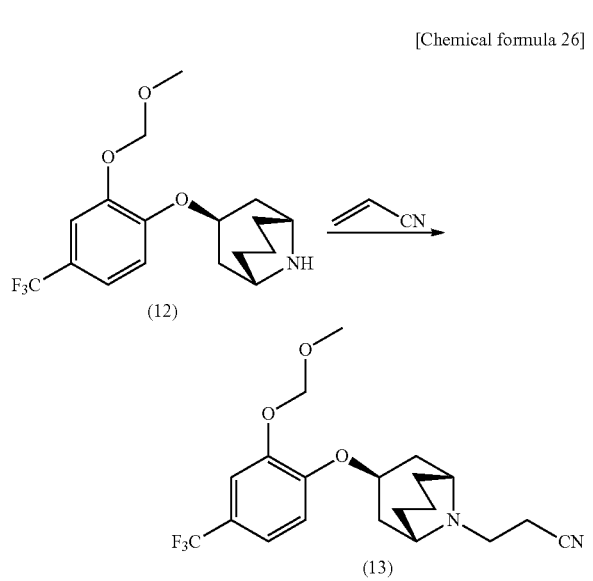

[Chemical formula 26]

Acrylonitrile (1.45 g) was added to a methanol (50 ml) solution of the crude compound (12) (4.71 g) at room temperature, followed by stirring overnight. The solvent was concentrated under reduced pressure, and the residue was purified by silica gel column chromatography to obtain compound (13) (5.09 g, viscous oil).

[Chemical formula 27]

A meta-chloroperbenzoic acid (purity of 70%, 1.2 g) and potassium carbonate (0.78 g) were added to a methylene chloride (30 ml) solution of compound (13) (1.5 g) at room temperature followed by stirring the resulting mixture for 2 hours. Anhydrous magnesium sulfate (10 g) was added to the mixture, and the mixture was filtered, followed by concentrating the solvent under reduced pressure. The residue was diluted with methylene chloride, washed with ascorbic acid aqueous, then water, dried with anhydrous magnesium sulfate, filtered, and concentrated under reduced pressure. The residue was purified by column chromatography to obtain compound (e-14) (1.35 g).

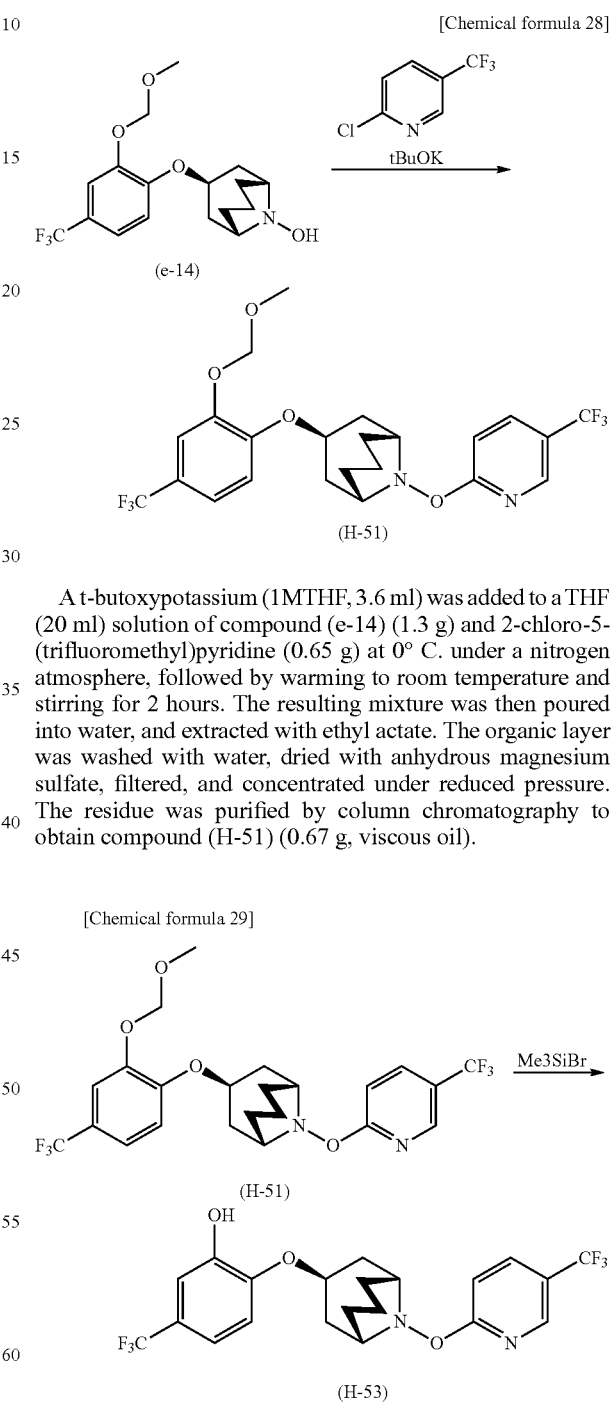

[Chemical formula 28]

A t-butoxypotassium (1MTHF, 3.6 ml) was added to a THF (20 ml) solution of compound (e-14) (1.3 g) and 2-chloro-5-(trifluoromethyl)pyridine (0.65 g) at 0° C. under a nitrogen atmosphere, followed by warming to room temperature and stirring for 2 hours. The resulting mixture was then poured into water, and extracted with ethyl actate. The organic layer was washed with water, dried with anhydrous magnesium sulfate, filtered, and concentrated under reduced pressure. The residue was purified by column chromatography to obtain compound (H-51) (0.67 g, viscous oil).

[Chemical formula 29]

Bromo trimethyl silane (0.302 g) was slowly added to a methylene chloride (5 ml) solution of compound (H-51) (0.25 g) under a nitrogen atmosphere at −30° C. The resulting mixture was then stirred at −30° C. for an hour, followed by taking 2 hours to warm to 0° C. The mixture was then poured into cold water, followed by extracting with ethyl acetate. The organic layer was washed with water, dried with anhydrous magnesium sulfate, filtered, and concentrated under reduced pressure. The residue was purified by column chromatography to obtain compound (H-53) (0.13 g, mp 141-144° C.).

[Chemical formula 30]

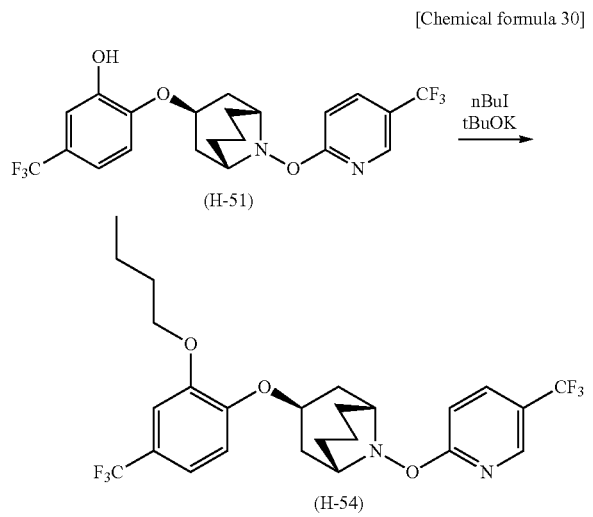

t-Butoxypotassium (0.085 g) was added to a THF (6 ml) solution of compound (H-53) (0.35 g) and 1-iodobutane (0.14 g) while cooling with ice. Then, the mixture was warmed to room temperature, and further heated to 50° C. and stirred overnight. The resulting mixture was then cooled to room temperature, poured into water, and extracted with ethyl acetate. The organic layer was washed with water, dried with anhydrous magnesium sulfate, filtered, and concentrated under reduced pressure. The residue was purified by column chromatography to obtain the target compound (compound No. (H-54)) (0.24 g, viscous oil).

Example 6

Production of 3-endo-[2-phenyl-4-(trifluoromethyl) phenoxy]-9-[5-(trifluoromethyl)-2-pyridyloxy]-9-azabicyclo[3.3.1]nonane (compound No. (H-85))

[Chemical formula 31]

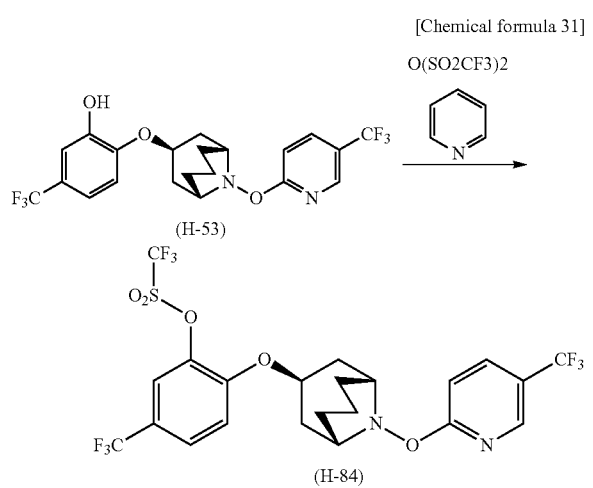

Anhydrous trifluoromethane sulfonic acid (3.66 g) was slowly added to a methylene chloride (50 ml) solution of compound (H-53) (5 g) and pyridine (2.14 g) while cooling with ice. Then, the mixture was warmed to room temperature and stirred overnight. The resulting mixture was then poured into cold water and extracted with methylene chloride. The organic layer was washed with water, dired with anhydrous magnesium sulfate, filtered, and concentrated under reduced pressure. The residue was purified by column chromatography to obtain compound (H-84) (3.7 g, mp 127-130° C.).

[Chemical formula 32]

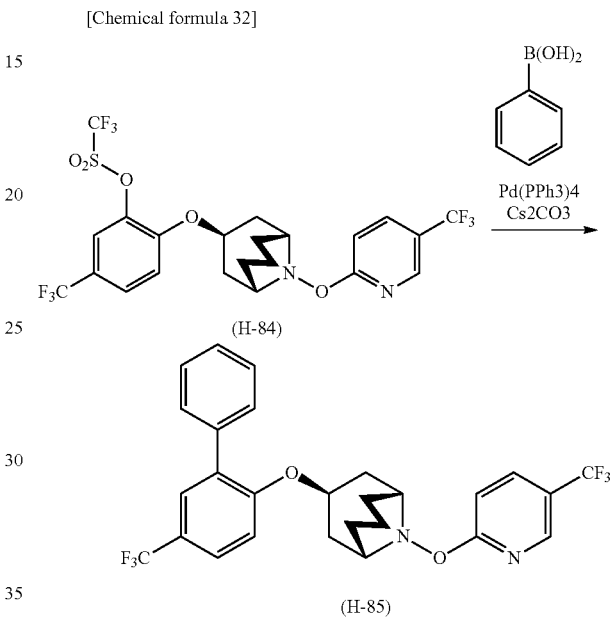

Water (2 ml), cesium carbonate (0.88 g), phenyl boronic acid (0.098 g) and tetrakis(triphenyl phosphine)palladium (0) (0.078 g) were added to a THF (4 ml) solution of compound (H-84) (0.4 g) under a nitrogen atmosphere. The resulting mixture was then heated to 80° C. and stirred overnight. The mixture was then cooled to room temperature, poured into water, and extracted with ethyl acetate. The organic layer was washed with water, dried with anhydrous magnesium sulfate, filtered, and concentrated under reduced pressure. The residue was purified by column chromatography to obtain the target compound (compound No. (H-85)) (0.2 g, viscous oil).

The cyclic amine compounds of the present invention, which can be produced by the above-described production methods, are shown in TABLES 1-5.

In addition, $(R^{10})_m$, $(R^{11})_n$, A, $(R^{21})_r$, and $Cy^2\text{-}(R^{20})_p$ in TABLE 1 represent the substituents of the cyclic amine compound represented by formula (Ig).

$(R^{10})_m$, $(R^{11})_n$, A, $(R^{21})_r$, and $Cy^2\text{-}(R^{20})_p$ in TABLE 2 represent the substituents of the cyclic amine compound represented by formula (Ih).

$(R^{10})_m$, $(R^{11})_n$, A, $(R^{21})_r$, $Cy^1$, $Cy^2$, and $(R^{20})_p$ in TABLE 3 represent the substituents of the cyclic amine compound represented by formula (Ii).

$(R^{10})_m$, $(R^{11})_n$, A, $(R^{21})_r$, $Cy^1$, $Cy^2$, and $(R^{20})_p$ in TABLE 4 represent the substituents of the cyclic compound represented by formula (Ij)

$(R^{10})_m$, $(R^{11})_n$, A, $(R^{21})_r$, $Cy^1$, $Cy^2$, and $(R^{20})_p$ in TABLE 5 represent the substituents of the cyclic amine compound represented by formula (Ik).

$(R^{10})_m$, $(R^{11})_n$, A, $(R^{21})_r$, $Cy^1$, $Cy^2$, and $(R^{20})_p$ in TABLE 6 represent the substituents of the cyclic amine compound represented by formula (II).

In addition, in TABLES 1-6, the numerical values shown in front of the substituents represent the substitution sites. Furthermore, Et represents ethyl group, Me represents methyl group, $^n$Bu represents n-butyl group, $^i$Bu represents i-butyl group, $^s$Bu represents s-butyl group, $^t$Bu represents t-butyl group, $^n$Pen represents n-pentyl group, $^n$Hex represents n-hexyl group, $^c$Pr represents cyclopropyl group, $^c$Bu represents cyclobutyl group, $^c$Pen represents cyclopentyl group, $^c$Hex represents cyclohexyl group.

[Chemical formula 33]

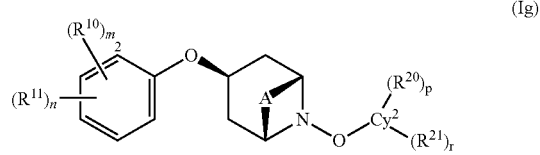

(Ig)

TABLE 1

| No. | $(R^{10})_m$ | $(R^{11})_n$ | A | $Cy^2$-$(R^{20})_p$ | $(R^{21})_r$ |
|---|---|---|---|---|---|
| H-1 | 2-(OCH$_2$$^i$Pr) | 4-CF$_3$ | C$_3$H$_6$ | 5-CF$_3$-pyridin-2-yl | — |
| H-2 | 2-(OCH$_2$$^c$Pr) | 4-CF$_3$ | C$_3$H$_6$ | 5-CF$_3$-pyridin-2-yl | — |
| H-3 | 2-(CH$_2$OCH(OCH$_3$)CH$_3$) | 4-CF$_3$ | C$_3$H$_6$ | 5-CF$_3$-pyridin-2-yl | — |
| H-4 | 2-(CO$_2$CH$_3$) | 4-CF$_3$ | C$_3$H$_6$ | 5-CF$_3$-pyridin-2-yl | — |
| H-5 | 2-(OCH$_2$$^i$Pr) | 4-CF$_3$ | C$_3$H$_6$ | 6-CF$_3$-pyridazin-3-yl | — |
| H-6 | 2-(OCH$_2$$^c$Pr) | 4-CF$_3$ | C$_3$H$_6$ | 6-CF$_3$-pyridazin-3-yl | — |
| H-7 | 2-(CH$_2$OCH(OCH$_3$)CH$_3$) | 4-CF$_3$ | C$_3$H$_6$ | 6-CF$_3$-pyridazin-3-yl | — |
| H-8 | 2-(CO$_2$$^i$Pr) | 4-CF$_3$ | C$_3$H$_6$ | 6-CF$_3$-pyridazin-3-yl | — |
| H-9 | 2-(OCH$_2$$^i$Pr) | 4-CF$_3$ | C$_3$H$_6$ | 5-CF$_3$-pyrimidin-2-yl | — |
| H-10 | 2-(OCH$_2$$^c$Pr) | 4-CF$_3$ | C$_3$H$_6$ | 5-CF$_3$-pyrimidin-2-yl | — |
| H-11 | 2-(CH$_2$OCH(OCH$_3$)CH$_3$) | 4-CF$_3$ | C$_3$H$_6$ | 5-CF$_3$-pyrimidin-2-yl | — |
| H-12 | 2-(CO$_2$$^i$Pr) | 4-CF$_3$ | C$_3$H$_6$ | 5-CF$_3$-pyrimidin-2-yl | — |
| H-13 | 2-(OCH$_2$$^i$Pr) | 4-CF$_3$ | C$_3$H$_6$ | 5-CF$_3$-thiazol-2-yl | — |
| H-14 | 2-(OCH$_2$$^c$Pr) | 4-CF$_3$ | C$_3$H$_6$ | 5-CF$_3$-thiazol-2-yl | — |
| H-15 | 2-(CH$_2$OCH(OCH$_3$)CH$_3$) | 4-CF$_3$ | C$_3$H$_6$ | 5-CF$_3$-thiazol-2-yl | — |
| H-16 | 2-(CO$_2$$^i$Pr) | 4-CF$_3$ | C$_3$H$_6$ | 5-CF$_3$-thiazol-2-yl | — |
| H-17 | 2-(OCH$_2$$^i$Pr) | 4-CF$_3$ | C$_3$H$_6$ | 5-CF$_3$-[1,3,4]thiadiazol-2-yl | — |
| H-18 | 2-(OCH$_2$$^c$Pr) | 4-CF$_3$ | C$_3$H$_6$ | 5-CF$_3$-[1,3,4]thiadiazol-2-yl | — |
| H-19 | 2-(CH$_2$OCH(OCH$_3$)CH$_3$) | 4-CF$_3$ | C$_3$H$_6$ | 5-CF$_3$-[1,3,4]thiadiazol-2-yl | — |
| H-20 | 2-(CO$_2$$^i$Pr) | 4-CF$_3$ | C$_3$H$_6$ | 5-CF$_3$-[1,3,4]thiadiazol-2-yl | — |
| H-21 | 2-(OCH$_2$$^i$Pr) | 4-CF$_3$ | CH$_2$OCH$_2$ | 5-CF$_3$-pyridin-2-yl | — |
| H-22 | 2-(OCH$_2$$^c$Pr) | 4-CF$_3$ | CH$_2$OCH$_2$ | 5-CF$_3$-pyridin-2-yl | — |
| H-23 | 2-(CH$_2$OCH(OCH$_3$)CH$_3$) | 4-CF$_3$ | CH$_2$OCH$_2$ | 5-CF$_3$-pyridin-2-yl | — |
| H-24 | 2-(CO$_2$$^i$Pr) | 4-CF$_3$ | CH$_2$OCH$_2$ | 5-CF$_3$-pyridin-2-yl | — |
| H-25 | 2-(OCH$_2$$^i$Pr) | 4-CF$_3$ | CH$_2$OCH$_2$ | 6-CF$_3$-pyridazin-3-yl | — |
| H-26 | 2-(OCH$_2$$^c$Pr) | 4-CF$_3$ | CH$_2$OCH$_2$ | 6-CF$_3$-pyridazin-3-yl | — |
| H-27 | 2-(CH$_2$OCH(OCH$_3$)CH$_3$) | 4-CF$_3$ | CH$_2$OCH$_2$ | 6-CF$_3$-pyridazin-3-yl | — |
| H-28 | 2-(CO$_2$$^i$Pr) | 4-CF$_3$ | CH$_2$OCH$_2$ | 6-CF$_3$-pyridazin-3-yl | — |
| H-29 | 2-(OCH$_2$$^i$Pr) | 4-CF$_3$ | CH$_2$OCH$_2$ | 5-CF$_3$-pyrimidin-2-yl | — |
| H-30 | 2-(OCH$_2$$^c$Pr) | 4-CF$_3$ | CH$_2$OCH$_2$ | 5-CF$_3$-pyrimidin-2-yl | — |
| H-31 | 2-(CH$_2$OCH(OCH$_3$)CH$_3$) | 4-CF$_3$ | CH$_2$OCH$_2$ | 5-CF$_3$-pyrimidin-2-yl | — |
| H-32 | 2-(CO$_2$$^i$Pr) | 4-CF$_3$ | CH$_2$OCH$_2$ | 5-CF$_3$-pyrimidin-2-yl | — |
| H-33 | 2-(OCH$_2$$^i$Pr) | 4-CF$_3$ | CH$_2$OCH$_2$ | 5-CF$_3$-thiazol-2-yl | — |
| H-34 | 2-(OCH$_2$$^c$Pr) | 4-CF$_3$ | CH$_2$OCH$_2$ | 5-CF$_3$-thiazol-2-yl | — |
| H-35 | 2-(CH$_2$OCH(OCH$_3$)CH$_3$) | 4-CF$_3$ | CH$_2$OCH$_2$ | 5-CF$_3$-thiazol-2-yl | — |
| H-36 | 2-(CO$_2$$^i$Pr) | 4-CF$_3$ | CH$_2$OCH$_2$ | 5-CF$_3$-thiazol-2-yl | — |
| H-37 | 2-(OCH$_2$$^i$Pr) | 4-CF$_3$ | CH$_2$OCH$_2$ | 5-CF$_3$-[1,3,4]thiadiazol-2-yl | — |
| H-38 | 2-(OCH$_2$$^c$Pr) | 4-CF$_3$ | CH$_2$OCH$_2$ | 5-CF$_3$-[1,3,4]thiadiazol-2-yl | — |
| H-39 | 2-(CH$_2$OCH(OCH$_3$)CH$_3$) | 4-CF$_3$ | CH$_2$OCH$_2$ | 5-CF$_3$-[1,3,4]thiadiazol-2-yl | — |
| H-40 | 2-(CO$_2$$^i$Pr) | 4-CF$_3$ | CH$_2$OCH$_2$ | 5-CF$_3$-[1,3,4]thiadiazol-2-yl | — |
| H-41 | 2-(OCH$_2$$^i$Pr) | 4-CF$_3$ | C$_3$H$_6$ | 5-CN-pyridin-2-yl | — |
| H-42 | 2-(OEt) | 4-CF$_3$ | C$_3$H$_6$ | 5-CF$_3$-pyridin-2-yl | — |
| H-43 | 2-(O$^n$Pr) | 4-CF$_3$ | C$_3$H$_6$ | 5-CF$_3$-pyridin-2-yl | — |
| H-44 | 2-(OCH$_2$$^c$Pr) | 4-CF$_3$ | C$_3$H$_6$ | 5-CN-pyridin-2-yl | — |
| H-45 | 2-(CH$_2$OCH(OCH$_3$)CH$_3$) | 4-CF$_3$ | C$_3$H$_6$ | 5-CN-pyridin-2-yl | — |
| H-46 | 2-(CO$_2$$^i$Pr) | 4-CF$_3$ | C$_3$H$_6$ | 5-CN-pyridin-2-yl | — |
| H-47 | 2-(OCH$_2$$^i$Pr) | 4-CF$_3$ | C$_3$H$_6$ | 6-CN-pyridazin-3-yl | — |
| H-48 | 2-(OCH$_2$$^c$Pr) | 4-CF$_3$ | C$_3$H$_6$ | 6-CN-pyridazin-3-yl | — |
| H-49 | 2-(CH$_2$OCH(OCH$_3$)CH$_3$) | 4-CF$_3$ | C$_3$H$_6$ | 6-CN-pyridazin-3-yl | — |
| H-50 | 2-(CO$_2$$^i$Pr) | 4-CF$_3$ | C$_3$H$_6$ | 6-CN-pyridazin-3-yl | — |
| H-51 | 2-(OCH$_2$OMe) | 4-CF$_3$ | C$_3$H$_6$ | 5-CF$_3$-pyridin-2-yl | — |
| H-52 | 2-(OCH$_2$$^i$Pr) | 4-CF$_3$ | C$_3$H$_6$ | 6-CN-pyridazin-3-yl | — |
| H-53 | 2-OH | 4-CF$_3$ | C$_3$H$_6$ | 5-CF$_3$-pyridin-2-yl | — |
| H-54 | 2-(O$^n$Bu) | 4-CF$_3$ | C$_3$H$_6$ | 5-CF$_3$-pyridin-2-yl | — |

TABLE 1-continued

| No. | $(R^{10})_m$ | $(R^{11})_n$ | A | $Cy^2$-$(R^{20})_p$ | $(R^{21})_r$ |
|---|---|---|---|---|---|
| H-55 | 2-([1,3]Dioxolan-2-yl) | 4-CF$_3$ | C$_3$H$_6$ | 5-CF$_3$-pyridin-2-yl | — |
| H-56 | 2-(CH$_2$O$^i$Pr) | 4-CF$_3$ | C$_3$H$_6$ | 5-CF$_3$-pyridin-2-yl | — |
| H-57 | 2-(CH$_2$OCH$_3$) | 4-CF$_3$ | C$_3$H$_6$ | 5-CF$_3$-pyridin-2-yl | — |
| H-58 | 2-(CH$_2$OEt) | 4-CF$_3$ | C$_3$H$_6$ | 5-CF$_3$-pyridin-2-yl | — |
| H-59 | 2-(NH$^i$Bu) | 4-CF$_3$ | C$_3$H$_6$ | 5-CF$_3$-pyridin-2-yl | — |
| H-60 | 2-(O$^i$Pr) | 4-CF$_3$ | C$_3$H$_6$ | 5-CF$_3$-pyridin-2-yl | — |
| H-61 | 2-(O$^s$Bu) | 4-CF$_3$ | C$_3$H$_6$ | 5-CF$_3$-pyridin-2-yl | — |
| H-62 | 2-(OCO$_2$$^i$Pr) | 4-CF$_3$ | C$_3$H$_6$ | 5-CF$_3$-pyridin-2-yl | — |
| H-63 | 2-(OCH$_2$CF$_3$) | 4-CF$_3$ | C$_3$H$_6$ | 5-CF$_3$-pyridin-2-yl | — |
| H-64 | 2-(OCH$_2$CH=CH$_2$) | 4-CF$_3$ | C$_3$H$_6$ | 5-CF$_3$-pyridin-2-yl | — |
| H-65 | 2-(OCH$_2$CH=C(CH$_3$)$_2$) | 4-CF$_3$ | C$_3$H$_6$ | 5-CF$_3$-pyridin-2-yl | — |
| H-66 | 2-(OCH$_2$$^t$Bu) | 4-CF$_3$ | C$_3$H$_6$ | 5-CF$_3$-pyridin-2-yl | — |
| H-67 | 2-(OCH$_2$CH=CCl$_2$) | 4-CF$_3$ | C$_3$H$_6$ | 5-CF$_3$-pyridin-2-yl | — |
| H-68 | 2-(OCH$_2$C≡CH) | 4-CF$_3$ | C$_3$H$_6$ | 5-CF$_3$-pyridin-2-yl | — |
| H-69 | 2-(OCH$_2$C(CH$_3$)=CH$_2$) | 4-CF$_3$ | C$_3$H$_6$ | 5-CF$_3$-pyridin-2-yl | — |
| H-70 | 2-(OCH$_2$$^s$Bu) | 4-CF$_3$ | C$_3$H$_6$ | 5-CF$_3$-pyridin-2-yl | — |
| H-71 | 2-(OCH$_2$CN) | 4-CF$_3$ | C$_3$H$_6$ | 5-CF$_3$-pyridin-2-yl | — |
| H-72 | 2-(OCH(CH$_3$)OCH$_3$) | 4-CF$_3$ | C$_3$H$_6$ | 5-CF$_3$-pyridin-2-yl | — |
| H-73 | 2-(CO$_2$$^i$Pr) | 4-CF$_3$ | C$_3$H$_6$ | 5-CF$_3$-pyridin-2-yl | — |
| H-74 | 2-(CO$_2$Et) | 4-CF$_3$ | C$_3$H$_6$ | 5-CF$_3$-pyridin-2-yl | — |
| H-75 | 2-(OCH$_2$$^i$Pr) | 4-CF$_3$ | C$_3$H$_6$ | 5-CF$_3$-6-Cl-pyridin-2-yl | — |
| H-76 | 2-(OCH$_2$$^i$Pr) | 4-CF$_3$ | C$_3$H$_6$ | 3-CF$_3$-6-Cl-pyridin-2-yl | — |
| H-77 | 2-(OAc) | 4-CF$_3$ | C$_3$H$_6$ | 5-CF$_3$-pyridin-2-yl | — |
| H-78 | 2-(OCH$_2$[2.2-Cl$_2$-3-Ph—$^c$Pr]) | 4-CF$_3$ | C$_3$H$_6$ | 5-CF$_3$-pyridin-2-yl | — |
| H-79 | 2-(OCH$_2$Ac) | 4-CF$_3$ | C$_3$H$_6$ | 5-CF$_3$-pyridin-2-yl | — |
| H-80 | 2-(OCH$_2$CH(OH)CH$_3$) | 4-CF$_3$ | C$_3$H$_6$ | 5-CF$_3$-pyridin-2-yl | — |
| H-81 | 2-(OCH$_2$CH(OCH$_3$)CH$_3$) | 4-CF$_3$ | C$_3$H$_6$ | 5-CF$_3$-pyridin-2-yl | — |
| H-82 | 2-(O$^c$Pen) | 4-CF$_3$ | C$_3$H$_6$ | 5-CF$_3$-pyridin-2-yl | — |
| H-83 | 2-(OCONH$^i$Pr) | 4-CF$_3$ | C$_3$H$_6$ | 5-CF$_3$-pyridin-2-yl | — |
| H-84 | 2-(OSO$_2$CF$_3$) | 4-CF$_3$ | C$_3$H$_6$ | 5-CF$_3$-pyridin-2-yl | — |
| H-85 | 2-Ph | 4-CF$_3$ | C$_3$H$_6$ | 5-CF$_3$-pyridin-2-yl | — |
| H-86 | 2-(pyridin-3-yl) | 4-CF$_3$ | C$_3$H$_6$ | 5-CF$_3$-pyridin-2-yl | — |
| H-87 | 2-(S$^n$Pr) | 4-CF$_3$ | C$_3$H$_6$ | 5-CF$_3$-pyridin-2-yl | — |
| H-88 | 2-(CH$_2$CH=CH$_2$) | 4-CF$_3$ | C$_3$H$_6$ | 5-CF$_3$-pyridin-2-yl | — |
| H-89 | 2-(O$^n$Pr) | 4-Cl | C$_3$H$_6$ | 5-CF$_3$-pyridin-2-yl | — |
| H-90 | 2-(O$^n$Pr) | 4-CF$_3$ | C$_4$H$_8$ | 5-CF$_3$-pyridin-2-yl | — |
| H-91 | 2-(OCH$_2$$^i$Pr) | 4-Cl | CH$_2$OCH$_2$ | 5-CF$_3$-pyridin-2-yl | — |
| H-92 | 2-(OCH$_3$), 3-$^n$Pr | 4-CF$_3$ | C$_3$H$_6$ | 5-CF$_3$-pyridin-2-yl | — |
| H-93 | 2-(OCH(CH$_3$)CH$_2$)-3 | 4-CF$_3$ | C$_3$H$_6$ | 5-CF$_3$-pyridin-2-yl | — |
| H-94 | 2-$^n$Bu | 4-CF$_3$ | C$_3$H$_6$ | 5-CF$_3$-pyridin-2-yl | — |
| H-95 | 2-$^i$Pen | 4-CF$_3$ | C$_3$H$_6$ | 5-CF$_3$-pyridin-2-yl | — |
| H-96 | 2-(CH$_2$CH$_2$C≡CH) | 4-CF$_3$ | C$_3$H$_6$ | 5-CF$_3$-pyridin-2-yl | — |
| H-97 | 2-(CH=N—OH) | 4-CF$_3$ | C$_3$H$_6$ | 5-CF$_3$-pyridin-2-yl | — |
| H-98 | 2-(CH=N—OCH$_3$) | 4-CF$_3$ | C$_3$H$_6$ | 5-CF$_3$-pyridin-2-yl | — |
| H-99 | 2-(CO$^i$Pr) | 4-CF$_3$ | C$_3$H$_6$ | 5-CF$_3$-pyridin-2-yl | — |
| H-100 | 2-(OCH$_2$OAc) | 4-CF$_3$ | C$_3$H$_6$ | 5-CF$_3$-pyridin-2-yl | — |
| H-101 | 2-(OCH$_2$CH(OCH$_3$)$_2$) | 4-CF$_3$ | C$_3$H$_6$ | 5-CF$_3$-pyridin-2-yl | — |
| H-102 | 2-(OCH$_2$CH$_2$SO$_2$CH$_3$) | 4-CF$_3$ | C$_3$H$_6$ | 5-CF$_3$-pyridin-2-yl | — |
| H-103 | 2-(OCH$_2$Ph) | 4-CF$_3$ | C$_3$H$_6$ | 5-CF$_3$-pyridin-2-yl | — |
| H-104 | 2-(OCH$_2$-(pyridine-3-yl)) | 4-CF$_3$ | C$_3$H$_6$ | 5-CF$_3$-pyridin-2-yl | — |
| H-105 | 2-(OCH$_2$-[tetrahydrofuran-2-yl]) | 4-CF$_3$ | C$_3$H$_6$ | 5-CF$_3$-pyridin-2-yl | — |
| H-106 | 2-(OCH$_2$CO$_2$CH$_3$) | 4-CF$_3$ | C$_3$H$_6$ | 5-CF$_3$-pyridin-2-yl | — |
| H-107 | 2-(OCH$_2$CON(CH$_3$)$_2$) | 4-CF$_3$ | C$_3$H$_6$ | 5-CF$_3$-pyridin-2-yl | — |
| H-108 | 2-(OC$_2$H$_4$NO$_2$) | 4-CF$_3$ | C$_3$H$_6$ | 5-CF$_3$-pyridin-2-yl | — |
| H-109 | 2-(OC$_2$H$_4$Si(CH$_3$)$_3$) | 4-CF$_3$ | C$_3$H$_6$ | 5-CF$_3$-pyridin-2-yl | — |
| H-110 | 2-(SCH$_2$CH=CH$_2$) | 4-CF$_3$ | C$_3$H$_6$ | 5-CF$_3$-pyridin-2-yl | — |
| H-111 | 2-(SCH$_2$C≡CH) | 4-CF$_3$ | C$_3$H$_6$ | 5-CF$_3$-pyridin-2-yl | — |
| H-112 | 2-(SO$_2$CH$_3$) | 4-CF$_3$ | C$_3$H$_6$ | 5-CF$_3$-pyridin-2-yl | — |
| H-113 | 2-(SO$_2$CH$_2$CH=CH$_2$) | 4-CF$_3$ | C$_3$H$_6$ | 5-CF$_3$-pyridin-2-yl | — |
| H-114 | 2-(OPh) | 4-CF$_3$ | C$_3$H$_6$ | 5-CF$_3$-pyridin-2-yl | — |
| H-115 | 2-(O-(pyridine-3-yl)) | 4-CF$_3$ | C$_3$H$_6$ | 5-CF$_3$-pyridin-2-yl | — |
| H-116 | 2-NH$_2$ | 4-CF$_3$ | C$_3$H$_6$ | 5-CF$_3$-pyridin-2-yl | — |
| H-117 | 2-(N(CH$_3$)$^i$Pr) | 4-CF$_3$ | C$_3$H$_6$ | 5-CF$_3$-pyridin-2-yl | — |
| H-118 | 2-(NHCH$_2$CH=CH$_2$) | 4-CF$_3$ | C$_3$H$_6$ | 5-CF$_3$-pyridin-2-yl | — |
| H-119 | 2-(NHCH$_2$C≡CH) | 4-CF$_3$ | C$_3$H$_6$ | 5-CF$_3$-pyridin-2-yl | — |
| H-120 | 2-(NHAc) | 4-CF$_3$ | C$_3$H$_6$ | 5-CF$_3$-pyridin-2-yl | — |
| H-121 | 2-(NHSO$_2$CH$_3$) | 4-CF$_3$ | C$_3$H$_6$ | 5-CF$_3$-pyridin-2-yl | — |
| H-122 | 2-(NHSO$_2$Ph) | 4-CF$_3$ | C$_3$H$_6$ | 5-CF$_3$-pyridin-2-yl | — |
| H-123 | 2-(CONH$_2$) | 4-CF$_3$ | C$_3$H$_6$ | 5-CF$_3$-pyridin-2-yl | — |
| H-124 | 2-(O—N=C(CH$_3$)$_2$) | 4-CF$_3$ | C$_3$H$_6$ | 5-CF$_3$-pyridin-2-yl | — |
| H-125 | 2-(SPh) | 4-CF$_3$ | C$_3$H$_6$ | 5-CF$_3$-pyridin-2-yl | — |
| H-126 | 2-(S-(pyridin-3-yl)) | 4-CF$_3$ | C$_3$H$_6$ | 5-CF$_3$-pyridin-2-yl | — |
| H-127 | 2-(CS$^i$Pr) | 4-CF$_3$ | C$_3$H$_6$ | 5-CF$_3$-pyridin-2-yl | — |
| H-128 | 2-(CO(S$^i$Pr)) | 4-CF$_3$ | C$_3$H$_6$ | 5-CF$_3$-pyridin-2-yl | — |

TABLE 1-continued

| No. | $(R^{10})_m$ | $(R^{11})_n$ | A | $Cy^2$-$(R^{20})_p$ | $(R^{21})_r$ |
|---|---|---|---|---|---|
| H-129 | 2-(CS(O$^i$Pr)) | 4-CF$_3$ | C$_3$H$_6$ | 5-CF$_3$-pyridin-2-yl | — |
| H-130 | 2-(CS$_2^i$Pr) | 4-CF$_3$ | C$_3$H$_6$ | 5-CF$_3$-pyridin-2-yl | — |
| H-131 | 2-(Si(CH$_3$)$_3$) | 4-CF$_3$ | C$_3$H$_6$ | 5-CF$_3$-pyridin-2-yl | — |
| H-132 | 2-NO$_2$ | 4-CF$_3$ | C$_3$H$_6$ | 5-CF$_3$-pyridin-2-yl | — |
| H-133 | 2-(OCH$_2$CH$_2$)-3 | 4-CF$_3$ | C$_3$H$_6$ | 5-CF$_3$-pyridin-2-yl | — |
| H-134 | 2-(OCH$_2$CH$_2$O)-3 | 4-CF$_3$ | C$_3$H$_6$ | 5-CF$_3$-pyridin-2-yl | — |
| H-135 | 2-(OCH$_2$O)-3 | 4-CF$_3$ | C$_3$H$_6$ | 5-CF$_3$-pyridin-2-yl | — |
| H-136 | 2-(CH$_2$OCH$_2$CF$_3$) | 4-CF$_3$ | C$_3$H$_6$ | 5-CF$_3$-pyridin-2-yl | — |
| H-137 | 2-(CH$_2$OCH$_2$CN) | 4-CF$_3$ | C$_3$H$_6$ | 5-CF$_3$-pyridin-2-yl | — |
| H-138 | 2-(CH$_2$OCH$_2$OCH$_3$) | 4-CF$_3$ | C$_3$H$_6$ | 5-CF$_3$-pyridin-2-yl | — |
| H-139 | 2-(CH$_2$OCH$_2$O$^c$Pen) | 4-CF$_3$ | C$_3$H$_6$ | 5-CF$_3$-pyridin-2-yl | — |
| H-140 | 2-(CH$_2$OCH$_2$Ac) | 4-CF$_3$ | C$_3$H$_6$ | 5-CF$_3$-pyridin-2-yl | — |
| H-141 | 2-(CH$_2$OCH$_2$CH(OCH$_3$)$_2$) | 4-CF$_3$ | C$_3$H$_6$ | 5-CF$_3$-pyridin-2-yl | — |
| H-142 | 2-(CH$_2$OCH$_2$SO$_2$CH$_3$) | 4-CF$_3$ | C$_3$H$_6$ | 5-CF$_3$-pyridin-2-yl | — |
| H-143 | 2-(CH$_2$OCH$_2$Ph) | 4-CF$_3$ | C$_3$H$_6$ | 5-CF$_3$-pyridin-2-yl | — |
| H-144 | 2-(CH$_2$OCH$_2$-(pyridine-3-yl)) | 4-CF$_3$ | C$_3$H$_6$ | 5-CF$_3$-pyridin-2-yl | — |
| H-145 | 2-(CH$_2$OCH$_2$-[tetrahydrofuran-2-yl]) | 4-CF$_3$ | C$_3$H$_6$ | 5-CF$_3$-pyridin-2-yl | — |
| H-146 | 2-(CH$_2$SCH$_2$CF$_3$) | 4-CF$_3$ | C$_3$H$_6$ | 5-CF$_3$-pyridin-2-yl | — |
| H-147 | 2-(CH$_2$SCH$_2$CN) | 4-CF$_3$ | C$_3$H$_6$ | 5-CF$_3$-pyridin-2-yl | — |
| H-148 | 2-(CH$_2$SCH$_3$) | 4-CF$_3$ | C$_3$H$_6$ | 5-CF$_3$-pyridin-2-yl | — |
| H-149 | 2-(CH$_2$SCH$_2$O$^c$Pen) | 4-CF$_3$ | C$_3$H$_6$ | 5-CF$_3$-pyridin-2-yl | — |
| H-150 | 2-(CH$_2$SCH$_2$Ac) | 4-CF$_3$ | C$_3$H$_6$ | 5-CF$_3$-pyridin-2-yl | — |
| H-151 | 2-(CH$_2$SCH$_2$Ph) | 4-CF$_3$ | C$_3$H$_6$ | 5-CF$_3$-pyridin-2-yl | — |
| H-152 | 2-(CH$_2$SCH$_2$-(pyridine-3-yl)) | 4-CF$_3$ | C$_3$H$_6$ | 5-CF$_3$-pyridin-2-yl | — |
| H-153 | 2-(CH$_2$SCH$_2$-[tetrahydrofuran-2-yl]) | 4-CF$_3$ | C$_3$H$_6$ | 5-CF$_3$-pyridin-2-yl | — |
| H-154 | 2-(CO$_2$CH$_2$[tetrahydrofuran-2-yl]) | 4-CF$_3$ | C$_3$H$_6$ | 5-CF$_3$-pyridin-2-yl | — |
| H-155 | 2-(Spiro[2.2]pent-1-yl) | 4-CF$_3$ | C$_3$H$_6$ | 5-CF$_3$-pyridin-2-yl | — |
| H-156 | 2-(1-CH$_3$-spiro[2.2]pent-1-yl) | 4-CF$_3$ | C$_3$H$_6$ | 5-CF$_3$-pyridin-2-yl | — |
| H-157 | 2-(1-HOCH$_2$-spiro[2.2]pent-1-yl) | 4-CF$_3$ | C$_3$H$_6$ | 5-CF$_3$-pyridin-2-yl | — |
| H-158 | 2-(Spiro[2.2]pent-1-yloxy) | 4-CF$_3$ | C$_3$H$_6$ | 5-CF$_3$-pyridin-2-yl | — |
| H-159 | 2-(Spiro[2.2]pent-1-ylmethoxy) | 4-CF$_3$ | C$_3$H$_6$ | 5-CF$_3$-pyridin-2-yl | — |
| H-160 | 2-(2-$^c$Pr-$^c$Pr) | 4-CF$_3$ | C$_3$H$_6$ | 5-CF$_3$-pyridin-2-yl | — |
| H-161 | 2-(2-$^c$Pr-$^c$PrO) | 4-CF$_3$ | C$_3$H$_6$ | 5-CF$_3$-pyridin-2-yl | — |
| H-162 | 2-(OCH$_2^i$Pr) | 4-CF$_3$ | C$_3$H$_6$ | 5-SF$_5$-pyridin-2-yl | — |
| H-163 | 2-(OCH$_2^c$Pr) | 4-CF$_3$ | C$_3$H$_6$ | 5-SF$_5$-pyridin-2-yl | — |
| H-164 | 2-(CH$_2$OCH(OCH$_3$)CH$_3$) | 4-CF$_3$ | C$_3$H$_6$ | 5-SF$_5$-pyridin-2-yl | — |
| H-165 | 2-(CO$_2^i$Pr) | 4-CF$_3$ | C$_3$H$_6$ | 5-SF$_5$-pyridin-2-yl | — |
| H-166 | 2-(O$^n$Pr) | 4-CF$_3$ | C$_3$H$_6$ | 5-SF$_5$-pyridin-2-yl | — |
| H-167 | 2-(OCH$_2^i$Pr) | 4-CF$_3$ | C$_3$H$_6$ | 5-SF$_5$-pyridin-2-yl | — |
| H-168 | 2-(OCH$_2^c$Pr) | 4-CF$_3$ | C$_3$H$_6$ | 5-SF$_5$-pyridin-2-yl | — |
| H-169 | 2-(CH$_2$OCH(OCH$_3$)CH$_3$) | 4-CF$_3$ | C$_3$H$_6$ | 5-SF$_5$-pyridin-2-yl | — |
| H-170 | 2-(CO$_2^i$Pr) | 4-CF$_3$ | C$_3$H$_6$ | 5-SF$_5$-pyridin-2-yl | — |
| H-171 | 2-(O$^n$Pr) | 4-CF$_3$ | C$_3$H$_6$ | 5-SF$_5$-pyridin-2-yl | — |
| H-172 | 2-(OCH$_2^i$Pr) | 4-SF$_5$ | C$_3$H$_6$ | 5-SF$_5$-pyridin-2-yl | — |
| H-173 | 2-(OCH$_2^c$Pr) | 4-SF$_5$ | C$_3$H$_6$ | 5-SF$_5$-pyridin-2-yl | — |
| H-174 | 2-(CH$_2$OCH(OCH$_3$)CH$_3$) | 4-SF$_5$ | C$_3$H$_6$ | 5-SF$_5$-pyridin-2-yl | — |
| H-175 | 2-(CO$_2^i$Pr) | 4-SF$_5$ | C$_3$H$_6$ | 5-SF$_5$-pyridin-2-yl | — |
| H-176 | 2-(O$^n$Pr) | 4-SF$_5$ | C$_3$H$_6$ | 5-SF$_5$-pyridin-2-yl | — |
| H-177 | 2-(OCH$_2^i$Pr) | 4-SF$_5$ | C$_3$H$_6$ | 5-SF$_5$-pyridin-2-yl | — |
| H-178 | 2-(OCH$_2^c$Pr) | 4-SF$_5$ | C$_3$H$_6$ | 5-SF$_5$-pyridin-2-yl | — |
| H-179 | 2-(CH$_2$OCH(OCH$_3$)CH$_3$) | 4-SF$_5$ | C$_3$H$_6$ | 5-SF$_5$-pyridin-2-yl | — |
| H-180 | 2-(CO$_2^i$Pr) | 4-SF$_5$ | C$_3$H$_6$ | 5-SF$_5$-pyridin-2-yl | — |
| H-181 | 2-(O$^n$Pr) | 4-SF$_5$ | C$_3$H$_6$ | 5-SF$_5$-pyridin-2-yl | — |
| H-182 | 2-(OCH$_2^i$Pr) | 4-CN | C$_3$H$_6$ | 5-CF$_3$-pyridin-2-yl | — |
| H-183 | 2-(OCH$_2^c$Pr) | 4-CN | C$_3$H$_6$ | 5-CF$_3$-pyridin-2-yl | — |
| H-184 | 2-(CH$_2$OCH(OCH$_3$)CH$_3$) | 4-CN | C$_3$H$_6$ | 5-CF$_3$-pyridin-2-yl | — |
| H-185 | 2-(CO$_2^i$Pr) | 4-CN | C$_3$H$_6$ | 5-CF$_3$-pyridin-2-yl | — |
| H-186 | 2-(O$^n$Pr) | 4-CN | C$_3$H$_6$ | 5-CF$_3$-pyridin-2-yl | — |
| H-187 | 2-(OCH$_2^i$Pr) | 4-CF$_3$ | C$_3$H$_6$ | 5-Cl-pyridin-2-yl | — |
| H-188 | 2-(OCH$_2^c$Pr) | 4-CF$_3$ | C$_3$H$_6$ | 5-Cl-pyridin-2-yl | — |
| H-189 | 2-(CH$_2$OCH(OCH$_3$)CH$_3$) | 4-CF$_3$ | C$_3$H$_6$ | 5-Cl-pyridin-2-yl | — |
| H-190 | 2-(CO$_2^i$Pr) | 4-CF$_3$ | C$_3$H$_6$ | 5-Cl-pyridin-2-yl | — |
| H-191 | 2-(O$^n$Br) | 4-CF$_3$ | C$_3$H$_6$ | 5-Cl-pyridin-2-yl | — |
| H-192 | 2-$^n$Bu | 4-Br | C$_3$H$_6$ | 5-CF$_3$-pyridin-2-yl | — |
| H-193 | 2-(CH$_2$CH=CH$_2$) | 4-Br | C$_3$H$_6$ | 5-CF$_3$-pyridin-2-yl | — |

TABLE 1-continued

| No. | $(R^{10})_m$ | $(R^{11})_n$ | A | $Cy^2$-$(R^{20})_p$ | $(R^{21})_r$ |
|---|---|---|---|---|---|
| H-194 | 2-($CH_2O^iPr$) | 4-Br | $C_3H_6$ | 5-$CF_3$-pyridin-2-yl- | — |
| H-195 | 2-($CH_2OEt$) | 4-Br | $C_3H_6$ | 5-$CF_3$-pyridin-2-yl | — |
| H-196 | 2-(OEt) | 4-Br | $C_3H_6$ | 5-$CF_3$-pyridin-2-yl | — |
| H-197 | 2-($O^nPr$) | 4-Br | $C_3H_6$ | 5-$CF_3$-pyridin-2-yl | — |
| H-198 | 2-($O^iPr$) | 4-Br | $C_3H_6$ | 5-$CF_3$-pyridin-2-yl | — |
| H-199 | 2-($O^nBu$) | 4-Br | $C_3H_6$ | 5-$CF_3$-pyridin-2-yl | — |
| H-200 | 2-($O^sBu$) | 4-Br | $C_3H_6$ | 5-$CF_3$-pyridin-2-yl | — |
| H-201 | 2-($OCH_2^sBu$) | 4-Br | $C_3H_6$ | 5-$CF_3$-pyridin-2-yl | — |
| H-202 | 2-($OCH_2^tBu$) | 4-Br | $C_3H_6$ | 5-$CF_3$-pyridin-2-yl | — |
| H-203 | 2-($OCH_2CF_3$) | 4-Br | $C_3H_6$ | 5-$CF_3$-pyridin-2-yl | — |
| H-204 | 2-($OCH_2CN$) | 4-Br | $C_3H_6$ | 5-$CF_3$-pyridin-2-yl | — |
| H-205 | 2-($OCH_2CH(OH)CH_3$) | 4-Br | $C_3H_6$ | 5-$CF_3$-pyridin-2-yl | — |
| H-206 | 2-($OCH_2CH(OCH_3)CH_3$) | 4-Br | $C_3H_6$ | 5-$CF_3$-pyridin-2-yl | — |
| H-207 | 2-($OCH_2OCH_3$) | 4-Br | $C_3H_6$ | 5-$CF_3$-pyridin-2-yl | — |
| H-208 | 2-($OCH(CH_3)OCH_3$) | 4-Br | $C_3H_6$ | 5-$CF_3$-pyridin-2-yl | — |
| H-209 | 2-($OCH_2Ac$) | 4-Br | $C_3H_6$ | 5-$CF_3$-pyridin-2-yl | — |
| H-210 | 2-($OCH_2CH=CH_2$) | 4-Br | $C_3H_6$ | 5-$CF_3$-pyridin-2-yl | — |
| H-211 | 2-($OCH_2CH=C(CH_3)_2$) | 4-Br | $C_3H_6$ | 5-$CF_3$-pyridin-2-yl | — |
| H-212 | 2-($OCH_2C\equiv CH$) | 4-Br | $C_3H_6$ | 5-$CF_3$-pyridin-2-yl | — |
| H-213 | 2-(OAc) | 4-Br | $C_3H_6$ | 5-$CF_3$-pyridin-2-yl | — |
| H-214 | 2-($OCO_2^iPr$) | 4-Br | $C_3H_6$ | 5-$CF_3$-pyridin-2-yl | — |
| H-215 | 2-($OCONH^iPr$) | 4-Br | $C_3H_6$ | 5-$CF_3$-pyridin-2-yl | — |
| H-216 | 2-($OSO_2CF_3$) | 4-Br | $C_3H_6$ | 5-$CF_3$-pyridin-2-yl | — |
| H-217 | 2-($NHCH_2^iPr$) | 4-Br | $C_3H_6$ | 5-$CF_3$-pyridin-2-yl | — |
| H-218 | 2-($CO_2Et$) | 4-Br | $C_3H_6$ | 5-$CF_3$-pyridin-2-yl | — |
| H-219 | 2-($S^nPr$) | 4-Br | $C_3H_6$ | 5-$CF_3$-pyridin-2-yl | — |
| H-220 | 2-([1,3]dioxolan-2-yl) | 4-Br | $C_3H_6$ | 5-$CF_3$-pyridin-2-yl | — |
| H-221 | 2-($OCH_2^iPr$) | 4-$CH(CF_3)_2$ | $C_3H_6$ | 5-$CF_3$-pyridin-2-yl | — |
| H-222 | 2-($OCH_2^cPr$) | 4-$CH(CF_3)_2$ | $C_3H_6$ | 5-$CF_3$-Pyridin-2-yl | — |
| H-223 | 2-($CH_2OCH(OCH_3)CH_3$) | 4-$CF(CF_3)_2$ | $C_3H_6$ | 5-$CF_3$-Pyridin-2-yl | — |
| H-224 | 2-($CO_2^iPr$) | 4-$CF(CF_3)_2$ | $C_3H_6$ | 5-$CF_3$-pyridin-2-yl | — |
| H-225 | 2-($O^nPr$) | 4-$C(CF_3)_2OCH_3$ | $C_3H_6$ | 5-$CF_3$-pyridin-2-yl | — |
| H-226 | 2-$^nBu$ | 4-$CF_3$ | $CH_2N(CH_3)CH_2$ | 5-$CF_3$-pyridin-2-yl | — |
| H-227 | 2-($CH_2CH=CH_2$) | 4-$CF_3$ | $CH_2N(CH_3)CH_2$ | 5-$CF_3$-pyridin-2-yl | — |
| H-228 | 2-($CH_2O^iPr$) | 4-$CF_3$ | $CH_2N(CH_3)CH_2$ | 5-$CF_3$-pyridin-2-yl | — |
| H-229 | 2-($CH_2OEt$) | 4-$CF_3$ | $CH_2N(CH_3)CH_2$ | 5-$CF_3$-pyridin-2-yl | — |
| H-230 | 2-(OEt) | 4-$CF_3$ | $CH_2N(CH_3)CH_2$ | 5-$CF_3$-pyridin-2-yl | — |
| H-231 | 2-($O^nPr$) | 4-$CF_3$ | $CH_2N(CH_3)CH_2$ | 5-$CF_3$-pyridin-2-yl | — |
| H-232 | 2-($O^iPr$) | 4-$CF_3$ | $CH_2N(CH_3)CH_2$ | 5-$CF_3$-pyridin-2-yl | — |
| H-233 | 2-($O^nBu$) | 4-$CF_3$ | $CH_2N(CH_3)CH_2$ | 5-$CF_3$-pyridin-2-yl | — |
| H-234 | 2-($O^sBu$) | 4-$CF_3$ | $CH_2N(CH_3)CH_2$ | 5-$CF_3$-pyridin-2-yl | — |
| H-235 | 2-($OCH_2^iPr$) | 4-$CF_3$ | $CH_2N(CH_3)CH_2$ | 5-$CF_3$-pyridin-2-yl | — |
| H-236 | 2-($OCH_2^cPr$) | 4-$CF_3$ | $CH_2N(CH_3)CH_2$ | 5-$CF_3$-pyridin-2-yl | — |
| H-237 | 2-($OCH_2^sBu$) | 4-$CF_3$ | $CH_2N(CH_3)CH_2$ | 5-$CF_3$-pyridin-2-yl | — |
| H-238 | 2-($OCH_2^tBu$) | 4-$CF_3$ | $CH_2N(CH_3)CH_2$ | 5-$CF_3$-pyridin-2-yl | — |
| H-239 | 2-($OCH_2CF_3$) | 4-$CF_3$ | $CH_2N(CH_3)CH_2$ | 5-$CF_3$-pyridin-2-yl | — |
| H-240 | 2-($OCH_2CN$) | 4-$CF_3$ | $CH_2N(CH_3)CH_2$ | 5-$CF_3$-pyridin-2-yl | — |
| H-241 | 2-($OCH_2CH(OH)CH_3$) | 4-$CF_3$ | $CH_2N(CH_3)CH_2$ | 5-$CF_3$-pyridin-2-yl | — |
| H-242 | 2-($OCH_2CH(OCH_3)CH_3$) | 4-$CF_3$ | $CH_2N(CH_3)CH_2$ | 5-$CF_3$-pyridin-2-yl | — |
| H-243 | 2-($OCH_2OCH_3$) | 4-$CF_3$ | $CH_2N(CH_3)CH_2$ | 5-$CF_3$-pyridin-2-yl | — |
| H-244 | 2-($OCH(CH_3)OCH_3$) | 4-$CF_3$ | $CH_2N(CH_3)CH_2$ | 5-$CF_3$-pyridin-2-yl | — |
| H-245 | 2-($OCH_2Ac$) | 4-$CF_3$ | $CH_2N(CH_3)CH_2$ | 5-$CF_3$-pyridin-2-yl | — |
| H-246 | 2-($OCH_2CH=CH_2$) | 4-$CF_3$ | $CH_2N(CH_3)CH_2$ | 5-$CF_3$-pyridin-2-yl | — |
| H-247 | 2-($OCH_2CH=C(CH_3)_2$) | 4-$CF_3$ | $CH_2N(CH_3)CH_2$ | 5-$CF_3$-pyridin-2-yl | — |
| H-248 | 2-($OCH_2C\equiv CH$) | 4-$CF_3$ | $CH_2N(CH_3)CH_2$ | 5-$CF_3$-pyridin-2-yl | — |
| H-249 | 2-(OAc) | 4-$CF_3$ | $CH_2N(CH_3)CH_2$ | 5-$CF_3$-pyridin-2-yl | — |
| H-250 | 2-($OCO_2^iPr$) | 4-$CF_3$ | $CH_2N(CH_3)CH_2$ | 5-$CF_3$-pyridin-2-yl | — |
| H-251 | 2-($OCONH^iPr$) | 4-$CF_3$ | $CH_2N(CH_3)CH_2$ | 5-$CF_3$-pyridin-2-yl | — |
| H-252 | 2-($OSO_2CF_3$) | 4-$CF_3$ | $CH_2N(CH_3)CH_2$ | 5-$CF_3$-pyridin-2-yl | — |
| H-253 | 2-($NHCH_2^iPr$) | 4-$CF_3$ | $CH_2N(CH_3)CH_2$ | 5-$CF_3$-pyridin-2-yl | — |
| H-254 | 2-($CO_2Et$) | 4-$CF_3$ | $CH_2N(CH_3)CH_2$ | 5-$CF_3$-pyridin-2-yl | — |
| H-255 | 2-($CO_2^iPr$) | 4-$CF_3$ | $CH_2N(CH_3)CH_2$ | 5-$CF_3$-pyridin-2-yl | — |
| H-256 | 2-($S^nPr$) | 4-$CF_3$ | $CH_2N(CH_3)CH_2$ | 5-$CF_3$-pyridin-2-yl | — |
| H-257 | 2-([1,3]dioxolan-2-yl) | 4-$CF_3$ | $CH_2N(CH_3)CH_2$ | 5-$CF_3$-pyridin-2-yl | — |
| H-258 | 2-$^nBu$ | 4-$CF_3$ | $CH_2OCH_2$ | 5-$CF_3$-pyridin-2-yl | — |
| H-259 | 2-($CH_2CH=CH_2$) | 4-$CF_3$ | $CH_2OCH_2$ | 5-$CF_3$-pyridin-2-yl | — |
| H-260 | 2-($CH_2O^iPr$) | 4-$CF_3$ | $CH_2OCH_2$ | 5-$CF_3$-pyridin-2-yl | — |
| H-261 | 2-($CH_2OEt$) | 4-$CF_3$ | $CH_2OCH_2$ | 5-$CF_3$-pyridin-2-yl | — |
| H-262 | 2-(OEt) | 4-$CF_3$ | $CH_2OCH_2$ | 5-$CF_3$-pyridin-2-yl | — |
| H-263 | 2-($O^nPr$) | 4-$CF_3$ | $CH_2OCH_2$ | 5-$CF_3$-pyridin-2-yl | — |
| H-264 | 2-($O^iPr$) | 4-$CF_3$ | $CH_2OCH_2$ | 5-$CF_3$-pyridin-2-yl | — |
| H-265 | 2-($O^nBu$) | 4-$CF_3$ | $CH_2OCH_2$ | 5-$CF_3$-pyridin-2-yl | — |
| H-266 | 2-($O^sBu$) | 4-$CF_3$ | $CH_2OCH_2$ | 5-$CF_3$-pyridin-2-yl | — |
| H-267 | 2-($OCH_2^sBu$) | 4-$CF_3$ | $CH_2OCH_2$ | 5-$CF_3$-pyridin-2-yl | — |
| H-268 | 2-($OCH_2^tBu$) | 4-$CF_3$ | $CH_2OCH_2$ | 5-$CF_3$-pyridin-2-yl | — |
| H-269 | 2-($OCH_2CF_3$) | 4-$CF_3$ | $CH_2OCH_2$ | 5-$CF_3$-pyridin-2-yl | — |

TABLE 1-continued

| No. | $(R^{10})_m$ | $(R^{11})_n$ | A | $Cy^2$-$(R^{20})_p$ | $(R^{21})_r$ |
|---|---|---|---|---|---|
| H-270 | 2-(OCH$_2$CN) | 4-CF$_3$ | CH$_2$OCH$_2$ | 5-CF$_3$-pyridin-2-yl | — |
| H-271 | 2-(OCH$_2$CH(OH)CH$_3$) | 4-CF$_3$ | CH$_2$OCH$_2$ | 5-CF$_3$-pyridin-2-yl | — |
| H-272 | 2-(OCH$_2$CH(OCH$_3$)CH$_3$) | 4-CF$_3$ | CH$_2$OCH$_2$ | 5-CF$_3$-pyridin-2-yl | — |
| H-273 | 2-(OCH$_2$OCH$_3$) | 4-CF$_3$ | CH$_2$OCH$_2$ | 5-CF$_3$-pyridin-2-yl | — |
| H-274 | 2-(OCH(CH$_3$)OCH$_3$) | 4-CF$_3$ | CH$_2$OCH$_2$ | 5-CF$_3$-pyridin-2-yl | — |
| H-275 | 2-(OCH$_2$Ac) | 4-CF$_3$ | CH$_2$OCH$_2$ | 5-CF$_3$-pyridin-2-yl | — |
| H-276 | 2-(OCH$_2$CH=CH$_2$) | 4-CF$_3$ | CH$_2$OCH$_2$ | 5-CF$_3$-pyridin-2-yl | — |
| H-277 | 2-(OCH$_2$CH=C(CH$_3$)$_2$) | 4-CF$_3$ | CH$_2$OCH$_2$ | 5-CF$_3$-pyridin-2-yl | — |
| H-278 | 2-(OCH$_2$C≡CH) | 4-CF$_3$ | CH$_2$OCH$_2$ | 5-CF$_3$-pyridin-2-yl | — |
| H-279 | 2-(OAc) | 4-CF$_3$ | CH$_2$OCH$_2$ | 5-CF$_3$-pyridin-2-yl | — |
| H-280 | 2-(OCO$_2^i$Pr) | 4-CF$_3$ | CH$_2$OCH$_2$ | 5-CF$_3$-pyridin-2-yl | — |
| H-281 | 2-(OCONH$^i$Pr) | 4-CF$_3$ | CH$_2$OCH$_2$ | 5-CF$_3$-pyridin-2-yl | — |
| H-282 | 2-(OSO$_2$CF$_3$) | 4-CF$_3$ | CH$_2$OCH$_2$ | 5-CF$_3$-pyridin-2-yl | — |
| H-283 | 2-(NHCH$_2^i$Pr) | 4-CF$_3$ | CH$_2$OCH$_2$ | 5-CF$_3$-pyridin-2-yl | — |
| H-284 | 2-(CO$_2$Et) | 4-CF$_3$ | CH$_2$OCH$_2$ | 5-CF$_3$-pyridin-2-yl | — |
| H-285 | 2-(S$^n$Pr) | 4-CF$_3$ | CH$_2$OCH$_2$ | 5-CF$_3$-pyridin-2-yl | — |
| H-286 | 2-([1,3]dioxolan-2-yl) | 4-CF$_3$ | CH$_2$OCH$_2$ | 5-CF$_3$-pyridin-2-yl | — |
| H-287 | 2-$^n$Bu | 4-CF$_3$ | CH$_2$CF$_2$CH$_2$ | 5-CF$_3$-pyridin-2-yl | — |
| H-288 | 2-(CH$_2$CH=CH$_2$) | 4-CF$_3$ | CH$_2$CF$_2$CH$_2$ | 5-CF$_3$-pyridin-2-yl | — |
| H-289 | 2-(CH$_2$O$^i$Pr) | 4-CF$_3$ | CH$_2$CF$_2$CH$_2$ | 5-CF$_3$-pyridin-2-yl | — |
| H-290 | 2-(CH$_2$OEt) | 4-CF$_3$ | CH$_2$CF$_2$CH$_2$ | 5-CF$_3$-pyridin-2-yl | — |
| H-291 | 2-(OEt) | 4-CF$_3$ | CH$_2$CF$_2$CH$_2$ | 5-CF$_3$-pyridin-2-yl | — |
| H-292 | 2-(O$^n$Pr) | 4-CF$_3$ | CH$_2$CF$_2$CH$_2$ | 5-CF$_3$-pyridin-2-yl | — |
| H-293 | 2-(O$^i$Pr) | 4-CF$_3$ | CH$_2$CF$_2$CH$_2$ | 5-CF$_3$-pyridin-2-yl | — |
| H-294 | 2-(O$^n$Bu) | 4-CF$_3$ | CH$_2$CF$_2$CH$_2$ | 5-CF$_3$-pyridin-2-yl | — |
| H-295 | 2-(O$^s$Bu) | 4-CF$_3$ | CH$_2$CF$_2$CH$_2$ | 5-CF$_3$-pyridin-2-yl | — |
| H-296 | 2-(OCH$_2^i$Pr) | 4-CF$_3$ | CH$_2$CF$_2$CH$_2$ | 5-CF$_3$-pyridin-2-yl | — |
| H-297 | 2-(OCH$_2^c$Pr) | 4-CF$_3$ | CH$_2$CF$_2$CH$_2$ | 5-CF$_3$-pyridin-2-yl | — |
| H-298 | 2-(OCH$_2^s$Bu) | 4-CF$_3$ | CH$_2$CF$_2$CH$_2$ | 5-CF$_3$-pyridin-2-yl | — |
| H-299 | 2-(OCH$_2^t$Bu) | 4-CF$_3$ | CH$_2$CF$_2$CH$_2$ | 5-CF$_3$-pyridin-2-yl | — |
| H-300 | 2-(OCH$_2$CF$_3$) | 4-CF$_3$ | CH$_2$CF$_2$CH$_2$ | 5-CF$_3$-pyridin-2-yl | — |
| H-301 | 2-(OCH$_2$CN) | 4-CF$_3$ | CH$_2$CF$_2$CH$_2$ | 5-CF$_3$-pyridin-2-yl | — |
| H-302 | 2-(OCH$_2$CH(OH)CH$_3$) | 4-CF$_3$ | CH$_2$CF$_2$CH$_2$ | 5-CF$_3$-pyridin-2-yl | — |
| H-303 | 2-(OCH$_2$CH(OCH$_3$)CH$_3$) | 4-CF$_3$ | CH$_2$CF$_2$CH$_2$ | 5-CF$_3$-pyridin-2-yl | — |
| H-304 | 2-(OCH$_2$OCH$_3$) | 4-CF$_3$ | CH$_2$CF$_2$CH$_2$ | 5-CF$_3$-pyridin-2-yl | — |
| H-305 | 2-(OCH(CH$_3$)OCH$_3$) | 4-CF$_3$ | CH$_2$CF$_2$CH$_2$ | 5-CF$_3$-pyridin-2-yl | — |
| H-306 | 2-(OCH$_2$Ac) | 4-CF$_3$ | CH$_2$CF$_2$CH$_2$ | 5-CF$_3$-pyridin-2-yl | — |
| H-307 | 2-(OCH$_2$CH=CH$_2$) | 4-CF$_3$ | CH$_2$CF$_2$CH$_2$ | 5-CF$_3$-pyridin-2-yl | — |
| H-308 | 2-(OCH$_2$CH=C(CH$_3$)$_2$) | 4-CF$_3$ | CH$_2$CF$_2$CH$_2$ | 5-CF$_3$-pyridin-2-yl | — |
| H-309 | 2-(OCH$_2$C≡CH) | 4-CF$_3$ | CH$_2$CF$_2$CH$_2$ | 5-CF$_3$-pyridin-2-yl | — |
| H-310 | 2-(OAc) | 4-CF$_3$ | CH$_2$CF$_2$CH$_2$ | 5-CF$_3$-pyridin-2-yl | — |
| H-311 | 2-(OCO$_2^i$Pr) | 4-CF$_3$ | CH$_2$CF$_2$CH$_2$ | 5-CF$_3$-pyridin-2-yl | — |
| H-312 | 2-(OCONH$^i$Pr) | 4-CF$_3$ | CH$_2$CF$_2$CH$_2$ | 5-CF$_3$-pyridin-2-yl | — |
| H-313 | 2-(OSO$_2$CF$_3$) | 4-CF$_3$ | CH$_2$CF$_2$CH$_2$ | 5-CF$_3$-pyridin-2-yl | — |
| H-314 | 2-(NHCH$_2^i$Pr) | 4-CF$_3$ | CH$_2$CF$_2$CH$_2$ | 5-CF$_3$-pyridin-2-yl | — |
| H-315 | 2-(CO$_2$Et) | 4-CF$_3$ | CH$_2$CF$_2$CH$_2$ | 5-CF$_3$-pyridin-2-yl | — |
| H-316 | 2-(CO$_2^i$Pr) | 4-CF$_3$ | CH$_2$CF$_2$CH$_2$ | 5-CF$_3$-pyridin-2-yl | — |
| H-317 | 2-(S$^n$Pr) | 4-CF$_3$ | CH$_2$CF$_2$CH$_2$ | 5-CF$_3$-pyridin-2-yl | — |
| H-318 | 2-([1,3]dioxolan-2-yl) | 4-CF$_3$ | CH$_2$CF$_2$CH$_2$ | 5-CF$_3$-pyridin-2-yl | — |
| H-319 | 2-$^n$Bu | 4-CF$_3$ | CH$_2$SCH$_2$ | 5-CF$_3$-pyridin-2-yl | — |
| H-320 | 2-(CH$_2$CH=CH$_2$) | 4-CF$_3$ | CH$_2$SCH$_2$ | 5-CF$_3$-pyridin-2-yl | — |
| H-321 | 2-(CH$_2$O$^i$Pr) | 4-CF$_3$ | CH$_2$SCH$_2$ | 5-CF$_3$-pyridin-2-yl | — |
| H-322 | 2-(CH$_2$OEt) | 4-CF$_3$ | CH$_2$SCH$_2$ | 5-CF$_3$-pyridin-2-yl | — |
| H-323 | 2-(OEt) | 4-CF$_3$ | CH$_2$SCH$_2$ | 5-CF$_3$-pyridin-2-yl | — |
| H-324 | 2-(O$^n$Pr) | 4-CF$_3$ | CH$_2$SCH$_2$ | 5-CF$_3$-pyridin-2-yl | — |
| H-325 | 2-(O$^i$Pr) | 4-CF$_3$ | CH$_2$SCH$_2$ | 5-CF$_3$-pyridin-2-yl | — |
| H-326 | 2-(O$^n$Bu) | 4-CF$_3$ | CH$_2$SCH$_2$ | 5-CF$_3$-pyridin-2-yl | — |
| H-327 | 2-(O$^s$Bu) | 4-CF$_3$ | CH$_2$SCH$_2$ | 5-CF$_3$-pyridin-2-yl | — |
| H-328 | 2-(OCH$_2^s$Bu) | 4-CF$_3$ | CH$_2$SCH$_2$ | 5-CF$_3$-pyridin-2-yl | — |
| H-329 | 2-(OCH$_2^t$Bu) | 4-CF$_3$ | CH$_2$SCH$_2$ | 5-CF$_3$-pyridin-2-yl | — |
| H-330 | 2-(OCH$_2$CF$_3$) | 4-CF$_3$ | CH$_2$SCH$_2$ | 5-CF$_3$-pyridin-2-yl | — |
| H-331 | 2-(OCH$_2$CN) | 4-CF$_3$ | CH$_2$SCH$_2$ | 5-CF$_3$-pyridin-2-yl | — |
| H-332 | 2-(OCH$_2$CH(OH)CH$_3$) | 4-CF$_3$ | CH$_2$SCH$_2$ | 5-CF$_3$-pyridin-2-yl | — |
| H-333 | 2-(OCH$_2$CH(OCH$_3$)CH$_3$) | 4-CF$_3$ | CH$_2$SCH$_2$ | 5-CF$_3$-pyridin-2-yl | — |
| H-334 | 2-(OCH$_2$OCH$_3$) | 4-CF$_3$ | CH$_2$SCH$_2$ | 5-CF$_3$-pyridin-2-yl | — |
| H-335 | 2-(OCH(CH$_3$)OCH$_3$) | 4-CF$_3$ | CH$_2$SCH$_2$ | 5-CF$_3$-pyridin-2-yl | — |
| H-336 | 2-(OCH$_2$Ac) | 4-CF$_3$ | CH$_2$SCH$_2$ | 5-CF$_3$-pyridin-2-yl | — |
| H-337 | 2-(OCH$_2$CH=CH$_2$) | 4-CF$_3$ | CH$_2$SCH$_2$ | 5-CF$_3$-pyridin-2-yl | — |
| H-338 | 2-(OCH$_2$CH=C(CH$_3$)$_2$) | 4-CF$_3$ | CH$_2$SCH$_2$ | 5-CF$_3$-pyridin-2-yl | — |
| H-339 | 2-(OCH$_2$C≡CH) | 4-CF$_3$ | CH$_2$SCH$_2$ | 5-CF$_3$-pyridin-2-yl | — |
| H-340 | 2-(OAc) | 4-CF$_3$ | CH$_2$SCH$_2$ | 5-CF$_3$-pyridin-2-yl | — |
| H-341 | 2-(OCO$_2^i$Pr) | 4-CF$_3$ | CH$_2$SCH$_2$ | 5-CF$_3$-pyridin-2-yl | — |
| H-342 | 2-(OCONH$^i$Pr) | 4-CF$_3$ | CH$_2$SCH$_2$ | 5-CF$_3$-pyridin-2-yl | — |
| H-343 | 2-(OSO$_2$CF$_3$) | 4-CF$_3$ | CH$_2$SCH$_2$ | 5-CF$_3$-pyridin-2-yl | — |
| H-344 | 2-(NHCH$_2^i$Pr) | 4-CF$_3$ | CH$_2$SCH$_2$ | 5-CF$_3$-pyridin-2-yl | — |
| H-345 | 2-(CO$_2$Et) | 4-CF$_3$ | CH$_2$SCH$_2$ | 5-CF$_3$-pyridin-2-yl | — |

TABLE 1-continued

| No. | $(R^{10})_m$ | $(R^{11})_n$ | A | $Cy^2$-$(R^{20})_p$ | $(R^{21})_r$ |
|---|---|---|---|---|---|
| H-346 | 2-($S^nPr$) | 4-$CF_3$ | $CH_2SCH_2$ | 5-$CF_3$-pyridin-2-yl | — |
| H-347 | 2-([1,3]dioxolan-2-yl) | 4-$CF_3$ | $CH_2SCH_2$ | 5-$CF_3$-pyridin-2-yl | — |
| H-348 | 2-$^nBu$ | 4-$CF_3$ | $CH_2C(CH_3)_2CH_2$ | 5-$CF_3$-pyridin-2-yl | — |
| H-349 | 2-($CH_2CH=CH_2$) | 4-$CF_3$ | $CH_2C(CH_3)_2CH_2$ | 5-$CF_3$-pyridin-2-yl | — |
| H-350 | 2-($CH_2O^iPr$) | 4-$CF_3$ | $CH_2C(CH_3)_2CH_2$ | 5-$CF_3$-pyridin-2-yl | — |
| H-351 | 2-($CH_2OEt$) | 4-$CF_3$ | $CH_2C(CH_3)_2CH_2$ | 5-$CF_3$-pyridin-2-yl | — |
| H-352 | 2-(OEt) | 4-$CF_3$ | $CH_2C(CH_3)_2CH_2$ | 5-$CF_3$-pyridin-2-yl | — |
| H-353 | 2-($O^nPr$) | 4-$CF_3$ | $CH_2C(CH_3)_2CH_2$ | 5-$CF_3$-pyridin-2-yl | — |
| H-354 | 2-($O^iPr$) | 4-$CF_3$ | $CH_2C(CH_3)_2CH_2$ | 5-$CF_3$-pyridin-2-yl | — |
| H-355 | 2-($O^nBu$) | 4-$CF_3$ | $CH_2C(CH_3)_2CH_2$ | 5-$CF_3$-pyridin-2-yl | — |
| H-356 | 2-($O^sBu$) | 4-$CF_3$ | $CH_2C(CH_3)_2CH_2$ | 5-$CF_3$-pyridin-2-yl | — |
| H-357 | 2-($OCH_2^iPr$) | 4-$CF_3$ | $CH_2C(CH_3)_2CH_2$ | 5-$CF_3$-pyridin-2-yl | — |
| H-358 | 2-($OCH_2^cPr$) | 4-$CF_3$ | $CH_2C(CH_3)_2CH_2$ | 5-$CF_3$-pyridin-2-yl | — |
| H-359 | 2-($OCH_2^sBu$) | 4-$CF_3$ | $CH_2C(CH_3)_2CH_2$ | 5-$CF_3$-pyridin-2-yl | — |
| H-360 | 2-($OCH_2^tBu$) | 4-$CF_3$ | $CH_2C(CH_3)_2CH_2$ | 5-$CF_3$-pyridin-2-yl | — |
| H-361 | 2-($OCH_2CF_3$) | 4-$CF_3$ | $CH_2C(CH_3)_2CH_2$ | 5-$CF_3$-pyridin-2-yl | — |
| H-362 | 2-($OCH_2CN$) | 4-$CF_3$ | $CH_2C(CH_3)_2CH_2$ | 5-$CF_3$-pyridin-2-yl | — |
| H-363 | 2-($OCH_2CH(OH)CH_3$) | 4-$CF_3$ | $CH_2C(CH_3)_2CH_2$ | 5-$CF_3$-pyridin-2-yl | — |
| H-364 | 2-($OCH_2CH(OCH_3)CH_3$) | 4-$CF_3$ | $CH_2C(CH_3)_2CH_2$ | 5-$CF_3$-pyridin-2-yl | — |
| H-365 | 2-($OCH_2OCH_3$) | 4-$CF_3$ | $CH_2C(CH_3)_2CH_2$ | 5-$CF_3$-pyridin-2-yl | — |
| H-366 | 2-($OCH(CH_3)OCH_3$) | 4-$CF_3$ | $CH_2C(CH_3)_2CH_2$ | 5-$CF_3$-pyridin-2-yl | — |
| H-367 | 2-($OCH_2Ac$) | 4-$CF_3$ | $CH_2C(CH_3)_2CH_2$ | 5-$CF_3$-pyridin-2-yl | — |
| H-368 | 2-($OCH_2CH=CH_2$) | 4-$CF_3$ | $CH_2C(CH_3)_2CH_2$ | 5-$CF_3$-pyridin-2-yl | — |
| H-369 | 2-($OCH_2CH=C(CH_3)_2$) | 4-$CF_3$ | $CH_2C(CH_3)_2CH_2$ | 5-$CF_3$-pyridin-2-yl | — |
| H-370 | 2-($OCH_2C\equiv CH$) | 4-$CF_3$ | $CH_2C(CH_3)_2CH_2$ | 5-$CF_3$-pyridin-2-yl | — |
| H-371 | 2-(OAc) | 4-$CF_3$ | $CH_2C(CH_3)_2CH_2$ | 5-$CF_3$-pyridin-2-yl | — |
| H-372 | 2-($OCO_2^iPr$) | 4-$CF_3$ | $CH_2C(CH_3)_2CH_2$ | 5-$CF_3$-pyridin-2-yl | — |
| H-373 | 2-($OCONH^iPr$) | 4-$CF_3$ | $CH_2C(CH_3)_2CH_2$ | 5-$CF_3$-pyridin-2-yl | — |
| H-374 | 2-($OSO_2CF_3$) | 4-$CF_3$ | $CH_2C(CH_3)_2CH_2$ | 5-$CF_3$-pyridin-2-yl | — |
| H-375 | 2-($NHCH_2^iPr$) | 4-$CF_3$ | $CH_2C(CH_3)_2CH_2$ | 5-$CF_3$-pyridin-2-yl | — |
| H-376 | 2-($CO_2Et$) | 4-$CF_3$ | $CH_2C(CH_3)_2CH_2$ | 5-$CF_3$-pyridin-2-yl | — |
| H-377 | 2-($CO_2^iPr$) | 4-$CF_3$ | $CH_2C(CH_3)_2CH_2$ | 5-$CF_3$-pyridin-2-yl | — |
| H-378 | 2-($S^nPr$) | 4-$CF_3$ | $CH_2C(CH_3)_2CH_2$ | 5-$CF_3$-pyridin-2-yl | — |
| H-379 | 2-([1,3]dioxolan-2-yl) | 4-$CF_3$ | $CH_2C(CH_3)_2CH_2$ | 5-$CF_3$-pyridin-2-yl | — |

[Chemical formula 34]

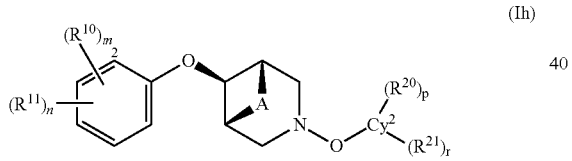

(Ih)

TABLE 2

| No. | $(R^{10})_m$ | $(R^{11})_n$ | A | $Cy^2$-$(R^{20})_p$ | $(R^{21})_r$ |
|---|---|---|---|---|---|
| J-21 | 2-($OCH_2^iPr$) | 4-$CF_3$ | $C_3H_6$ | 5-$CF_3$-pyridin-2-yl | — |
| J-22 | 2-($OCH_2^cPr$) | 4-$CF_3$ | $C_3H_6$ | 5-$CF_3$-pyridin-2-yl | — |
| J-23 | 2-($CH_2OCH(OCH_3)CH_3$) | 4-$CF_3$ | $C_3H_6$ | 5-$CF_3$-pyridin-2-yl | — |
| J-24 | 2-($CO_2^iPr$) | 4-$CF_3$ | $C_3H_6$ | 5-$CF_3$-pyridin-2-yl | — |
| J-25 | 2-($OCH_2^iPr$) | 4-$CF_3$ | $C_3H_6$ | 6-$CF_3$-pyridazin-3-yl | — |
| J-26 | 2-($OCH_2^cPr$) | 4-$CF_3$ | $C_3H_6$ | 6-$CF_3$-pyridazin-3-yl | — |
| J-27 | 2-($CH_2OCH(OCH_3)CH_3$) | 4-$CF_3$ | $C_3H_6$ | 6-$CF_3$-pyridazin-3-yl | — |
| J-28 | 2-($CO_2^iPr$) | 4-$CF_3$ | $C_3H_6$ | 6-$CF_3$-pyridazin-3-yl | — |
| J-29 | 2-($OCH_2^iPr$) | 4-$CF_3$ | $C_3H_6$ | 5-$CF_3$-pyrimidin-2-yl | — |
| J-30 | 2-($OCH_2^cPr$) | 4-$CF_3$ | $C_3H_6$ | 5-$CF_3$-pyrimidin-2-yl | — |
| J-31 | 2-($CH_2OCH(OCH_3)CH_3$) | 4-$CF_3$ | $C_3H_6$ | 5-$CF_3$-pyrimidin-2-yl | — |
| J-32 | 2-($CO_2^iPr$) | 4-$CF_3$ | $C_3H_6$ | 5-$CF_3$-pyrimidin-2-yl | — |
| J-33 | 2-($OCH_2^iPr$) | 4-$CF_3$ | $C_3H_6$ | 5-$CF_3$-thiazol-2-yl | — |
| J-34 | 2-($OCH_2^cPr$) | 4-$CF_3$ | $C_3H_6$ | 5-$CF_3$-thiazol-2-yl | — |
| J-35 | 2-($CH_2OCH(OCH_3)CH_3$) | 4-$CF_3$ | $C_3H_6$ | 5-$CF_3$-thiazol-2-yl | — |
| J-36 | 2-($CO_2^iPr$) | 4-$CF_3$ | $C_3H_6$ | 5-$CF_3$-thiazol-2-yl | — |
| J-37 | 2-($OCH_2^iPr$) | 4-$CF_3$ | $C_3H_6$ | 5-$CF_3$-[1,3,4]thiadiazol-2-yl | — |
| J-38 | 2-($OCH_2^cPr$) | 4-$CF_3$ | $C_3H_6$ | 5-$CF_3$-[1,3,4]thiadiazol-2-yl | — |

TABLE 2-continued

| No. | $(R^{10})_m$ | $(R^{11})_n$ | A | $Cy^2$-$(R^{20})_p$ | $(R^{21})_r$ |
|---|---|---|---|---|---|
| J-39 | 2-($CH_2OCH(OCH_3)CH_3$) | 4-$CF_3$ | $C_3H_6$ | 5-$CF_3$-[1,3,4]thiadiazol-2-yl | — |
| J-40 | 2-($CO_2{}^iPr$) | 4-$CF_3$ | $C_3H_6$ | 5-$CF_3$-[1,3,4]thiadiazol-2-yl | — |
| J-41 | 2-($OCH_2{}^iPr$) | 4-$CF_3$ | $CH_2OCH_2$ | 5-$CF_3$-pyridin-2-yl | — |
| J-42 | 2-($OCH_2{}^cPr$) | 4-$CF_3$ | $CH_2OCH_2$ | 5-$CF_3$-pyridin-2-yl | — |
| J-43 | 2-($CH_2OCH(OCH_3)CH_3$) | 4-$CF_3$ | $CH_2OCH_2$ | 5-$CF_3$-pyridin-2-yl | — |
| J-44 | 2-($CO_2{}^iPr$) | 4-$CF_3$ | $CH_2OCH_2$ | 5-$CF_3$-pyridin-2-yl | — |
| J-45 | 2-($OCH_2{}^iPr$) | 4-$CF_3$ | $CH_2OCH_2$ | 6-$CF_3$-pyridazin-3-yl | — |
| J-46 | 2-($OCH_2{}^cPr$) | 4-$CF_3$ | $CH_2OCH_2$ | 6-$CF_3$-pyridazin-3-yl | — |
| J-47 | 2-($CH_2OCH(OCH_3)CH_3$) | 4-$CF_3$ | $CH_2OCH_2$ | 6-$CF_3$-pyridazin-3-yl | — |
| J-48 | 2-($CO_2{}^iPr$) | 4-$CF_3$ | $CH_2OCH_2$ | 6-$CF_3$-pyridazin-3-yl | — |
| J-49 | 2-($OCH_2{}^iPr$) | 4-$CF_3$ | $CH_2OCH_2$ | 5-$CF_3$-pyrimidin-2-yl | — |
| J-50 | 2-($OCH_2{}^iPr$) | 4-$CF_3$ | $CH_2OCH_2$ | 5-$CF_3$-pyrimidin-2-yl | — |
| J-51 | 2-($CH_2OCH(OCH_3)CH_3$) | 4-$CF_3$ | $CH_2OCH_2$ | 5-$CF_3$-pyrimidin-2-yl | — |
| J-52 | 2-($CO_2{}^iPr$) | 4-$CF_3$ | $CH_2OCH_2$ | 5-$CF_3$-pyrimidin-2-yl | — |
| J-53 | 2-($OCH_2{}^iPr$) | 4-$CF_3$ | $CH_2OCH_2$ | 5-$CF_3$-thiazol-2-yl | — |
| J-54 | 2-($OCH_2{}^cPr$) | 4-$CF_3$ | $CH_2OCH_2$ | 5-$CF_3$-thiazol-2-yl | — |
| J-55 | 2-($CH_2OCH(OCH_3)CH_3$) | 4-$CF_3$ | $CH_2OCH_2$ | 5-$CF_3$-thiazol-2-yl | — |
| J-56 | 2-($CO_2{}^iPr$) | 4-$CF_3$ | $CH_2OCH_2$ | 5-$CF_3$-thiazol-2-yl | — |
| J-57 | 2-($OCH_2{}^iPr$) | 4-$CF_3$ | $CH_2OCH_2$ | 5-$CF_3$-[1,3,4]thiadiazol-2-yl | — |
| J-58 | 2-($OCH_2{}^cPr$) | 4-$CF_3$ | $CH_2OCH_2$ | 5-$CF_3$-[1,3,4]thiadiazol-2-yl | — |
| J-59 | 2-($CH_2OCH(OCH_3)CH_3$) | 4-$CF_3$ | $CH_2OCH_2$ | 5-$CF_3$-[1,3,4]thiadiazol-2-yl | — |
| J-60 | 2-($CO_2{}^iPr$) | 4-$CF_3$ | $CH_2OCH_2$ | 5-$CF_3$-[1,3,4]thiadiazol-2-yl | — |
| J-61 | 2-($CO_2CH_3$) | 4-$CF_3$ | $C_3H_6$ | 5-$CF_3$-pyridin-2-yl | — |
| J-62 | 2-($OCH_2{}^iPr$) | 4-$CF_3$ | $C_3H_6$ | 5-CN-pyridin-2-yl | — |
| J-63 | 2-(OEt) | 4-$CF_3$ | $C_3H_6$ | 5-$CF_3$-pyridin-2-yl | — |
| J-64 | 2-($O^nPr$) | 4-$CF_3$ | $C_3H_6$ | 5-$CF_3$-pyridin-2-yl | — |
| J-65 | 2-($OCH_2OCH_3$) | 4-$CF_3$ | $C_3H_6$ | 5-$CF_3$-pyridin-2-yl | — |
| J-66 | 2-($OCH_2{}^iPr$) | 4-$CF_3$ | $C_3H_6$ | 6-CN-pyridazin-3-yl | — |
| J-67 | 2-OH | 4-$CF_3$ | $C_3H_6$ | 5-$CF_3$-pyridin-2-yl | — |
| J-68 | 2-($O^nBu$) | 4-$CF_3$ | $C_3H_6$ | 5-$CF_3$-pyridin-2-yl | — |
| J-69 | 2-([1,3]dioxolan-2-yl) | 4-$CF_3$ | $C_3H_6$ | 5-$CF_3$-pyridin-2-yl | — |
| J-70 | 2-($CH_2O^iPr$) | 4-$CF_3$ | $C_3H_6$ | 5-$CF_3$-pyridin-2-yl | — |
| J-71 | 2-($CH_2OCH_3$) | 4-$CF_3$ | $C_3H_6$ | 5-$CF_3$-pyridin-2-yl | — |
| J-72 | 2-($CH_2OEt$) | 4-$CF_3$ | $C_3H_6$ | 5-$CF_3$-pyridin-2-yl | — |
| J-73 | 2-($NHCH_2{}^iPr$) | 4-$CF_3$ | $C_3H_6$ | 5-$CF_3$-pyridin-2-yl | — |
| J-74 | 2-($O^iPr$) | 4-$CF_3$ | $C_3H_6$ | 5-$CF_3$-pyridin-2-yl | — |
| J-75 | 2-($O^sBu$) | 4-$CF_3$ | $C_3H_6$ | 5-$CF_3$-pyridin-2-yl | — |
| J-76 | 2-($OCO_2{}^iPr$) | 4-$CF_3$ | $C_3H_6$ | 5-$CF_3$-pyridin-2-yl | — |
| J-77 | 2-($OCH_2CF_3$) | 4-$CF_3$ | $C_3H_6$ | 5-$CF_3$-pyridin-2-yl | — |
| J-78 | 2-($OCH_2CH=CH_2$) | 4-$CF_3$ | $C_3H_6$ | 5-$CF_3$-pyridin-2-yl | — |
| J-79 | 2-($OCH_2CH=C(CH_3)_2$) | 4-$CF_3$ | $C_3H_6$ | 5-$CF_3$-pyridin-2-yl | — |
| J-80 | 2-($OCH_2{}^tBu$) | 4-$CF_3$ | $C_3H_6$ | 5-$CF_3$-pyridin-2-yl | — |
| J-81 | 2-($OCH_2CH=CCl_2$) | 4-$CF_3$ | $C_3H_6$ | 5-$CF_3$-pyridin-2-yl | — |
| J-82 | 2-($OCH_2C\equiv CH$) | 4-$CF_3$ | $C_3H_6$ | 5-$CF_3$-pyridin-2-yl | — |
| J-83 | 2-($OCH_2C(CH_3)=CH_2$) | 4-$CF_3$ | $C_3H_6$ | 5-$CF_3$-pyridin-2-yl | — |
| J-84 | 2-($OCH_2{}^sBu$) | 4-$CF_3$ | $C_3H_6$ | 5-$CF_3$-pyridin-2-yl | — |
| J-85 | 2-($OCH_2CN$) | 4-$CF_3$ | $C_3H_6$ | 5-$CF_3$-pyridin-2-yl | — |
| J-86 | 2-($OCH(CH_3)OCH_3$) | 4-$CF_3$ | $C_3H_6$ | 5-$CF_3$-pyridin-2-yl | — |
| J-87 | 2-($CO_2Et$) | 4-$CF_3$ | $C_3H_6$ | 5-$CF_3$-pyridin-2-yl | — |
| J-89 | 2-($OCH_2[2,2-Cl_2-3-Ph-{}^cPr]$) | 4-$CF_3$ | $C_3H_6$ | 5-$CF_3$-pyridin-2-yl | — |
| J-90 | 2-($OCH_2Ac$) | 4-$CF_3$ | $C_3H_6$ | 5-$CF_3$-pyridin-2-yl | — |
| J-91 | 2-($OCH_2CH(OH)CH_3$) | 4-$CF_3$ | $C_3H_6$ | 5-$CF_3$-pyridin-2-yl | — |
| J-92 | 2-($OCH_2CH(OCH_3)CH_3$) | 4-$CF_3$ | $C_3H_6$ | 5-$CF_3$-pyridin-2-yl | — |
| J-93 | 2-($O^cPen$) | 4-$CF_3$ | $C_3H_6$ | 5-$CF_3$-pyridin-2-yl | — |
| J-94 | 2-($OCONH^iPr$) | 4-$CF_3$ | $C_3H_6$ | 5-$CF_3$-pyridin-2-yl | — |
| J-95 | 2-($OSO_2CF_3$) | 4-$CF_3$ | $C_3H_6$ | 5-$CF_3$-pyridin-2-yl | — |
| J-96 | 2-Ph | 4-$CF_3$ | $C_3H_6$ | 5-$CF_3$-pyridin-2-yl | — |
| J-97 | 2-(pyridin-3-yl) | 4-$CF_3$ | $C_3H_6$ | 5-$CF_3$-pyridin-2-yl | — |
| J-98 | 2-($S^nPr$) | 4-$CF_3$ | $C_3H_6$ | 5-$CF_3$-pyridin-2-yl | — |
| J-99 | 2-($CH_2CH=CH_2$) | 4-$CF_3$ | $C_3H_6$ | 5-$CF_3$-pyridin-2-yl | — |
| J-100 | 2-($O^nPr$) | 4-Cl | $C_3H_6$ | 5-$CF_3$-pyridin-2-yl | — |
| J-101 | 2-($O^nPr$) | 4-$CF_3$ | $C_4H_8$ | 5-$CF_3$-pyridin-2-yl | — |
| J-102 | 2-($OCH_2{}^iPr$) | 4-Cl | $CH_2OCH_2$ | 5-$CF_3$-pyridin-2-yl | — |

[Chemical formula 35]

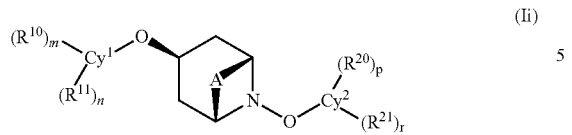

(Ii)

TABLE 3

| No. | Cy¹ | $(R^{10})_m$ | $(R^{11})_n$ | A | Cy² | $(R^{21})_r$ | $(R^{20})_p$ |
|---|---|---|---|---|---|---|---|
| K-5 | pyridin-2-yl | — | 5-CF₃ | C₃H₆ | Ph | 2-(OCH₂$^i$Pr) | 4-CF₃ |
| K-6 | pyridin-2-yl | — | 5-CF₃ | C₃H₆ | Ph | 2-(OCH₂$^c$Pr) | 4-CF₃ |
| K-7 | pyridin-2-yl | — | 5-CF₃ | C₃H₆ | Ph | 2-(CH₂OCH(OCH₃)CH₃) | 4-CF₃ |
| K-8 | pyridin-2-yl | — | 5-CF₃ | C₃H₆ | Ph | 2-(CO₂$^i$Pr) | 4-CF₃ |
| K-9 | pyridin-2-yl | — | 5-CF₃ | CH₂OCH₂ | Ph | 2-(OCH₂$^i$Pr) | 4-CF₃ |
| K-10 | pyridin-2-yl | — | 5-CF₃ | CH₂OCH₂ | Ph | 2-(OCH₂$^c$Pr) | 4-CF₃ |
| K-11 | pyridin-2-yl | — | 5-CF₃ | CH₂OCH₂ | Ph | 2-(CH₂OCH(OCH₃)CH₃) | 4-CF₃ |
| K-12 | pyridin-2-yl | — | 5-CF₃ | CH₂OCH₂ | Ph | 2-(CO₂$^i$Pr) | 4-CF₃ |
| K-18 | pyridazin-3-yl | — | 6-CF₃ | C₃H₆ | Ph | 2-(OCH₂$^i$Pr) | 4-CF₃ |
| K-19 | pyridazin-3-yl | — | 6-CF₃ | C₃H₆ | Ph | 2-(OCH₂$^c$Pr) | 4-CF₃ |
| K-20 | pyridazin-3-yl | — | 6-CF₃ | C₃H₆ | Ph | 2-(CH₂OCH(OCH₃)CH₃) | 4-CF₃ |
| K-21 | pyridazin-3-yl | — | 6-CF₃ | C₃H₆ | Ph | 2-(CO₂$^i$Pr) | 4-CF₃ |
| K-22 | pyridazin-3-yl | — | 6-CF₃ | CH₂OCH₂ | Ph | 2-(OCH₂$^i$Pr) | 4-CF₃ |
| K-23 | pyridazin-3-yl | — | 6-CF₃ | CH₂OCH₂ | Ph | 2-(OCH₂$^c$Pr) | 4-CF₃ |
| K-24 | pyridazin-3-yl | — | 6-CF₃ | CH₂OCH₂ | Ph | 2-(CH₂OCH(OCH₃)CH₃) | 4-CF₃ |
| K-25 | pyridazin-3-yl | — | 6-CF₃ | CH₂OCH₂ | Ph | 2-(CO₂$^i$Pr) | 4-CF₃ |
| K-30 | pyridin-2-yl | — | 5-CN | C₃H₆ | Ph | 2-(OCH₂$^i$Pr) | 4-CF₃ |
| K-31 | pyridin-2-yl | — | 5-CN | C₃H₆ | Ph | 2-(OCH₂$^c$Pr) | 4-CF₃ |
| K-32 | pyridin-2-yl | — | 5-CN | C₃H₆ | Ph | 2-(CH₂OCH(OCH₃)CH₃) | 4-CF₃ |
| K-33 | pyridin-2-yl | — | 5-CN | C₃H₆ | Ph | 2-(CO₂$^i$Pr) | 4-CF₃ |
| K-34 | pyridin-2-yl | — | 5-CN | CH₂OCH₂ | Ph | 2-(OCH₂$^i$Pr) | 4-CF₃ |
| K-35 | pyridin-2-yl | — | 5-CN | CH₂OCH₂ | Ph | 2-(OCH₂$^c$Pr) | 4-CF₃ |
| K-36 | pyridin-2-yl | — | 5-CN | CH₂OCH₂ | Ph | 2-(CH₂OCH(OCH₃)CH₃) | 4-CF₃ |
| K-37 | pyridin-2-yl | — | 5-CN | CH₂OCH₂ | Ph | 2-(CO₂$^i$Pr) | 4-CF₃ |
| K-38 | pyridin-3-yl | 2-(O$^n$Pr) | 6-CF₃ | C₃H₆ | pyridin-2-yl | — | 5-CF₃ |
| K-39 | pyrazol-5-yl | 1-$^n$Bu | 3-CF₃ | C₃H₆ | pyridin-2-yl | — | 5-CF₃ |
| K-40 | pyrazol-5-yl | 1-(CH₂$^i$Pr) | 3-CF₃ | C₃H₆ | pyridin-2-yl | — | 5-CF₃ |
| K-41 | pyrazol-5-yl | 1(CH₂$^c$Pr) | 3-CF₃ | C₃H₆ | pyridin-2-yl | — | 5-CF₃ |
| K-42 | pyrazol-5-yl | 1-(CH₂OCH₂OCH₃) | 3-CF₃ | C₃H₆ | pyridin-2-yl | — | 5-CF₃ |
| K-43 | pyrazol-5-yl | 1-(CH₂OCH(OCH₃)CH₃) | 3-CF₃ | C₃H₆ | pyridin-2-yl | — | 5-CF₃ |
| K-44 | pyrazol-5-yl | 1-(CH(OCH₃)CH₃) | 3-CF₃ | C₃H₆ | pyridin-2-yl | — | 5-CF₃ |
| K-45 | pyrazol-5-yl | 1-(CO₂$^i$Pr) | 3-CF₃ | C₃H₆ | pyridin-2-yl | — | 5-CF₃ |
| K-46 | pyrazol-5-yl | 1-(CH₂CH(OCH₃)₂) | 3-CF₃ | C₃H₆ | pyridin-2-yl | — | 5-CF₃ |
| K-47 | pyrazol-5-yl | 1-([1,3]dioxolan-2-yl) | 3-CF₃ | C₃H₆ | pyridin-2-yl | — | 5-CF₃ |
| K-48 | pyrazol-5-yl | 2-(CH₂$^i$Pr) | 3-CF₃ | C₃H₆ | pyridin-2-yl | — | 5-CF₃ |
| K-49 | pyrazol-5-yl | 2-(CH₂$^c$Pr) | 3-CF₃ | C₃H₆ | pyridin-2-yl | — | 5-CF₃ |
| K-50 | pyrazol-5-yl | 2-$^n$Bu | 3-CF₃ | C₃H₆ | pyridin-2-yl | — | 5-CF₃ |
| K-51 | pyrazol-5-yl | 2-(CH₂OCH₂OCH₃) | 3-CF₃ | C₃H₆ | pyridin-2-yl | — | 5-CF₃ |
| K-52 | pyrazol-5-yl | 2-(CH₂OCH(OCH₃)CH₃) | 3-CF₃ | C₃H₆ | pyridin-2-yl | — | 5-CF₃ |
| K-53 | pyrazol-5-yl | 2-(CH(OCH₃)CH₃) | 3-CF₃ | C₃H₆ | pyridin-2-yl | — | 5-CF₃ |
| K-54 | pyrazol-5-yl | 2-(CO₂$^i$Pr) | 3-CF₃ | C₃H₆ | pyridin-2-yl | — | 5-CF₃ |
| K-55 | pyrazol-5-yl | 2-(CH₂CH(OCH₃)₂) | 3-CF₃ | C₃H₆ | pyridin-2-yl | — | 5-CF₃ |
| K-56 | pyrazol-5-yl | 2-[1,3]dioxolan-2-yl) | 3-CF₃ | C₃H₆ | pyridin-2-yl | — | 5-CF₃ |
| K-57 | pyrazol-5-yl | 1,3-(CH₃)₂ | — | C₃H₆ | pyridin-2-yl | — | 5-CF₃ |
| K-58 | pyrazol-5-yl | 1-$^n$Bu-3-CH₃ | — | C₃H₆ | pyridin-2-yl | — | 5-CF₃ |
| K-59 | pyrazol-5-yl | 1-CH₃ | 3-CF₃ | C₃H₆ | pyridin-2-yl | — | 5-CF₃ |
| K-60 | pyrazol-5-yl | 1-Et | 3-CF₃ | C₃H₆ | pyridin-2-yl | — | 5-CF₃ |
| K-61 | pyrazol-5-yl | 1-$^n$Pr | 3-CF₃ | C₃H₆ | pyridin-2-yl | — | 5-CF₃ |
| K-62 | pyrazol-5-yl | 1-$^n$Pen | 3-CF₃ | C₃H₆ | pyridin-2-yl | — | 5-CF₃ |
| K-63 | pyrazol-5-yl | 1-$^n$Hex | 3-CF₃ | C₃H₆ | pyridin-2-yl | — | 5-CF₃ |
| K-64 | pyrazol-5-yl | 1-$^i$Pr | 3-CF₃ | C₃H₆ | pyridin-2-yl | — | 5-CF₃ |
| K-65 | pyrazol-5-yl | 1-$^t$Bu | 3-CF₃ | C₃H₆ | pyridin-2-yl | — | 5-CF₃ |
| K-66 | pyrazol-5-yl | 1-(CH₂CH=CH₂) | 3-CF₃ | C₃H₆ | pyridin-2-yl | — | 5-CF₃ |
| K-67 | pyrazol-5-yl | 1-(CH₂CN) | 3-CF₃ | C₃H₆ | pyridin-2-yl | — | 5-CF₃ |
| K-68 | pyrazol-5-yl | 1-((CH₂)₃CN) | 3-CF₃ | C₃H₆ | pyridin-2-yl | — | 5-CF₃ |
| K-69 | pyrazol-5-yl | 1-Bn | 3-CF₃ | C₃H₆ | pyridin-2-yl | — | 5-CF₃ |
| K-70 | pyrazol-5-yl | 1-(2-Cl-Bn) | 3-CF₃ | C₃H₆ | pyridin-2-yl | — | 5-CF₃ |
| K-71 | pyrazol-5-yl | 1-Ph | 3-CF₃ | C₃H₆ | pyridin-2-yl | — | 5-CF₃ |
| K-72 | pyrazol-5-yl | 1-(3-Cl—Ph) | 3-CF₃ | C₃H₆ | pyridin-2-yl | — | 5-CF₃ |
| K-73 | pyrazol-5-yl | 1-(3,5-Cl₂—Ph) | 3-CF₃ | C₃H₆ | pyridin-2-yl | — | 5-CF₃ |
| K-74 | pyrazol-5-yl | 1-(Py-2-yl) | 3-CF₃ | C₃H₆ | pyridin-2-yl | — | 5-CF₃ |
| K-75 | pyrazol-5-yl | 1-$^n$Bu | 3-CF₃ 4-Cl | C₃H₆ | pyridin-2-yl | — | 5-CF₃ |
| K-76 | pyrazol-5-yl | 1-$^n$Bu | 3-CF₃ 4-Br | C₃H₆ | pyridin-2-yl | — | 5-CF₃ |

TABLE 3-continued

| No. | Cy¹ | (R¹⁰)ₘ | (R¹¹)ₙ | A | Cy² | (R²¹)ᵣ | (R²⁰)ₚ |
|---|---|---|---|---|---|---|---|
| K-77 | pyrazol-5-yl | 1-$^n$Bu-4-Ph | 3-CF₃ | C₃H₆ | pyridin-2-yl | — | 5-CF₃ |
| K-78 | pyrazol-5-yl | 1-CH₃-4-(CHO) | 3-CF₃ | C₃H₆ | pyridin-2-yl | — | 5-CF₃ |
| K-79 | pyrazol-5-yl | 1-CH₃-4-(CH=NOCH₃) | 3-CF₃ | C₃H₆ | pyridin-2-yl | — | 5-CF₃ |
| K-80 | pyrazol-5-yl | 1-$^n$Bu-4-(CHO) | 3-CF₃ | C₃H₆ | pyridin-2-yl | — | 5-CF₃ |
| K-81 | pyrazol-5-yl | 1-$^n$Bu-3-Ph | — | C₃H₆ | pyridin-2-yl | — | 5-CF₃ |
| K-82 | pyrazol-5-yl | 1-$^n$Bu-3-(3-Cl—Ph) | — | C₃H₆ | pyridin-2-yl | — | 5-CF₃ |
| K-83 | pyrazol-5-yl | 1-$^n$Bu-3-(4-Cl—Ph) | — | C₃H₆ | pyridin-2-yl | — | 5-CF₃ |
| K-84 | pyrazol-5-yl | 1-$^n$Bu-3-(3,4-Cl₂—Ph) | — | C₃H₆ | pyridin-2-yl | — | 5-CF₃ |
| K-85 | pyrazol-5-yl | 1-$^n$Bu-3-(3,5-Cl₂—Ph) | — | C₃H₆ | pyridin-2-yl | — | 5-CF₃ |
| K-86 | pyrazol-5-yl | 1-$^n$Bu | 3-CF₃ | C₃H₆ | pyridin-2-yl | — | 5-CN |
| K-87 | pyrazol-5-yl | 1-$^n$Bu | 3-CF₃ | C₃H₆ | pyridin-2-yl | 5-NO₂ | — |
| K-88 | pyrazol-5-yl | 1-(3-CF₃—Ph) | 3-CF₃ | C₃H₆ | pyridin-2-yl | — | 5-CF₃ |
| K-89 | pyrazol-5-yl | 1-(3-CH₃—Ph) | 3-CF₃ | C₃H₆ | pyridin-2-yl | — | 5-CF₃ |
| K-90 | pyrazol-5-yl | 1-(Py-2-yl) 3-(3,4,5-F₃—Ph) | — | C₃H₆ | pyridin-2-yl | — | 5-CF₃ |
| K-91 | pyrazol-5-yl | 1-(Py-2-yl) 3-(3,5-F₂—Ph) | — | C₃H₆ | pyridin-2-yl | — | 5-CF₃ |
| K-92 | pyrazol-5-yl | 1-(3-Cl—Py-2-yl) | 3-CF₃ | C₃H₆ | pyridin-2-yl | — | 5-CF₃ |
| K-93 | pyrazol-5-yl | 1-(6-CH₃—Py-2-yl) | 3-CF₃ | C₃H₆ | pyridin-2-yl | — | 5-CF₃ |
| K-94 | pyrazol-5-yl | 1-(4-CF₃-thiazol-2-yl) | 3-CF₃ | C₃H₆ | pyridin-2-yl | — | 5-CF₃ |
| K-95 | pyrazol-5-yl | 1,4-(CH₃)₂ | 3-CF₃ | C₃H₆ | pyridin-2-yl | — | 5-CF₃ |
| K-96 | pyrazol-5-yl | 1-CH₃-4-(CH₂OH) | 3-CF₃ | C₃H₆ | pyridin-2-yl | — | 5-CF₃ |
| K-97 | pyrazol-5-yl | 1-$^n$Bu-4-CH₃ | 3-CF₃ | C₃H₆ | pyridin-2-yl | — | 5-CF₃ |
| K-98 | pyrazol-5-yl | 1-$_n$Bu 3-(3,5-(CF₃)₂—Ph) | — | C₃H₆ | pyridin-2-yl | — | 5-CF₃ |
| K-99 | pyrazol-5-yl | 1-$^n$Bu-3-(3,5-F₂—Ph) | — | C₃H₆ | pyridin-2-yl | — | 5-CF₃ |
| K-100 | pyrazol-5-yl | 1-$^n$Bu-3-(3,4,5-F₃—Ph) | — | C₃H₆ | pyridin-2-yl | — | 5-CF₃ |
| K-101 | pyrazol-5-yl | 1,4-(CH₃)₂-3-(CO₂Et) | — | C₃H₆ | pyridin-2-yl | — | 5-CF₃ |
| K-102 | pyrazol-5-yl | 1-CH₃ | 4-Cl 3-CF₃ | C₃H₆ | pyridin-2-yl | — | 5-CF₃ |
| K-103 | pyrazol-5-yl | — | 3-CF₃ | C₃H₆ | pyridin-2-yl | — | 5-CF₃ |
| K-104 | pyrazol-5-yl | 1-(C(=O)$^t$Bu) | 3-CF₃ | C₃H₆ | pyridin-2-yl | — | 5-CF₃ |
| K-105 | pyrazol-5-yl | 1-(Py-2-yl) 3-(3,5-Cl₂—Ph) | — | C₃H₆ | pyridin-2-yl | — | 5-CF₃ |
| K-106 | pyrazol-5-yl | 1-(CH₂OCH₃) | 3-CF₃ | C₃H₆ | pyridin-2-yl | — | 5-CF₃ |
| K-107 | pyrazol-5-yl | 1-(CH₂OEt) | 3-CF₃ | C₃H₆ | pyridin-2-yl | — | 5-CF₃ |
| K-108 | pyrazol-5-yl | 1-(CH₂CH₂OCH₃) | 3-CF₃ | C₃H₆ | pyridin-2-yl | — | 5-CF₃ |
| K-109 | pyrazol-5-yl | 1-(CH₂CH₂OEt) | 3-CF₃ | C₃H₆ | pyridin-2-yl | — | 5-CF₃ |
| K-110 | pyrazol-5-yl | 1-(CH₂CH(OEt)₂) | 3-CF₃ | C₃H₆ | pyridin-2-yl | — | 5-CF₃ |
| K-111 | pyrazol-5-yl | 1-(CH₂CH₂CH(OCH₃)₂) | 3-CF₃ | C₃H₆ | pyridin-2-yl | — | 5-CF₃ |
| K-112 | pyrazol-5-yl | 1-(CH₂CH₂CH(OEt)₂) | 3-CF₃ | C₃H₆ | pyridin-2-yl | — | 5-CF₃ |
| K-113 | pyrazol-5-yl | 1-(CH₂([1,3]dioxolan-2-yl)) | 3-CF₃ | C₃H₆ | pyridin-2-yl | — | 5-CF₃ |
| K-114 | pyrazol-5-yl | 1-(CH₂(tetrahydro-furan-2-yl)) | 3-CF₃ | C₃H₆ | pyridin-2-yl | — | 5-CF₃ |
| K-115 | pyrazol-5-yl | 1-(CH₂CH₂([1,3]dioxolan-2-yl)) | 3-CF₃ | C₃H₆ | pyridin-2-yl | — | 5-CF₃ |
| K-116 | pyrazol-5-yl | 1-(CH₂CH₂([1,3]dioxolan-2-yl)) | 3-CF₃ | C₃H₆ | pyridin-2-yl | — | 5-CF₃ |
| K-117 | pyrazol-5-yl | 1-Ac | 3-CF₃ | C₃H₆ | pyridin-2-yl | — | 5-CF₃ |
| K-118 | pyrazol-5-yl | 1-(C(=O)Et) | 3-CF₃ | C₃H₆ | pyridin-2-yl | — | 5-CF₃ |
| K-119 | pyrazol-5-yl | 1-(C(=O)$^n$Pr) | 3-CF₃ | C₃H₆ | pyridin-2-yl | — | 5-CF₃ |
| K-120 | pyrazol-5-yl | 1-(C(=O)$^n$Bu) | 3-CF₃ | C₃H₆ | pyridin-2-yl | — | 5-CF₃ |
| K-121 | pyrazol-5-yl | 1-(C(=O)Ph) | 3-CF₃ | C₃H₆ | pyridin-2-yl | — | 5-CF₃ |
| K-122 | pyrazol-5-yl | 1-(CO₂CH₃) | 3-CF₃ | C₃H₆ | pyridin-2-yl | — | 5-CF₃ |
| K-123 | pyrazol-5-yl | 1-(CO₂Et) | 3-CF₃ | C₃H₆ | pyridin-2-yl | — | 5-CF₃ |
| K-124 | pyrazol-5-yl | 1-(CO₂$^n$Pr) | 3-CF₃ | C₃H₆ | pyridin-2-yl | — | 5-CF₃ |
| K-125 | pyrazol-5-yl | 1-(CO₂$^n$Bu) | 3-CF₃ | C₃H₆ | pyridin-2-yl | — | 5-CF₃ |
| K-126 | pyrazol-5-yl | 1-(CH₂CHO) | 3-CF₃ | C₃H₆ | pyridin-2-yl | — | 5-CF₃ |
| K-127 | pyrazol-5-yl | 1-(CH₂CH₂CHO) | 3-CF₃ | C₃H₆ | pyridin-2-yl | — | 5-CF₃ |
| K-128 | pyrazol-5-yl | 1-CH₃-4-(CH=NOH) | 3-CF₃ | C₃H₆ | pyridin-2-yl | — | 5-CF₃ |
| K-129 | pyrazol-5-yl | 1-CH₃-4-(CH=NOEt) | 3-CF₃ | C₃H₆ | pyridin-2-yl | — | 5-CF₃ |
| K-130 | pyrazol-5-yl | 3-(3,5-F₂—Ph) | — | C₃H₆ | pyridin-2-yl | — | 5-CF₃ |
| K-131 | pyrazol-5-yl | 1-(CH₂CH(OCH₃)₂)-3-(3,5-F₂—Ph) | — | C₃H₆ | pyridin-2-yl | — | 5-CF₃ |
| K-132 | pyrazol-5-yl | 1-(CH₂([1,3]dioxolan-2-yl))-3-(3,5-F₂—Ph) | — | C₃H₆ | pyridin-2-yl | — | 5-CF₃ |
| K-133 | pyrazol-5-yl | 1-(Py-2-yl)-3-(thiophen-2-yl) | — | C₃H₆ | pyridin-2-yl | — | 5-CF₃ |
| K-134 | pyrazol-5-yl | 1-(CH₂CH₂CH=CH₂) | 3-CF₃ | C₃H₆ | pyridin-2-yl | — | 5-CF₃ |
| K-135 | pyrazol-5-yl | 1-(CH₂CH₂CH(Et)₂) | 3-CF₃ | C₃H₆ | pyridin-2-yl | — | 5-CF₃ |
| K-136 | pyrazol-5-yl | 1-$^i$Pen | 3-CF₃ | C₃H₆ | pyridin-2-yl | — | 5-CF₃ |

[Chemical formula 36]

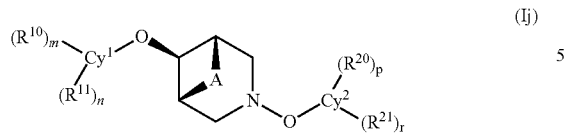

(Ij)

TABLE 4

| No. | Cy$^1$ | (R$^{10}$)$_m$ | (R$^{11}$)$_n$ | A | Cy$^2$ | (R$^{21}$)$_r$ | (R$^{20}$)$_p$ |
|---|---|---|---|---|---|---|---|
| L-5 | pyridin-2-yl | — | 5-CF$_3$ | C$_3$H$_6$ | Ph | 2-(OCH$_2$$^i$Pr) | 4-CF$_3$ |
| L-6 | pyridin-2-yl | — | 5-CF$_3$ | C$_3$H$_6$ | Ph | 2-(OCH$_2$$^c$Pr) | 4-CF$_3$ |
| L-7 | pyridin-2-yl | — | 5-CF$_3$ | C$_3$H$_6$ | Ph | 2-(CH$_2$OCH(OCH$_3$)CH$_3$) | 4-CF$_3$ |
| L-8 | pyridin-2-yl | — | 5-CF$_3$ | C$_3$H$_6$ | Ph | 2-(CO$_2$$^i$Pr) | 4-CF$_3$ |
| L-9 | pyridin-2-yl | — | 5-CF$_3$ | CH$_2$OCH$_2$ | Ph | 2-(OCH$_2$$^i$Pr) | 4-CF$_3$ |
| L-10 | pyridin-2-yl | — | 5-CF$_3$ | CH$_2$OCH$_2$ | Ph | 2-(OCH$_2$$^c$Pr) | 4-CF$_3$ |
| L-11 | pyridin-2-yl | — | 5-CF$_3$ | CH$_2$OCH$_2$ | Ph | 2-(CH$_2$OCH(OCH$_3$)CH$_3$) | 4-CF$_3$ |
| L-12 | pyridin-2-yl | — | 5-CF$_3$ | CH$_2$OCH$_2$ | Ph | 2-(CO$_2$$^i$Pr) | 4-CF$_3$ |
| L-18 | pyridazin-3-yl | — | 6-CF$_3$ | C$_3$H$_6$ | Ph | 2-(OCH$_2$$^i$Pr) | 4-CF$_3$ |
| L-19 | pyridazin-3-yl | — | 6-CF$_3$ | C$_3$H$_6$ | Ph | 2-(OCH$_2$$^c$Pr) | 4-CF$_3$ |
| L-20 | pyridazin-3-yl | — | 6-CF$_3$ | C$_3$H$_6$ | Ph | 2-(CH$_2$OCH(OCH$_3$)CH$_3$) | 4-CF$_3$ |
| L-21 | pyridazin-3-yl | — | 6-CF$_3$ | C$_3$H$_6$ | Ph | 2-(CO$_2$$^i$Pr) | 4-CF$_3$ |
| L-22 | pyridazin-3-yl | — | 6-CF$_3$ | CH$_2$OCH$_2$ | Ph | 2-(OCH$_2$$^i$Pr) | 4-CF$_3$ |
| L-23 | pyridazin-3-yl | — | 6-CF$_3$ | CH$_2$OCH$_2$ | Ph | 2-(OCH$_2$$^c$Pr) | 4-CF$_3$ |
| L-24 | pyridazin-3-yl | — | 6-CF$_3$ | CH$_2$OCH$_2$ | Ph | 2-(CH$_2$OCH(OCH$_3$)CH$_3$) | 4-CF$_3$ |
| L-25 | pyridazin-3-yl | — | 6-CF$_3$ | CH$_2$OCH$_2$ | Ph | 2-(CO$_2$$^i$Pr) | 4-CF$_3$ |
| L-26 | pyridin-2-yl | — | 5-CF$_3$ | C$_3$H$_6$ | Ph | 2-(CO$_2$CH$_3$) | 4-CF$_3$ |
| L-27 | pyridin-2-yl | — | 5-CN | C$_3$H$_6$ | Ph | 2-(OCH$_2$$^i$Pr) | 4-CF$_3$ |
| L-28 | pyridin-2-yl | — | 5-CF$_3$ | C$_3$H$_6$ | Ph | 2-(OEt) | 4-CF$_3$ |
| L-29 | pyridin-2-yl | — | 5-CF$_3$ | C$_3$H$_6$ | Ph | 2-(O$^n$Pr) | 4-CF$_3$ |
| L-30 | pyridin-2-yl | — | 5-CF$_3$ | C$_3$H$_6$ | Ph | 2-(OCH$_2$OCH$_3$) | 4-CF$_3$ |
| L-31 | pyridazin-3-yl | — | 6-CN | C$_3$H$_6$ | Ph | 2-(OCH$_2$$^i$Pr) | 4-CF$_3$ |
| L-32 | pyridin-2-yl | — | 5-CF$_3$ | C$_3$H$_6$ | Ph | 2-OH | 4-CF$_3$ |
| L-33 | pyridin-2-yl | — | 5-CF$_3$ | C$_3$H$_6$ | Ph | 2-(O$^n$Bu) | 4-CF$_3$ |
| L-34 | pyridin-2-yl | — | 5-CF$_3$ | C$_3$H$_6$ | Ph | 2-([1,3]dioxolan-2-yl) | 4-CF$_3$ |
| L-35 | pyridin-2-yl | — | 5-CF$_3$ | C$_3$H$_6$ | Ph | 2-(CH$_2$O$^i$Pr) | 4-CF$_3$ |
| L-36 | pyridin-2-yl | — | 5-CF$_3$ | C$_3$H$_6$ | Ph | 2-(CH$_2$OCH$_3$) | 4-CF$_3$ |
| L-37 | pyridin-2-yl | — | 5-CF$_3$ | C$_3$H$_6$ | Ph | 2-(CH$_2$OEt) | 4-CF$_3$ |
| L-38 | pyridin-2-yl | — | 5-CF$_3$ | C$_3$H$_6$ | Ph | 2-(NHCH$_2$$^i$Pr) | 4-CF$_3$ |
| L-39 | pyridin-2-yl | — | 5-CF$_3$ | C$_3$H$_6$ | Ph | 2-(O$^i$Pr) | 4-CF$_3$ |
| L-40 | pyridin-2-yl | — | 5-CF$_3$ | C$_3$H$_6$ | Ph | 2-(O$^s$Bu) | 4-CF$_3$ |
| L-41 | pyridin-2-yl | — | 5-CF$_3$ | C$_3$H$_6$ | Ph | 2-(OCO$_2$$^i$Pr) | 4-CF$_3$ |
| L-42 | pyridin-2-yl | — | 5-CF$_3$ | C$_3$H$_6$ | Ph | 2-(OCH$_2$CF$_3$) | 4-CF$_3$ |
| L-43 | pyridin-2-yl | — | 5-CF$_3$ | C$_3$H$_6$ | Ph | 2-(OCH$_2$CH=CH$_2$) | 4-CF$_3$ |
| L-44 | pyridin-2-yl | — | 5-CF$_3$ | C$_3$H$_6$ | Ph | 2-(OCH$_2$CH=C(CH$_3$)$_2$) | 4-CF$_3$ |
| L-45 | pyridin-2-yl | — | 5-CF$_3$ | C$_3$H$_6$ | Ph | 2-(OCH$_2$$^t$Bu) | 4-CF$_3$ |
| L-46 | pyridin-2-yl | — | 5-CF$_3$ | C$_3$H$_6$ | Ph | 2-(OCH$_2$CH=CCl$_2$) | 4-CF$_3$ |
| L-47 | pyridin-2-yl | — | 5-CF$_3$ | C$_3$H$_6$ | Ph | 2-(OCH$_2$C≡CH) | 4-CF$_3$ |
| L-48 | pyridin-2-yl | — | 5-CF$_3$ | C$_3$H$_6$ | Ph | 2-(OCH$_2$C(CH$_3$)=CH$_2$) | 4-CF$_3$ |
| L-49 | pyridin-2-yl | — | 5-CF$_3$ | C$_3$H$_6$ | Ph | 2-(OCH$_2$$^s$Bu) | 4-CF$_3$ |
| L-50 | pyridin-2-yl | — | 5-CF$_3$ | C$_3$H$_6$ | Ph | 2-(OCH$_2$CN) | 4-CF$_3$ |
| L-51 | pyridin-2-yl | — | 5-CF$_3$ | C$_3$H$_6$ | Ph | 2-(OCH(CH$_3$)OCH$_3$) | 4-CF$_3$ |
| L-52 | pyridin-2-yl | — | 5-CF$_3$ | C$_3$H$_6$ | Ph | 2-(CO$_2$Et) | 4-CF$_3$ |
| L-53 | pyridin-2-yl | — | 5-CF$_3$ | C$_3$H$_6$ | Ph | 2-(OAc) | 4-CF$_3$ |
| L-54 | pyridin-2-yl | — | 5-CF$_3$ | C$_3$H$_6$ | Ph | 2-(OCH$_2$[2,2-Cl$_2$-3-Ph—$^c$Pr]) | 4-CF$_3$ |
| L-55 | pyridin-2-yl | — | 5-CF$_3$ | C$_3$H$_6$ | Ph | 2-(OCH$_2$Ac) | 4-CF$_3$ |
| L-56 | pyridin-2-yl | — | 5-CF$_3$ | C$_3$H$_6$ | Ph | 2-(OCH$_2$CH(OH)CH$_3$) | 4-CF$_3$ |
| L-57 | pyridin-2-yl | — | 5-CF$_3$ | C$_3$H$_6$ | Ph | 2-(OCH$_2$CH(OCH$_3$)CH$_3$) | 4-CF$_3$ |
| L-58 | pyridin-2-yl | — | 5-CF$_3$ | C$_3$H$_6$ | Ph | 2-(O$^c$Pen) | 4-CF$_3$ |
| L-59 | pyridin-2-yl | — | 5-CF$_3$ | C$_3$H$_6$ | Ph | 2-(OCONH$^i$Pr) | 4-CF$_3$ |
| L-60 | pyridin-2-yl | — | 5-CF$_3$ | C$_3$H$_6$ | Ph | 2-(OSO$_2$CF$_3$) | 4-CF$_3$ |
| L-61 | pyridin-2-yl | — | 5-CF$_3$ | C$_3$H$_6$ | Ph | 2-Ph | 4-CF$_3$ |
| L-62 | pyridin-2-yl | — | 5-CF$_3$ | C$_3$H$_6$ | Ph | 2-(pyridin-3-yl) | 4-CF$_3$ |
| L-63 | pyridin-2-yl | — | 5-CF$_3$ | C$_3$H$_6$ | Ph | 2-(S$^n$Pr) | 4-CF$_3$ |
| L-64 | pyridin-2-yl | — | 5-CF$_3$ | C$_3$H$_6$ | Ph | 2-(CH$_2$CH=CH$_2$) | 4-CF$_3$ |
| L-65 | pyridin-2-yl | — | 5-CF$_3$ | C$_3$H$_6$ | Ph | 2-(O$^n$Pr) | 4-Cl |
| L-66 | pyridin-2-yl | — | 5-CF$_3$ | C$_4$H$_8$ | Ph | 2-(O$^n$Pr) | 4-CF$_3$ |
| L-67 | pyridin-2-yl | — | 5-CF$_3$ | CH$_2$OCH$_2$ | Ph | 2-(OCH$_2$$^i$Pr) | 4-Cl |

[Chemical formula 37]

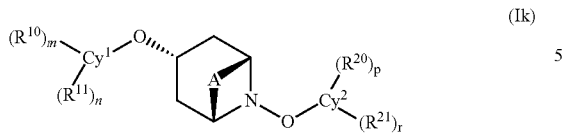

(Ik)

TABLE 5

| No. | Cy¹ | $(R^{10})_m$ | $(R^{11})_n$ | A | Cy² | $(R^{21})_r$ | $(R^{20})_p$ |
|---|---|---|---|---|---|---|---|
| M-5 | Ph | 2-(OCH$_2^i$Pr) | 4-CF$_3$ | C$_3$H$_6$ | pyridin-2-yl | — | 5-CF$_3$ |
| M-6 | Ph | 2-(OCH$_2^c$Pr) | 4-CF$_3$ | C$_3$H$_6$ | pyridin-2-yl | — | 5-CF$_3$ |
| M-7 | Ph | 2-(CH$_2$OCH(OCH$_3$)CH$_3$) | 4-CF$_3$ | C$_3$H$_6$ | pyridin-2-yl | — | 5-CF$_3$ |
| M-8 | Ph | 2-(CO$_2^i$Pr) | 4-CF$_3$ | C$_3$H$_6$ | pyridin-2-yl | — | 5-CF$_3$ |
| M-9 | Ph | 2-(OCH$_2^i$Pr) | 4-CF$_3$ | CH$_2$OCH$_2$ | pyridin-2-yl | — | 5-CF$_3$ |
| M-10 | Ph | 2-(OCH$_2^c$Pr) | 4-CF$_3$ | CH$_2$OCH$_2$ | pyridin-2-yl | — | 5-CF$_3$ |
| M-11 | Ph | 2-(CH$_2$OCH(OCH$_3$)CH$_3$) | 4-CF$_3$ | CH$_2$OCH$_2$ | pyridin-2-yl | — | 5-CF$_3$ |
| M-12 | Ph | 2-(CO$_2^i$Pr) | 4-CF$_3$ | CH$_2$OCH$_2$ | pyridin-2-yl | — | 5-CF$_3$ |
| M-17 | Ph | 2-(OCH$_2^i$Pr) | 4-CF$_3$ | C$_3$H$_6$ | pyridazin-3-yl | — | 6-CF$_3$ |
| M-18 | Ph | 2-(OCH$_2^c$Pr) | 4-CF$_3$ | C$_3$H$_6$ | pyridazin-3-yl | — | 6-CF$_3$ |
| M-19 | Ph | 2-(CH$_2$OCH(OCH$_3$)CH$_3$) | 4-CF$_3$ | C$_3$H$_6$ | pyridazin-3-yl | — | 6-CF$_3$ |
| M-20 | Ph | 2-(CO$_2^i$Pr) | 4-CF$_3$ | C$_3$H$_6$ | pyridazin-3-yl | — | 6-CF$_3$ |
| M-21 | Ph | 2-(OCH$_2^i$Pr) | 4-CF$_3$ | CH$_2$OCH$_2$ | pyridazin-3-yl | — | 6-CF$_3$ |
| M-22 | Ph | 2-(OCH$_2^c$Pr) | 4-CF$_3$ | CH$_2$OCH$_2$ | pyridazin-3-yl | — | 6-CF$_3$ |
| M-23 | Ph | 2-(CH$_2$OCH(OCH$_3$)CH$_3$) | 4-CF$_3$ | CH$_2$OCH$_2$ | pyridazin-3-yl | — | 6-CF$_3$ |
| M-24 | Ph | 2-(CO$_2^i$Pr) | 4-CF$_3$ | CH$_2$OCH$_2$ | pyridazin-3-yl | — | 6-CF$_3$ |
| M-25 | Ph | 2-(CO$_2$CH$_3$) | 4-CF$_3$ | C$_3$H$_6$ | pyridin-2-yl | — | 5-CF$_3$ |
| M-26 | Ph | 2-(OCH$_2^i$Pr) | 4-CF$_3$ | C$_3$H$_6$ | pyridin-2-yl | — | 5-CN |
| M-27 | Ph | 2-(OEt) | 4-CF$_3$ | C$_3$H$_6$ | pyridin-2-yl | — | 5-CF$_3$ |
| M-28 | Ph | 2-(O$^n$Pr) | 4-CF$_3$ | C$_3$H$_6$ | pyridin-2-yl | — | 5-CF$_3$ |
| M-29 | Ph | 2-(OCH$_2$OCH$_3$) | 4-CF$_3$ | C$_3$H$_6$ | pyridin-2-yl | — | 5-CF$_3$ |
| M-30 | Ph | 2-(OCH$_2^i$Pr) | 4-CF$_3$ | C$_3$H$_6$ | pyridazin-3-yl | — | 6-CN |
| M-31 | Ph | 2-OH | 4-CF$_3$ | C$_3$H$_6$ | pyridin-2-yl | — | 5-CF$_3$ |
| M-32 | Ph | 2-(O$^n$Bu) | 4-CF$_3$ | C$_3$H$_6$ | pyridin-2-yl | — | 5-CF$_3$ |
| M-33 | Ph | 2-([1,3]dioxolan-2-yl) | 4-CF$_3$ | C$_3$H$_6$ | pyridin-2-yl | — | 5-CF$_3$ |
| M-34 | Ph | 2-(CH$_2$O$^i$Pr) | 4-CF$_3$ | C$_3$H$_6$ | pyridin-2-yl | — | 5-CF$_3$ |
| M-35 | Ph | 2-(CH$_2$OCH$_3$) | 4-CF$_3$ | C$_3$H$_6$ | pyridin-2-yl | — | 5-CF$_3$ |
| M-36 | Ph | 2-(CH$_2$OEt) | 4-CF$_3$ | C$_3$H$_6$ | pyridin-2-yl | — | 5-CF$_3$ |
| M-37 | Ph | 2-(NHCH$_2^i$Pr) | 4-CF$_3$ | C$_3$H$_6$ | pyridin-2-yl | — | 5-CF$_3$ |
| M-38 | Ph | 2-(O$^i$Pr) | 4-CF$_3$ | C$_3$H$_6$ | pyridin-2-yl | — | 5-CF$_3$ |
| M-39 | Ph | 2-(O$^s$Bu) | 4-CF$_3$ | C$_3$H$_6$ | pyridin-2-yl | — | 5-CF$_3$ |
| M-40 | Ph | 2-(OCO$_2^i$Pr) | 4-CF$_3$ | C$_3$H$_6$ | pyridin-2-yl | — | 5-CF$_3$ |
| M-41 | Ph | 2-(OCH$_2$CF$_3$) | 4-CF$_3$ | C$_3$H$_6$ | pyridin-2-yl | — | 5-CF$_3$ |
| M-42 | Ph | 2-(OCH$_2$CH=CH$_2$) | 4-CF$_3$ | C$_3$H$_6$ | pyridin-2-yl | — | 5-CF$_3$ |
| M-43 | Ph | 2-(OCH$_2$CH=C(CH$_3$)$_2$) | 4-CF$_3$ | C$_3$H$_6$ | pyridin-2-yl | — | 5-CF$_3$ |
| M-44 | Ph | 2-(OCH$_2^t$Bu) | 4-CF$_3$ | C$_3$H$_6$ | pyridin-2-yl | — | 5-CF$_3$ |
| M-45 | Ph | 2-(OCH$_2$CH=CCl$_2$) | 4-CF$_3$ | C$_3$H$_6$ | pyridin-2-yl | — | 5-CF$_3$ |
| M-46 | Ph | 2-(OCH$_2$C≡CH) | 4-CF$_3$ | C$_3$H$_6$ | pyridin-2-yl | — | 5-CF$_3$ |
| M-47 | Ph | 2-(OCH$_2$C(CH$_3$)=CH$_2$) | 4-CF$_3$ | C$_3$H$_6$ | pyridin-2-yl | — | 5-CF$_3$ |
| M-48 | Ph | 2-(OCH$_2^s$Bu) | 4-CF$_3$ | C$_3$H$_6$ | pyridin-2-yl | — | 5-CF$_3$ |
| M-49 | Ph | 2-(OCH$_2$CN) | 4-CF$_3$ | C$_3$H$_6$ | pyridin-2-yl | — | 5-CF$_3$ |
| M-50 | Ph | 2-(OCH(CH$_3$)OCH$_3$) | 4-CF$_3$ | C$_3$H$_6$ | pyridin-2-yl | — | 5-CF$_3$ |
| M-51 | Ph | 2-(CO$_2$Et) | 4-CF$_3$ | C$_3$H$_6$ | pyridin-2-yl | — | 5-CF$_3$ |
| M-52 | Ph | 2-(OAc) | 4-CF$_3$ | C$_3$H$_6$ | pyridin-2-yl | — | 5-CF$_3$ |
| M-53 | Ph | 2-(OCH$_2$[2,2-Cl$_2$-3-Ph—$^c$Pr]) | 4-CF$_3$ | C$_3$H$_6$ | pyridin-2-yl | — | 5-CF$_3$ |
| M-54 | Ph | 2-(OCH$_2$Ac) | 4-CF$_3$ | C$_3$H$_6$ | pyridin-2-yl | — | 5-CF$_3$ |
| M-55 | Ph | 2-(OCH$_2$CH(OH)CH$_3$) | 4-CF$_3$ | C$_3$H$_6$ | pyridin-2-yl | — | 5-CF$_3$ |
| M-56 | Ph | 2-(OCH$_2$CH(OCH$_3$)CH$_3$) | 4-CF$_3$ | C$_3$H$_6$ | pyridin-2-yl | — | 5-CF$_3$ |
| M-57 | Ph | 2-(O$^c$Pen) | 4-CF$_3$ | C$_3$H$_6$ | pyridin-2-yl | — | 5-CF$_3$ |
| M-58 | Ph | 2-(OCONH$^i$Pr) | 4-CF$_3$ | C$_3$H$_6$ | pyridin-2-yl | — | 5-CF$_3$ |
| M-59 | Ph | 2-(OSO$_2$CF$_3$) | 4-CF$_3$ | C$_3$H$_6$ | pyridin-2-yl | — | 5-CF$_3$ |
| M-60 | Ph | 2-Ph | 4-CF$_3$ | C$_3$H$_6$ | pyridin-2-yl | — | 5-CF$_3$ |
| M-61 | Ph | 2-(pyridin-3-yl) | 4-CF$_3$ | C$_3$H$_6$ | pyridin-2-yl | — | 5-CF$_3$ |
| M-62 | Ph | 2-(S$^n$Pr) | 4-CF$_3$ | C$_3$H$_6$ | pyridin-2-yl | — | 5-CF$_3$ |
| M-63 | Ph | 2-(CH$_2$CH=CH$_2$) | 4-CF$_3$ | C$_3$H$_6$ | pyridin-2-yl | — | 5-CF$_3$ |
| M-64 | Ph | 2-(O$^n$Pr) | 4-Cl | C$_3$H$_6$ | pyridin-2-yl | — | 5-CF$_3$ |
| M-65 | Ph | 2-(O$^n$Pr) | 4-CF$_3$ | C$_4$H$_8$ | pyridin-2-yl | — | 5-CF$_3$ |
| M-66 | Ph | 2-(OCH$_2^i$Pr) | 4-Cl | CH$_2$OCH$_2$ | pyridin-2-yl | — | 5-CF$_3$ |
| M-67 | pyridin-2-yl | — | 5-CF$_3$ | C$_3$H$_6$ | Ph | 2-(OCH$_2^i$Pr) | 4-CF$_3$ |
| M-68 | pyridin-2-yl | — | 5-CF$_3$ | C$_3$H$_6$ | Ph | 2-(OCH$_2^c$Pr) | 4-CF$_3$ |
| M-69 | pyridin-2-yl | — | 5-CF$_3$ | C$_3$H$_6$ | Ph | 2-(CH$_2$OCH(OCH$_3$)CH$_3$) | 4-CF$_3$ |
| M-70 | pyridin-2-yl | — | 5-CF$_3$ | C$_3$H$_6$ | Ph | 2-(CO$_2^i$Pr) | 4-CF$_3$ |
| M-71 | pyridin-2-yl | — | 5-CF$_3$ | CH$_2$OCH$_2$ | Ph | 2-(OCH$_2^i$Pr) | 4-CF$_3$ |
| M-72 | pyridin-2-yl | — | 5-CF$_3$ | CH$_2$OCH$_2$ | Ph | 2-(OCH$_2^c$Pr) | 4-CF$_3$ |

TABLE 5-continued

| No. | Cy$^1$ | (R$^{10}$)$_m$ | (R$^{11}$)$_n$ | A | Cy$^2$ | (R$^{21}$)$_r$ | (R$^{20}$)$_p$ |
|---|---|---|---|---|---|---|---|
| M-73 | pyridin-2-yl | — | 5-CF$_3$ | CH$_2$OCH$_2$ | Ph | 2-(CH$_2$OCH(OCH$_3$)CH$_3$) | 4-CF$_3$ |
| M-74 | pyridin-2-yl | — | 5-CF$_3$ | CH$_2$OCH$_2$ | Ph | 2-(CO$_2$$^i$Pr) | 4-CF$_3$ |
| M-75 | Pyridazin-3-yl | — | 6-CF$_3$ | C$_3$H$_6$ | Ph | 2-(OCH$_2$$^i$Pr) | 4-CF$_3$ |
| M-76 | Pyridazin-3-yl | — | 6-CF$_3$ | C$_3$H$_6$ | Ph | 2-(OCH$_2$$^c$Pr) | 4-CF$_3$ |
| M-77 | Pyridazin-3-yl | — | 6-CF$_3$ | C$_3$H$_6$ | Ph | 2-(CH$_2$OCH(OCH$_3$)CH$_3$) | 4-CF$_3$ |
| M-78 | Pyridazin-3-yl | — | 6-CF$_3$ | C$_3$H$_6$ | Ph | 2-(CO$_2$$^i$Pr) | 4-CF$_3$ |
| M-79 | Pyridazin-3-yl | — | 6-CF$_3$ | CH$_2$OCH$_2$ | Ph | 2-(OCH$_2$$^i$Pr) | 4-CF$_3$ |
| M-80 | Pyridazin-3-yl | — | 6-CF$_3$ | CH$_2$OCH$_2$ | Ph | 2-(OCH$_2$$^c$Pr) | 4-CF$_3$ |
| M-81 | Pyridazin-3-yl | — | 6-CF$_3$ | CH$_2$OCH$_2$ | Ph | 2-(CH$_2$OCH(OCH$_3$)CH$_3$) | 4-CF$_3$ |
| M-82 | Pyridazin-3-yl | — | 6-CF$_3$ | CH$_2$OCH$_2$ | Ph | 2-(CO$_2$$^i$Pr) | 4-CF$_3$ |
| M-83 | Pyrazol-5-yl | 1-$^n$Bu | 3-CF$_3$ | C$_3$H$_6$ | pyridin-2-yl | — | 5-CF$_3$ |
| M-84 | pyrazol-5-yl | 1-(CH$_2$CH(OCH$_3$)$_2$) | 3-CF$_3$ | C$_3$H$_6$ | pyridin-2-yl | — | 5-CF$_3$ |
| M-85 | pyrazol-5-yl | 1-$^n$Pen | 3-CF$_3$ | C$_3$H$_6$ | pyridin-2-yl | — | 5-CF$_3$ |
| M-86 | pyrazol-5-yl | 1-$^n$Hex | 3-CF$_3$ | C$_3$H$_6$ | pyridin-2-yl | — | 5-CF$_3$ |
| M-87 | pyrazol-5-yl | 1-$^i$Pr | 3-CF$_3$ | C$_3$H$_6$ | pyridin-2-yl | — | 5-CF$_3$ |
| M-88 | pyrazol-5-yl | 1-(CH$_2$CH=CH$_2$) | 3-CF$_3$ | C$_3$H$_6$ | pyridin-2-yl | — | 5-CF$_3$ |
| M-89 | pyrazol-5-yl | 1-(CH$_2$CN) | 3-CF$_3$ | C$_3$H$_6$ | pyridin-2-yl | — | 5-CF$_3$ |
| M-90 | pyrazol-5-yl | 1-Bn | 3-CF$_3$ | C$_3$H$_6$ | pyridin-2-yl | — | 5-CF$_3$ |
| M-91 | pyrazol-5-yl | 1-(Py$^2$-yl) | 3-CF$_3$ | C$_3$H$_6$ | pyridin-2-yl | — | 5-CF$_3$ |
| M-92 | pyrazol-5-yl | 1-$_n$Bu-3-(3,5-(CF$_3$)$_2$—Ph) | — | C$_3$H$_6$ | pyridin-2-yl | — | 5-CF$_3$ |
| M-93 | pyrazol-5-yl | 1-$^n$Bu-3-(3,5-F$_2$—Ph) | — | C$_3$H$_6$ | pyridin-2-yl | — | 5-CF$_3$ |
| M-94 | pyrazol-5-yl | 1-$^n$Bu-3-(3,4,5-F$_3$—Ph) | — | C$_3$H$_6$ | pyridin-2-yl | — | 5-CF$_3$ |
| M-95 | pyrazol-5-yl | 1-(CH$_2$OCH$_3$) | 3-CF$_3$ | C$_3$H$_6$ | pyridin-2-yl | — | 5-CF$_3$ |
| M-96 | pyrazol-5-yl | 1-(CH$_2$OEt) | 3-CF$_3$ | C$_3$H$_6$ | pyridin-2-yl | — | 5-CF$_3$ |
| M-97 | pyrazol-5-yl | 1-(CH$_2$CH$_2$OCH$_3$) | 3-CF$_3$ | C$_3$H$_6$ | pyridin-2-yl | — | 5-CF$_3$ |
| M-98 | pyrazol-5-yl | 1-(CH$_2$CH$_2$OEt) | 3-CF$_3$ | C$_3$H$_6$ | pyridin-2-yl | — | 5-CF$_3$ |
| M-99 | pyrazol-5-yl | 1-(CH$_2$CH(OEt)$_2$) | 3-CF$_3$ | C$_3$H$_6$ | pyridin-2-yl | — | 5-CF$_3$ |
| M-100 | pyrazol-5-yl | 1-(CH$_2$CH$_2$CH(OCH$_3$)$_2$) | 3-CF$_3$ | C$_3$H$_6$ | pyridin-2-yl | — | 5-CF$_3$ |
| M-101 | pyrazol-5-yl | 1-(CH$_2$CH$_2$CH(OEt)$_2$) | 3-CF$_3$ | C$_3$H$_6$ | pyridin-2-yl | — | 5-CF$_3$ |
| M-102 | pyrazol-5-yl | 1-(CH$_2$([1,3]dioxolan-2-yl)) | 3-CF$_3$ | C$_3$H$_6$ | pyridin-2-yl | — | 5-CF$_3$ |
| M-103 | pyrazol-5-yl | 1-(CH$_2$CH(OCH$_3$)$_2$)-3-(3,5-F$_2$—Ph) | — | C$_3$H$_6$ | pyridin-2-yl | — | 5-CF$_3$ |

[Chemical formula 38]

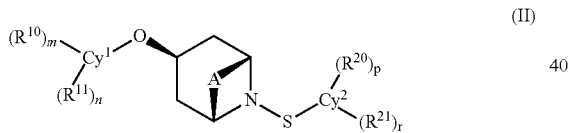

(II)

TABLE 6

| No. | Cy$^1$ | (R$^{10}$)$_m$ | (R$^{11}$)$_n$ | A | Cy$^2$ | (R$^{21}$)$_r$ | (R$^{20}$)$_p$ |
|---|---|---|---|---|---|---|---|
| N-1 | Ph | 2-(OCH$_2$$^i$Pr) | 4-CF$_3$ | C$_3$H$_6$ | pyridin-2-yl | — | 5-CF$_3$ |
| N-2 | Ph | 2-(OCH$_2$$^c$Pr) | 4-CF$_3$ | C$_3$H$_6$ | pyridin-2-yl | — | 5-CF$_3$ |
| N-3 | Ph | 2-(CH$_2$OCH(OCH$_3$)CH$_3$) | 4-CF$_3$ | C$_3$H$_6$ | pyridin-2-yl | — | 5-CF$_3$ |
| N-4 | Ph | 2-(CO$_2$$^i$Pr) | 4-CF$_3$ | C$_3$H$_6$ | pyridin-2-yl | — | 5-CF$_3$ |
| N-5 | Ph | 2-(OCH$_2$$^i$Pr) | 4-CF$_3$ | CH$_2$OCH$_2$ | pyridin-2-yl | — | 5-CF$_3$ |
| H-6 | Ph | 2-(OCH$_2$$^c$Pr) | 4-CF$_3$ | CH$_2$OCH$_2$ | pyridin-2-yl | — | 5-CF$_3$ |
| N-7 | Ph | 2-(CH$_2$OCH(OCH$_3$)CH$_3$) | 4-CF$_3$ | CH$_2$OCH$_2$ | pyridin-2-yl | — | 5-CF$_3$ |
| N-8 | Ph | 2-(CO$_2$$^i$Pr) | 4-CF$_3$ | CH$_2$OCH$_2$ | pyridin-2-yl | — | 5-CF$_3$ |
| N-9 | Ph | 2-(OCH$_2$$^i$Pr) | 4-CF$_3$ | C$_3$H$_6$ | pyridazin-3-yl | — | 6-CF$_3$ |
| N-10 | Ph | 2-(OCH$_2$$^c$Pr) | 4-CF$_3$ | C$_3$H$_6$ | pyridazin-3-yl | — | 6-CF$_3$ |
| N-11 | Ph | 2-(CH$_2$OCH(OCH$_3$)CH$_3$) | 4-CF$_3$ | C$_3$H$_6$ | pyridazin-3-yl | — | 6-CF$_3$ |
| N-12 | Ph | 2-(CO$_2$$^i$Pr) | 4-CF$_3$ | C$_3$H$_6$ | pyridazin-3-yl | — | 6-CF$_3$ |
| N-13 | Ph | 2-(OCH$_2$$^i$Pr) | 4-CF$_3$ | CH$_2$OCH$_2$ | pyridazin-3-yl | — | 6-CF$_3$ |
| N-14 | Ph | 2-(OCH$_2$$^c$Pr) | 4-CF$_3$ | CH$_2$OCH$_2$ | pyridazin-3-yl | — | 6-CF$_3$ |
| N-15 | Ph | 2-(CH$_2$OCH(OCH$_3$)CH$_3$) | 4-CF$_3$ | CH$_2$OCH$_2$ | pyridazin-3-yl | — | 6-CF$_3$ |
| N-16 | Ph | 2-(CO$_2$$^i$Pr) | 4-CF$_3$ | CH$_2$OCH$_2$ | pyridazin-3-yl | — | 6-CF$_3$ |
| N-17 | pyridin-2-yl | — | 5-CF$_3$ | C$_3$H$_6$ | Ph | 2-(OCH$_2$$^i$Pr) | 4-CF$_3$ |
| N-18 | pyridin-2-yl | — | 5-CF$_3$ | C$_3$H$_6$ | Ph | 2-(OCH$_2$$^c$Pr) | 4-CF$_3$ |
| N-19 | pyridin-2-yl | — | 5-CF$_3$ | C$_3$H$_6$ | Ph | 2-(CH$_2$OCH(OCH$_3$)CH$_3$) | 4-CF$_3$ |
| N-20 | pyridin-2-yl | — | 5-CF$_3$ | C$_3$H$_6$ | Ph | 2-(CO$_2$$^i$Pr) | 4-CF$_3$ |
| N-21 | pyridin-2-yl | — | 5-CF$_3$ | CH$_2$OCH$_2$ | Ph | 2-(OCH$_2$$^i$Pr) | 4-CF$_3$ |
| N-22 | pyridin-2-yl | — | 5-CF$_3$ | CH$_2$OCH$_2$ | Ph | 2-(OCH$_2$$^c$Pr) | 4-CF$_3$ |

TABLE 6-continued

| No. | Cy$^1$ | (R$^{10}$)$_m$ | (R$^{11}$)$_n$ | A | Cy$^2$ | (R$^{21}$)$_r$ | (R$^{20}$)$_p$ |
|---|---|---|---|---|---|---|---|
| N-23 | pyridin-2-yl | — | 5-CF$_3$ | CH$_2$OCH$_2$ | Ph | 2-(CH$_2$OCH(OCH$_3$)CH$_3$) | 4-CF$_3$ |
| N-24 | pyridin-2-yl | — | 5-CF$_3$ | CH$_2$OCH$_2$ | Ph | 2-(CO$_2^i$Pr) | 4-CF$_3$ |
| N-25 | pyridazin-3-yl | — | 6-CF$_3$ | C$_3$H$_6$ | Ph | 2-(OCH$_2^i$Pr) | 4-CF$_3$ |
| N-26 | pyridazin-3-yl | — | 6-CF$_3$ | C$_3$H$_6$ | Ph | 2-(OCH$_2^c$Pr) | 4-CF$_3$ |
| N-27 | pyridazin-3-yl | — | 6-CF$_3$ | C$_3$H$_6$ | Ph | 2-(CH$_2$OCH(OCH$_3$)CH$_3$) | 4-CF$_3$ |
| N-28 | pyridazin-3-yl | — | 6-CF$_3$ | C$_3$H$_6$ | Ph | 2-(CO$_2^i$Pr) | 4-CF$_3$ |
| N-29 | pyridazin-3-yl | — | 6-CF$_3$ | CH$_2$OCH$_2$ | Ph | 2-(OCH$_2^i$Pr) | 4-CF$_3$ |
| N-30 | pyridazin-3-yl | — | 6-CF$_3$ | CH$_2$OCH$_2$ | Ph | 2-(OCH$_2^c$Pr) | 4-CF$_3$ |
| N-31 | pyridazin-3-yl | — | 6-CF$_3$ | CH$_2$OCH$_2$ | Ph | 2-(CH$_2$OCH(OCH$_3$)CH$_3$) | 4-CF$_3$ |
| N-32 | pyridazin-3-yl | — | 6-CF$_3$ | CH$_2$OCH$_2$ | Ph | 2-(CO$_2^i$Pr) | 4-CF$_3$ |
| N-33 | pyrazol-5-yl | 1-$^n$Bu | 3-CF$_3$ | C$_3$H$_6$ | pyridin-2-yl | — | 5-CF$_3$ |
| N-34 | pyrazol-5-yl | 1-(CH$_2$CH(OCH$_3$)$_2$) | 3-CF$_3$ | C$_3$H$_6$ | pyridin-2-yl | — | 5-CF$_3$ |
| N-35 | pyrazol-5-yl | 1-$^n$Pen | 3-CF$_3$ | C$_3$H$_6$ | pyridin-2-yl | — | 5-CF$_3$ |
| N-36 | pyrazol-5-yl | 1-$^n$Hex | 3-CF$_3$ | C$_3$H$_6$ | pyridin-2-yl | — | 5-CF$_3$ |
| N-37 | pyrazol-5-yl | 1-$^i$Pr | 3-CF$_3$ | C$_3$H$_6$ | pyridin-2-yl | — | 5-CF$_3$ |
| N-38 | pyrazol-5-yl | 1-(CH$_2$CH=CH$_2$) | 3-CF$_3$ | C$_3$H$_6$ | pyridin-2-yl | — | 5-CF$_3$ |
| N-39 | pyrazol-5-yl | 1-(CH$_2$CN) | 3-CF$_3$ | C$_3$H$_6$ | pyridin-2-yl | — | 5-CF$_3$ |
| N-40 | pyrazol-5-yl | 1-Bn | 3-CF$_3$ | C$_3$H$_6$ | pyridin-2-yl | — | 5-CF$_3$ |
| N-41 | pyrazol-5-yl | 1-(Py-2-yl) | 3-CF$_3$ | C$_3$H$_6$ | pyridin-2-yl | — | 5-CF$_3$ |
| N-42 | pyrazol-5-yl | 1-$_n$Bu 3-(3,5-(CF$_3$)$_2$—Ph) | — | C$_3$H$_6$ | pyridin-2-yl | — | 5-CF$_3$ |
| N-43 | pyrazol-5-yl | 1-$^n$Bu 3-(3,5-F$_2$—Ph) | — | C$_3$H$_6$ | pyridin-2-yl | — | 5-CF$_3$ |
| N-44 | pyrazol-5-yl | 1-$^n$Bu 3-(3,4,5-F$_3$—Ph) | — | C$_3$H$_6$ | pyridin-2-yl | — | 5-CF$_3$ |
| N-45 | pyrazol-5-yl | 1-(CH$_2$OCH$_3$) | 3-CF$_3$ | C$_3$H$_6$ | pyridin-2-yl | — | 5-CF$_3$ |
| N-46 | pyrazol-5-yl | 1-(CH$_2$OEt) | 3-CF$_3$ | C$_3$H$_6$ | pyridin-2-yl | — | 5-CF$_3$ |
| N-47 | pyrazol-5-yl | 1-(CH$_2$CH$_2$OCH$_3$) | 3-CF$_3$ | C$_3$H$_6$ | pyridin-2-yl | — | 5-CF$_3$ |
| N-48 | pyrazol-5-yl | 1-(CH$_2$CH$_2$OEt) | 3-CF$_3$ | C$_3$H$_6$ | pyridin-2-yl | — | 5-CF$_3$ |
| N-49 | pyrazol-5-yl | 1-(CH$_2$CH(OEt)$_2$) | 3-CF$_3$ | C$_3$H$_6$ | pyridin-2-yl | — | 5-CF$_3$ |
| N-50 | pyrazol-5-yl | 1-(CH$_2$CH$_2$CH(OCH$_3$)$_2$) | 3-CF$_3$ | C$_3$H$_6$ | pyridin-2-yl | — | 5-CF$_3$ |
| N-51 | pyrazol-5-yl | 1-(CH$_2$CH$_2$CH(OEt)$_2$) | 3-CF$_3$ | C$_3$H$_6$ | pyridin-2-yl | — | 5-CF$_3$ |
| N-52 | pyrazol-5-yl | 1-(CH$_2$([1,3]dioxolan-2-yl)) | 3-CF$_3$ | C$_3$H$_6$ | pyridin-2-yl | — | 5-CF$_3$ |
| N-53 | pyrazol-5-yl | 1-(CH$_2$CH(OCH$_3$)$_2$) 3-(3,5-F$_2$—Ph) | — | C$_3$H$_6$ | pyridin-2-yl | — | 5-CF$_3$ |

Physical constants of some of the compounds shown in TABLES 1-6 are shown below. In addition, "vis" means "viscous oil".

Compound H-1: vis; $^1$H-NMR (CDCl$_3$, δ ppm, measuring temperature 25° C.) 8.49 (s, 1H), 7.90-7.86 (m, 1H), 7.39 (d, 0.8H), 7.26 (d, 0.2H), 7.15 (d, 1H), 7.08 (s, 1H), 6.91 (d, 1H), 4.91-4.89 (m, 0.8H), 4.65 (m, 0.2H), 3.78 (d, 2H), 3.59 (brs, 2H), 2.76-2.30 (m, 3H), 2.16-2.04 (m, 3H), 1.83-1.67 (m, 4H), 1.41-1.37 (m, 1H), 1.07 (d-like, 6H)

In addition, it is estimated that Compound H-1 is a mixture of two compounds, which are conformational isomers and represented by the following formulas. One of the compounds is a compound in which the distance between 7-position of methylene and 9-position of pyridyloxy on 9-azabicyclo[3.3.1]nonane ring is smaller, and the other one is a compound in which the distance between 7-position of methylene and 9-position of pyridyl oxyl on 9-azabicyclo[3.3.1] nonane ring is larger.

[Chemical formula 39]

(H-1)

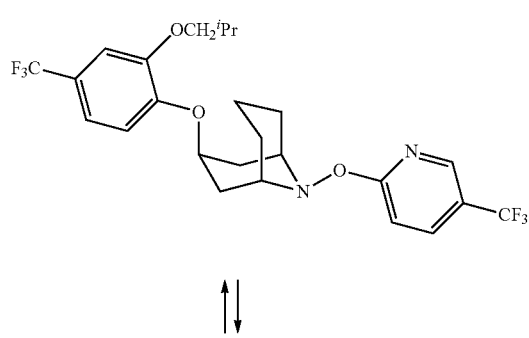

-continued

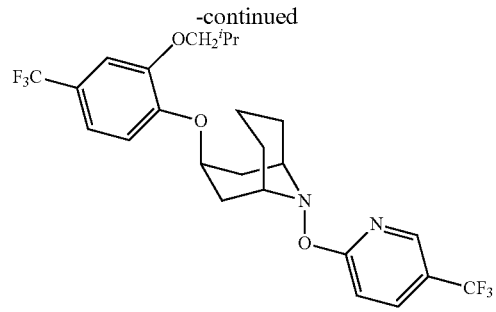

Compound H-2: vis; $^1$H-NMR (CDCl$_3$, δ ppm, measuring temperature 20.2° C.) 8.49 (s, 1H), 7.88 (dd, 1H), 7.39 (d, 1H), 7.17 (d, 1H), 7.08 (s, 1H), 6.95 (d, 1H), 5.00-4.92 (m, 0.8H), 4.67 (m, 0.2H), 3.87 (d, 2H), 3.59 (brs, 2H), 2.75-2.41 (m, 3H), 2.14-2.05 (m, 2H), 1.83-1.71 (m, 3H), 1.43-1.24 (m, 3H), 0.66-0.60 (m, 2H), 0.39-0.35 (m, 2H)

Compound H-5: vis; $^1$H-NMR (CDCl$_3$, δ ppm, measuring temperature: 22.7° C.) 7.77 (d, 1H), 7.68 (d, 1H), 7.17 (d, 1H), 7.08 (s, 1H), 6.91 (d, 1H), 4.95-4.90 (m, 0.7H), 4.63 (m, 0.3H), 3.78 (d, 2H), 3.62 (brs, 2H), 2.80-2.43 (m, 2H), 2.19-2.03 (m, 2H), 1.85-1.75 (m, 2H), 1.41-1.37 (m, 1H), 1.05 (d, 6H)

Compound H-41: vis; $^1$H-NMR (CDCl$_3$, δ ppm, measuring temperature: 20.7° C.) 8.53 (d, 1H), 7.90 (dd, 1H), 7.40 (d, 1H), 7.16 (d, 1H), 7.08 (s, 1H), 6.90 (s, 1H), 4.90-4.85 (m, 0.7H), 4.60 (m, 0.3H), 3.78 (d, 2H), 3.58 (brs, 2H), 2.74-2.40 (m, 3H), 2.18-2.05 (m, 3H), 1.82-1.72 (m, 3H), 1.41-1.34 (m, 2H), 1.06 (d, 6H)

Compound H-42: vis; $^1$H-NMR (CDCl$_3$, δ ppm, measuring temperature: 22.3° C.) 8.49 (s, 1H), 7.88 (dd, 1H), 7.39 (d, 1H), 7.17 (d, 1H), 7.09 (s, 1H), 6.95 (d, 1H), 4.98-4.94 (m, 0.8H), 4.60 (m, 0.2H), 4.10 (q, 2H), 3.59 (brs, 2H), 2.74-2.40 (m, 3H), 2.11-2.05 (m, 2H), 1.81-1.69 (m, 3H), 1.49-1.37 (m, 5H)

Compound H-43: vis; $^1$H-NMR (CDCl$_3$, δ ppm, measuring temperature: 21.3° C.) 8.49 (s, 1H), 7.87 (dd, 1H), 7.39 (d, 1H), 7.17 (d, 1H), 7.09 (s, 1H), 6.92 (d, 1H), 4.95-4.90 (m, 0.9H), 4.60 (m, 0.1H), 3.98 (t, 2H), 3.59 (brs, 2H), 2.75-2.40 (m, 3H), 2.14-2.04 (m, 2H), 1.89-1.69 (m, 6H), 1.41-1.36 (m, 1H), 1.08 (t, 3H)

Compound K-8: vis; $^1$H-NMR (CDCl$_3$, δ ppm, measuring temperature: 21.0° C.) 8.44 (d, 1H), 8.04 (d, 1H), 7.79-7.63 (m, 3H), 6.81 (d, 1H), 5.78 (m, 0.7H), 5.50 (m, 0.3H), 5.32-5.24 (m, 1H), 3.57 (brs, 2H), 2.78-2.68 (m, 2H), 2.42-1.90 (m, 4H), 1.77-1.60 (m, 2H), 1.45-1.26 (m, 8H)

Compound K-12: vis; $^1$H-NMR (CDCl$_3$, δ ppm, measuring temperature: 20.8° C.) 8.43 (s, 1H), 8.07 (d, 1H), 7.76 (dd, 1H), 7.68 (d, 1H), 7.26 (s, 1H), 6.84 (d, 1H), 5.69-5.64 (m, 0.7H), 5.51 (m, 0.3H), 5.33-5.24 (m, 1H), 4.47 (d, 0.5H), 4.00 (dd, 3.5H), 3.54-3.27 (d, d, 2H), 2.85-2.68 (m, 2H), 2.27 (d, 0.3H), 1.91 (d, 1.7H), 1.41 (d, 6H)

Compound H-51: vis; $^1$H-NMR (CDCl$_3$, δ ppm, measuring temperature: 21.2° C.) 8.49 (s, 1H), 7.88 (dd, 1H), 7.40-7.35 (d, d, total 2H), 7.26 (s, 1H), 6.98 (d, 1H), 5.22 (s, 2H), 5.06-5.01 (m, 1H), 3.62 (brs, 2H), 3.53 (s, 3H), 2.75-2.65 (m, 2H), 2.50-2.39 (m, 1H), 2.14-2.04 (m, 2H), 1.79-1.67 (m, 3H), 1.45-1.33 (m, 2H)

Compound H-52: melting point [107-110° C.]

Compound H-53: melting point [141-144° C.]

Compound H-54: vis; $^1$H-NMR (CDCl$_3$, δ ppm, measuring temperature: 21.3° C.) 8.49 (s, 1H), 7.88 (dd, 1H), 7.39 (d, 1H), 7.17 (d, H), 7.08 (s, 1H), 6.92 (d, 1H), 4.93-4.91 (m, 1H), 4.01 (t, 2H), 3.59 (brs, 2H), 2.74-2.40 (m, 3H), 2.14-2.05 (m, 2H), 1.86-1.74 (m, 5H), 1.70-1.49 (m, 2H), 1.41-1.39 (m, 2H), 1.01 (t, 3H)

Compound H-55: vis; $^1$H-NMR (CDCl$_3$, δ ppm, measuring temperature: 21.3° C.) 8.50 (s, 1H), 7.88 (dd, 1H), 7.80 (s, 1H), 7.58 (d, 1H), 7.36 (d, 1H), 6.99 (d, 1H), 6.16 (s, 1H), 5.12-5.09 (m, 1H), 4.19-4.01 (m, 4H), 3.64 (brs, 2H), 2.77-2.03 (m, 3H), 1.80-1.66 (m, 3H), 1.47-1.35 (m, 2H)

Compound H-56: $^1$H-NMR (CDCl$_3$, δ ppm, measuring temperature: 22.1° C.) 8.51 (s, 1H), 7.89 (dd, 1H), 7.71 (s, 1H), 7.49 (d, 1H), 7.38 (d, 1H), 6.92 (d, 1H), 5.08-5.04 (m, 1H), 4.57 (s, 2H), 3.77-3.67 (m, brs, total 3H), 2.79-2.69 (m, 2H), 2.44-2.02 (m, 3H), 1.80-1.59 (m, 3H), 1.48-1.44 (m, 2H), 1.25 (d, 6H)

Compound H-57: vis; $^1$H-NMR (CDCl$_3$, δ ppm, measuring temperature: 21.3° C.) 8.50 (s, 1H), 7.88 (dd, 1H), 7.66 (s, 1H), 7.51 (d, 1H), 7.39 (d, 1H), 6.93 (d, 1H), 5.07-5.03 (m, 1H), 4.52 (s, 2H), 3.65 (brs, 2H), 3.50 (s, 3H), 2.79-2.68 (m, 2H), 2.40-2.02 (m, 3H), 1.80-1.61 (m, 3H), 1.40-1.30 (m, 2H)

Compound H-58: vis; $^1$H-NMR (CDCl$_3$, δ ppm, measuring temperature: 21.3° C.) 8.50 (s, 1H), 7.88 (d, 1H), 7.69 (s, 1H), 7.50 (d, 1H), 7.38 (d, 1H), 6.93 (d, 1H), 5.04 (m, 1H), 4.57 (s, 2H), 3.66-3.58 (brs, q, total 4H), 2.78-2.68 (m, 2H), 2.40-2.04 (m, 3H), 1.79-1.60 (m, 3H), 1.40-1.33 (m, 2H), 1.26 (t, 3H)

Compound H-59: vis; $^1$H-NMR (CDCl$_3$, δ ppm, measuring temperature: 21.3° C.) 8.50 (s, 1H), 7.88 (dd, 1H), 7.36 (s, 1H), 6.87 (d, 1H), 6.78 (s, 1H), 6.74 (d, 1H), 5.05-5.01 (m, 1H), 4.41 (brt, 1H), 3.64 (brs, 2H), 2.98 (t, 2H), 2.80-2.70 (m, 2H), 2.44-1.90 (m, 4H), 1.80-1.65 (m, 3H), 1.49-1.43 (m, 2H), 1.01 (d, 6H)

Compound H-60: vis; $^1$H-NMR (CDCl$_3$, δ ppm, measuring temperature: 21.2° C.) 8.49 (s, 1H), 7.87 (dd, 1H), 7.39 (d, 1H), 7.18 (d, 1H), 7.13 (s, 1H), 6.94 (d, 1H), 4.97-4.92 (m, 1H), 4.59-4.50 (m, 1H), 3.59 (brs, 2H), 2.74-2.41 (m, 3H), 2.14-2.05 (m, 2H), 1.81-1.69 (m, 3H), 1.42-1.35 (m, d, total 8H)

Compound H-61: vis; $^1$H-NMR (CDCl$_3$, δ ppm, measuring temperature: 21.7° C.) 8.49 (s, 1H), 7.87 (dd, 1H), 7.38 (d, 1H), 7.16 (d, 1H), 7.10 (d, 1H), 6.93 (d, 1H), 4.95-4.91 (m, 1H), 4.36-4.30 (m, 1H), 3.58 (brs, 2H), 2.74-2.40 (m, 3H), 2.13-2.04 (m, 2H), 1.81-1.56 (m, 5H), 1.41-1.33 (m, 2H), 1.31 (d, 3H), 1.00 (t, 3H)

Compound H-62: vis; $^1$H-NMR (CDCl$_3$, δ ppm, measuring temperature: 21.6° C.) 8.49 (s, 1H), 7.88 (dd, 1H), 7.48 (d, 1H), 7.40 (d, 1H), 7.36 (s, 1H), 7.06 (d, 1H), 5.09-5.06 (m, 1H), 5.01-4.93 (m, 1H), 3.62 (brs, 2H), 2.76-2.66 (m, 2H), 2.40-2.05 (m, 3H), 1.77-1.61 (m, 3H), 1.38 (d, 6H), 1.45-1.33 (m, 2H)

Compound H-63: vis; $^1$H-NMR (CDCl$_3$, δ ppm, measuring temperature: 19.7° C.) 8.50 (s, 1H), 7.89 (d, 1H), 7.46 (d, 1H), 7.41-7.38 (d, s, total 2H), 7.19-7.02 (m, 1H), 5.11-5.04 (m, 1H), 4.45 (d, 1H), 3.63 (brs, 2H), 2.76-2.66 (m, 2H), 2.44-2.20 (m, 1H), 2.11-2.05 (m, 2H), 1.80-1.63 (m, 3H), 1.49-1.44 (m, 2H)

Compound H-64: vis; $^1$H-NMR (CDCl$_3$, δ ppm, measuring temperature: 22.2° C.) 8.49 (s, 1H), 7.88 (dd, 1H), 7.38 (d, 1H), 7.20 (d, 1H), 7.10 (s, 1H), 6.96 (d, 1H), 6.11-6.02 (m, 1H), 5.49-5.28 (m, 2H), 5.00-4.99 (m, 1H), 4.60 (d, 2H), 3.61 (brs, 2H), 2.75-2.30 (m, 3H), 1.82-1.69 (m, 3H), 1.45-1.35 (m, 2H)

Compound H-65: vis; $^1$H-NMR (CDCl$_3$, δ ppm, measuring temperature: 22.0° C.) 8.49 (s, 1H), 7.87 (d, 1H), 7.38 (d, 1H), 7.17 (d, 1H), 7.10 (s, 1H), 6.96 (d, 1H), 5.47 (t, 2H), 5.01-4.95 (m, 1H), 4.58 (d, 2H), 3.59 (brs, 2H), 2.73-2.40 (m, 3H), 2.14-2.02 (m, 2H), 1.77 (d, 6H), 1.79-1.68 (m, 3H), 1.41-1.37 (m, 2H)

Compound H-66: vis; $^1$H-NMR (CDCl$_3$, δ ppm, measuring temperature: 21.7° C.) 8.49 (s, 1H), 7.88 (dd, 1H), 7.39 (d, 1H), 7.16 (d, 1H), 7.07 (s, 1H), 6.88 (d, 1H), 4.87-4.82 (m, 1H), 3.65 (s, 2H), 3.58 (brs, 2H), 2.78-2.63 (m, 2H), 2.50-2.41 (m, 1H9, 2.17-2.05 (m, 2H), 1.82-1.71 (m, 3H), 1.43-1.36 (m, 2H), 1.08 (s, 9H)

Compound H-67: vis; $^1$H-NMR (CDCl$_3$, δ ppm, measuring temperature: 21.7° C.) 8.49 (s, 1H), 7.88 (dd, 1H), 7.38 (d, 1H), 7.24 (d, 1H), 7.11 (s, 1H), 6.97 (d, 1H), 6.18 (t, 1H), 5.08-5.00 (m, 1H), 4.72 (d, 2H), 3.62 (brs, 2H), 2.74-2.64 (m, 2H), 2.49-2.36 (m, 1H), 2.15-2.04 (m, 2H), 1.80-1.66 (m, 3H), 1.45-1.33 (m, 2H)

Compound H-68: vis; $^1$H-NMR (CDCl$_3$, δ ppm, measuring temperature: 21.7° C.) 8.49 (s, 1H), 7.87 (dd, 1H), 7.38 (d, 1H), 7.27-7.25 (d, s, total 2H), 6.98 (d, 1H), 5.09-5.01 (m, 1H), 4.77 (s, 2H), 3.63 (brs, 2H), 2.74-2.59 (m, 2H), 2.54 (s, 1H), 2.53-2.35 (m, 1H), 2.13-2.01 (m, 2H), 1.81-1.67 (m, 3H), 1.45-1.33 (m, 2H)

Compound H-69: vis; $^1$H-NMR (CDCl$_3$, δ ppm, measuring temperature: 21.9° C.) 8.49 (s, 1H), 7.87 (dd, 1H), 7.38 (d, 1H), 7.17 (d, 1H), 7.10 (s, 1H), 6.93 (d, 1H), 5.14 (s, 1H), 5.00 (s, 1H), 4.98-4.93 (m, 1H), 4.48 (s, 2H), 3.59 (brs, 2H), 2.76-2.40 (m, 3H), 2.15-2.03 (m, 2H), 1.85 (s, 3H), 1.80-1.70 (m, 3H), 1.43-1.34 (m, 2H)

Compound H-70: vis; $^1$H-NMR (CDCl$_3$, δ ppm, measuring temperature: 21.5° C.) 8.49 (s, 1H), 7.88 (dd, 1H), 7.38 (d, 1H), 7.16 (d, 1H), 7.07 (s, 1H), 6.90 (d, 1H), 4.90-4.88 (m, 1H), 3.89-3.77 (m, 2H), 3.59 (brs, 2H), 2.76-2.30 (m, 3H), 2.20-2.05 (m, 2H), 1.92-1.55 (m, 6H), 1.40-1.26 (m, 2H), 1.06 (d, 3H), 0.97 (t, 3H)

Compound H-71: vis; $^1$H-NMR (CDCl$_3$, δ ppm, measuring temperature: 21.8° C.) 8.50 (s, 1H), 7.89 (dd, 1H), 7.38 (d, 1H), 7.30 (s, 1H), 7.06 (d, 1H), 5.17-5.13 (m, 1H), 4.86 (s, 2H), 3.68 (brs, 2H), 2.77-2.66 (m, 2H), 2.46-2.02 (m, 3H), 1.80-1.62 (m, 3H), 1.50-1.45 (m, 2H)

Compound H-72: $^{1}$H-NMR (CDCl$_3$, δ ppm, measuring temperature: 21.1° C.) 8.49 (s, 1H), 7.88 (dd, 1H), 7.39 (d, 1H), 7.32 (s, 1H), 7.25 (d, 1H), 6.98 (d, 1H), 5.33 (q, 1H), 5.04-5.02 (m, 1H), 3.63 (brs, 2H), 3.44 (s, 3H), 2.76-2.65 (m, 2H), 2.50-2.40 (m, 1H), 2.17-2.07 (m, 2H), 1.80-1.68 (m, 3H), 1.53 (d, 3H), 1.50-1.30 (m, 2H)

Compound H-73: melting point [87-89° C.]

Compound H-74: melting point [93-97° C.]

Compound H-75: melting point [102-105° C.]

Compound H-76: melting point [114-117° C.]

Compound H-77: $^{1}$H-NMR (CDCl$_3$, δ ppm, measuring temperature: 21.3° C.) 8.50 (s, 1H), 7.88 (dd, 1H), 7.48 (d, 1H), 7.37 (d, 1H), 7.32 (s, 1H), 7.04 (d, 1H), 5.30-5.01 (m, 1H), 3.62 (brs, 2H), 2.77-2.67 (m, 2H), 2.46-2.10 (m, 3H), 2.26 (s, 3H), 1.77-1.41 (m, 5H)

Compound H-78: $^{1}$H-NMR (CDCl$_3$, δ ppm, measuring temperature: 21.2° C.) 8.48 (s, 1H), 7.86 (dd, 1H), 7.38-7.23 (m, 8H), 6.97 (d, 1H), 4.99-4.95 (m, 1H), 4.50 (q, 1H), 4.37 (d, 2H), 3.56 (brs, 2H), 2.73 (d, 1H), 2.73-2.64 (m, 2H), 2.54-2.47 (m, 1H), 2.09-1.99 (m, 2H), 1.74-1.68 (m, 3H), 1.47-1.35 (m, 2H)

Compound H-79: $^{1}$H-NMR (CDCl$_3$, δ ppm, measuring temperature: 21.8° C.) 8.50 (s, 1H), 7.88 (dd, 1H), 7.39 (d, 1H), 7.28 (d, 1H), 7.04 (s, 1H), 6.98 (d, 1H), 5.07-5.04 (m, 1H), 4.57 (s, 2H), 3.60 (brs, 2H), 2.78-2.35 (m, 3H), 2.35 (s, 3H), 2.27-2.07 (m, 2H), 1.79-1.61 (m, 3H), 1.58-1.40 (m, 2H)

Compound H-80: $^{1}$H-NMR (CDCl$_3$, δ ppm, measuring temperature: 21.4° C.) 8.49 (s, 1H), 7.88 (dd, 1H), 7.39 (d, 1H), 7.21 (d, 1H), 7.14 (s, 1H), 6.97 (d, 1H), 5.14-5.10 (m, 1H), 4.23-4.19 (m, 1H), 4.09-4.03 (m, 1H), 3.87-3.82 (m, 1H), 3.63 (brs, 2H), 2.96 (d, 1H), 2.75-2.41 (m, 3H), 2.13-2.06 (m, 2H), 1.79-1.60 (m, 3H), 1.4

Compound H-81: $^{1}$H-NMR (CDCl$_3$, δ ppm, measuring temperature: 22.0° C.) 8.49 (s, 1H), 7.88 (dd, 1H), 7.38 (d, 1H), 7.18 (d, 1H), 7.10 (s, 1H), 6.92 (d, 1H), 4.95-4.93 (m, 1H), 4.04-4.01 (m, 1H), 3.94-3.89 (m, 1H), 3.78-3.73 (m, 1H), 3.60 (brs, 2H), 3.46 (s, 3H), 2.76-2.50 (m, 3H), 2.11-2.04 (m, 2H), 1.80-1.68 (m, 3H), 1.4

Compound H-82: $^{1}$H-NMR (CDCl$_3$, δ ppm, measuring temperature: 21.7° C.) 8.49 (s, 1H), 7.87 (dd, 1H), 7.38 (d, 1H), 7.15 (d, 1H), 7.13 (s, 1H), 6.92 (d, 1H), 4.90-4.84 (m, 1H), 4.83-4.79 (m, 1H), 3.58 (brs, 2H), 2.74-2.60 (m, 2H), 2.41-2.08 (m, 3H), 1.91-1.63 (m, 11H), 1.38-1.34 (m, 2H)

Compound H-83: $^{1}$H-NMR (CDCl$_3$, δ ppm, measuring temperature: 21.2° C.) 8.49 (s, 1H), 7.87 (dd, 1H), 7.44 (d, 1H), 7.38-7.36 (m, 2H), 7.03 (d, 1H), 5.07 (m, 1H), 4.95 (d, 1H), 3.92-3.86 (m, 1H), 3.62 (brs, 2H), 2.75-2.65 (m, 2H), 2.44-2.01 (m, 3H), 1.77-1.61 (m, 3H), 1.43-1.34 (m, 2H). 1.30 (d, 6H)

Compound H-84: melting point [127-130° C.]

Compound H-85: $^{1}$H-NMR (CDCl$_3$, δ ppm, measuring temperature: 23.3° C.) 8.48 (s, 1H), 7.86 (dd, 1H), 7.58-7.52 (m, 4H), 7.49-7.33 (m, 4H), 7.03 (d, 1H), 5.02 (m, 1H), 3.53 (brs, 2H), 2.71-2.61 (m, 2H), 2.25-1.89 (m, 3H), 1.62-1.51 (m, 3H), 1.50-1.40 (m, 2H).

Compound H-86: $^{1}$H-NMR (CDCl$_3$, δ ppm, measuring temperature: 23.1° C.) 8.79 (s, 1H), 8.59 (t, 1H), 8.49 (s, 1H), 7.89-7.81 (m, 1H), 7.65-7.57 (dd, s, total 2H), 7.38-7.34 (m, 2H), 7.09 (d, 1H), 5.11 (m, 1H), 3.56 (brs, 2H), 2.74-2.64 (m, 2H), 2.25-1.90 (m, 3H), 1.70-1.54 (m, 3H), 1.26-1.00 (m, 2H).

Compound H-87: $^{1}$H-NMR (CDCl$_3$, δ ppm, measuring temperature: 21.8° C.) 8.50 (s, 1H), 7.89 (dd, 1H), 7.41-7.36 (d, d, s, total 3H), 6.90 (d, 1H), 5.07-5.05 (m, 1H), 3.64 (brs, 2H), 2.87 (t, 2H), 2.75-2.68 (m, 2H), 2.45-2.08 (m, 3H), 1.83-1.42 (m, 7H). 1.08 (t, 3H)

Compound H-88: $^{1}$H-NMR (CDCl$_3$, δ ppm, measuring temperature: 22.0° C.) 8.33 (s, 1H), 7.74 (dd, 1H), 7.58 (d, 1H), 7.47 (s, 1H), 7.32 (d, 1H), 7.18 (d, 1H), 5.80-5.66 (m, 1H), 5.30-5.05 (m, 3H), 3.68 (brs, 2H), 2.97-2.85 (m, 2H), 2.77-2.39 (m, 2H), 2.39-2.00 (m, 3H), 1.79-1.26 (m, 5H)

Compound H-89: $^{1}$H-NMR (CDCl$_3$, δ ppm, measuring temperature: 23.5° C.) 8.48 (s, 1H), 7.87 (dd, 1H), 7.37 (d, 1H), 6.91-6.83 (m, 3H), 4.82-4.77 (m, 1H), 3.94 (t, 2H), 3.57 (brs, 2H), 2.69-230 (m, 3H), 2.12-2.04 (m, 2H), 1.89-1.60 (m, 5H), 1.41-1.32 (m, 2H), 1.07 (t, 3H)

Compound H-90: $^{1}$H-NMR (CDCl$_3$, δ ppm, measuring temperature: 20.8° C.) 8.49 (s, 1H), 7.91 (dd, 1H), 7.48 (d, 1H), 7.17 (d, 1H), 7.08 (s, 1H), 6.99 (d, 1H), 5.02-4.98 (m, 1H), 3.98 (t, 2H), 3.60-3.58 (m, 2H), 2.58-2.49 (m, 2H), 2.30-2.20 (m, 2H), 1.91-1.75 (m, 7H), 1.07 (t, 3H)

Compound H-29: $^{1}$H-NMR (CDCl$_3$, δ ppm, measuring temperature: 20.4° C.) 8.50 (s, 1H), 7.89 (dd, 1H), 7.38 (d, 1H), 7.16 (d, 1H), 7.09 (s, 1H), 7.03 (d, 1H), 4.97-4.95 (m, 1H), 3.97 (q, 4H), 3.79 (d, 2H), 3.58-3.33 (ddd, 2H), 2.74-2.65 (m, 2H), 2.19-2.12 (m, 1H), 1.98 (brd, 2H), 1.06 (d, 6H)

Compound J-42: melting point [170-172° C.]

Compound K-38: $^{1}$H-NMR (CDCl$_3$, δ ppm, measuring temperature: 21.5° C.) 8.49 (s, 1H), 7.88 (dd, 1H), 7.39 (d, 1H), 7.19 (d, 1H), 7.07 (d, 1H), 4.98-4.93 (m, 1H), 4.34 (t, 2H), 3.60 (brs, 2H), 2.75-2.30 (m, 3H), 2.14-2.07 (m, 2H), 1.86-1.67 (m, 5H), 1.44-1.38 (m, 2H), 1.04 (t, 3H)

Compound K-39: $^{1}$H-NMR (CDCl$_3$, δ ppm, measuring temperature: 22.3° C.) 8.51 (s, 1H), 7.90 (dd, 1H), 7.38 (d, 1H), 5.78 (s, 1H), 5.10-4.80 (m, 1H), 4.00 (t, 2H), 3.66 (brs, 2H), 2.75-1.20 (m, 14H), 0.97 (t, 3H)

Compound N-1: $^{1}$H-NMR (CDCl$_3$, δ ppm, measuring temperature: 20.8° C.) 8.64 (s, 1H), 7.85-7.81 (m, 1H), 7.74-7.69 (m, 1H), 7.17 (d, 1H), 7.08 (s, 1H), 6.92 (d, 1H), 4.69 (m, 1H), 3.80 (d, 2H), 3.36 (brs, 2H), 2.61-2.56 (m, 2H), 2.17-2.05 (m, 3H), 1.91-1.86 (m, 1H), 1.65-1.53 (m, 3H), 1.27-1.26 (m, 2H), 1.08 (d, 6H)

Compound H-92: $^{1}$H-NMR (CDCl$_3$, δ ppm, measuring temperature: 21.3° C.) 8.50 (s, 1H), 7.88 (d, 1H), 7.37 (d, 1H), 7.31 (d, 1H), 6.84 (d, 1H), 5.11-5.07 (m, 0.8H), 4.75 (m, 0.2H), 3.88 (s, 3H), 3.66 (brs, 2H), 2.77-2.67 (m, 4H), 2.50-2.25 (m, 1H), 2.13-2.04 (m, 3H), 1.80-1.48 (m, 6H), 1.02 (t, 3H)

Compound H-93: $^{1}$H-NMR (CDCl$_3$, δ ppm, measuring temperature: 20.2° C.) 8.49 (s, 1H), 7.87 (dd, 1H), 7.38 (d, 1H), 7.05 (d, 1H), 6.85 (d, 1H), 5.20-4.80 (m, 2H), 3.61 (brs, 2H), 3.52-3.44 (m, 1H), 3.01-2.90 (m, 1H), 2.70-2.33 (m, 3H), 2.10-2.01 (m, 3H), 1.79-1.55 (m, 4H), 1.48 (d, 3H)

Next, examples of the hydroxylamine compound suitable to be used as a production intermediate of the cyclic amine compound of the present invention are shown in TABLES 15-20. In addition, these hydroxylamine compounds are substances formed at intermediate steps of a method similar to the production methods shown in the aforementioned Examples.

In TABLE 7, $(R^{10})_m$, $(R^{11})_n$ and A represent the substituents in the hydroxylamine compound represented by formula (IIId).

In TABLE 8, $(R^{10})_m$, $(R^{11})_n$ and A represent the substituents in the hydroxylamine compound represented by formula (IIIr).

[Chemical formula 40]

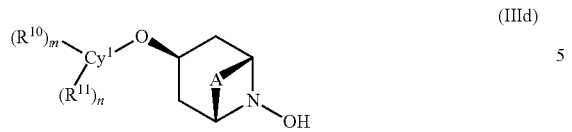

(IIId)

TABLE 7

| No. | Cy$^1$ | (R$^{10}$)$_m$ | (R$^{11}$)$_n$ | A |
|---|---|---|---|---|
| e-1 | Ph | 2-(OCH$_2$$^i$Pr) | 4-CF$_3$ | C$_3$H$_6$ |
| e-2 | Ph | 2-(OCH$_2$$^c$Pr) | 4-CF$_3$ | C$_3$H$_6$ |
| e-3 | Ph | 2-(CH$_2$OCH(OCH$_3$)CH$_3$) | 4-CF$_3$ | C$_3$H$_6$ |
| e-4 | Ph | 2-(CO$_2$$^i$Pr) | 4-CF$_3$ | C$_3$H$_6$ |
| e-5 | Ph | 2-(OCH$_2$$^i$Pr) | 4-CF$_3$ | CH$_2$OCH$_2$ |
| e-6 | Ph | 2-(OCH$_2$$^c$Pr) | 4-CF$_3$ | CH$_2$OCH$_2$ |
| e-7 | Ph | 2-(CH$_2$OCH(OCH$_3$)CH$_3$) | 4-CF$_3$ | CH$_2$OCH$_2$ |
| e-8 | Ph | 2-(CO$_2$$^i$Pr) | 4-CF$_3$ | CH$_2$OCH$_2$ |
| e-9 | Ph | 2-(O$^n$Pr) | 4-CF$_3$ | C$_3$H$_6$ |
| e-11 | pyridin-2-yl | — | 5-CF$_3$ | C$_3$H$_6$ |
| e-12 | pyridin-2-yl | — | 5-CF$_3$ | CH$_2$OCH$_2$ |
| e-13 | Ph | 2-(CO$_2$CH$_3$) | 4-CF$_3$ | C$_3$H$_6$ |
| e-14 | Ph | 2-(OCH$_2$OCH$_3$) | 4-CF$_3$ | C$_3$H$_6$ |
| e-15 | Ph | 2-(OCH$_2$$^i$Pr) | 4-CF$_3$ | CH$_2$OCH$_2$ |
| e-16 | Ph | 2-(OCH$_2$$^i$Pr) | 4-CF$_3$ | C$_3$H$_6$ |
| e-17 | pyridin-3-yl | 2-(O$^n$Pr) | 6-CF$_3$ | C$_3$H$_6$ |
| e-18 | pyrazol-5-yl | 1-($^n$Bu) | 3-CF$_3$ | C$_3$H$_6$ |
| e-20 | Ph | 2-(OEt) | 4-CF$_3$ | C$_3$H$_6$ |
| e-22 | Ph | 2-OH | 4-CF$_3$ | C$_3$H$_6$ |
| e-23 | Ph | 2-(O$^n$Bu) | 4-CF$_3$ | C$_3$H$_6$ |
| e-24 | Ph | 2-([1,3]dioxolan-2-yl) | 4-CF$_3$ | C$_3$H$_6$ |
| e-25 | Ph | 2-(CH$_2$O$^i$Pr) | 4-CF$_3$ | C$_3$H$_6$ |
| e-26 | Ph | 2-(CH$_2$OCH$_3$) | 4-CF$_3$ | C$_3$H$_6$ |
| e-27 | Ph | 2-(CH$_2$OEt) | 4-CF$_3$ | C$_3$H$_6$ |
| e-28 | Ph | 2-(NHCH$_2$$^i$Pr) | 4-CF$_3$ | C$_3$H$_6$ |
| e-29 | Ph | 2-(O$^i$Pr) | 4-CF$_3$ | C$_3$H$_6$ |
| e-30 | Ph | 2-(O$^s$Bu) | 4-CF$_3$ | C$_3$H$_6$ |
| e-31 | Ph | 2-(OCO$_2$$^i$Pr) | 4-CF$_3$ | C$_3$H$_6$ |
| e-32 | Ph | 2-(OCH$_2$CF$_3$) | 4-CF$_3$ | C$_3$H$_6$ |
| e-33 | Ph | 2-(OCH$_2$CH=CH$_2$) | 4-CF$_3$ | C$_3$H$_6$ |
| e-34 | Ph | 2-(OCH$_2$CH=C(CH$_3$)$_2$) | 4-CF$_3$ | C$_3$H$_6$ |
| e-35 | Ph | 2-(OCH$_2$$^t$Bu) | 4-CF$_3$ | C$_3$H$_6$ |
| e-36 | Ph | 2-(OCH$_2$CH=CCl$_2$) | 4-CF$_3$ | C$_3$H$_6$ |
| e-37 | Ph | 2-(OCH$_2$C≡CH) | 4-CF$_3$ | C$_3$H$_6$ |
| e-38 | Ph | 2-(OCH$_2$C(CH$_3$)=CH$_2$) | 4-CF$_3$ | C$_3$H$_6$ |
| e-39 | Ph | 2-(OCH$_2$$^s$Bu) | 4-CF$_3$ | C$_3$H$_6$ |
| e-40 | Ph | 2-(OCH$_2$CN) | 4-CF$_3$ | C$_3$H$_6$ |
| e-41 | Ph | 2-(OCH(CH$_3$)OCH$_3$) | 4-CF$_3$ | C$_3$H$_6$ |
| e-42 | Ph | 2-(CO$_2$Et) | 4-CF$_3$ | C$_3$H$_6$ |
| e-43 | Ph | 2-(OAc) | 4-CF$_3$ | C$_3$H$_6$ |
| e-44 | Ph | 2-(OCH$_2$[2,2-Cl$_2$-3-Ph—$^c$Pr]) | 4-CF$_3$ | C$_3$H$_6$ |
| e-45 | Ph | 2-(OCH$_2$Ac) | 4-CF$_3$ | C$_3$H$_6$ |
| e-46 | Ph | 2-(OCH$_2$CH(OH)CH$_3$) | 4-CF$_3$ | C$_3$H$_6$ |
| e-47 | Ph | 2-(OCH$_2$CH(OCH$_3$)CH$_3$) | 4-CF$_3$ | C$_3$H$_6$ |
| e-48 | Ph | 2-(O$^c$Pen) | 4-CF$_3$ | C$_3$H$_6$ |
| e-49 | Ph | 2-(OCONH$^i$Pr) | 4-CF$_3$ | C$_3$H$_6$ |
| e-50 | Ph | 2-(OSO$_2$CF$_3$) | 4-CF$_3$ | C$_3$H$_6$ |
| e-51 | Ph | 2-Ph | 4-CF$_3$ | C$_3$H$_6$ |
| e-52 | Ph | 2-(pyridin-3-yl) | 4-CF$_3$ | C$_3$H$_6$ |
| e-53 | Ph | 2-(S$^n$Pr) | 4-CF$_3$ | C$_3$H$_6$ |
| e-54 | Ph | 2-(CH$_2$CH=CH$_2$) | 4-CF$_3$ | C$_3$H$_6$ |
| e-55 | Ph | 2-(O$^n$Pr) | 4-Cl | C$_3$H$_6$ |
| e-56 | Ph | 2-(OCH$_2$$^i$Pr) | 4-Cl | CH$_2$OCH$_2$ |
| e-57 | Ph | 2-$^n$Bu | 4-CF$_3$ | C$_3$H$_6$ |
| e-58 | Ph | 2-$^i$Pen | 4-CF$_3$ | C$_3$H$_6$ |
| e-59 | Ph | 2-(CH$_2$CH$_2$C≡CH) | 4-CF$_3$ | C$_3$H$_6$ |
| e-60 | Ph | 2-(CH=N—OH) | 4-CF$_3$ | C$_3$H$_6$ |
| e-61 | Ph | 2-(CH=N—OCH$_3$) | 4-CF$_3$ | C$_3$H$_6$ |
| e-62 | Ph | 2-(OCH$_2$CH(OCH$_3$)$_2$) | 4-CF$_3$ | C$_3$H$_6$ |
| e-63 | Ph | 2-(OCH$_2$CH$_2$SO$_2$CH$_3$) | 4-CF$_3$ | C$_3$H$_6$ |
| e-64 | Ph | 2-(OCH$_2$Ph) | 4-CF$_3$ | C$_3$H$_6$ |
| e-65 | Ph | 2-(OCH$_2$-(pyridin-3-yl)) | 4-CF$_3$ | C$_3$H$_6$ |
| e-66 | Ph | 2-(OCH$_2$-[tetrahydrofuran-2-yl]) | 4-CF$_3$ | C$_3$H$_6$ |
| e-67 | Ph | 2-(SCH$_2$CH=CH$_2$) | 4-CF$_3$ | C$_3$H$_6$ |
| e-68 | Ph | 2-(SCH$_2$C≡CH) | 4-CF$_3$ | C$_3$H$_6$ |

TABLE 7-continued

| No. | Cy¹ | $(R^{10})_m$ | $(R^{11})_n$ | A |
|---|---|---|---|---|
| e-69 | Ph | 2-($SO_2CH_3$) | 4-$CF_3$ | $C_3H_6$ |
| e-70 | Ph | 2-($SO_2CH_2CH=CH_2$) | 4-$CF_3$ | $C_3H_6$ |
| e-71 | Ph | 2-(OPh) | 4-$CF_3$ | $C_3H_6$ |
| e-72 | Ph | 2-(O-(pyridin-3-yl)) | 4-$CF_3$ | $C_3H_6$ |
| e-73 | Ph | 2-$NH_2$ | 4-$CF_3$ | $C_3H_6$ |
| e-74 | Ph | 2-(N($CH_3$)$^i$Pr) | 4-$CF_3$ | $C_3H_6$ |
| e-75 | Ph | 2-($NHCH_2CH=CH_2$) | 4-$CF_3$ | $C_3H_6$ |
| e-76 | Ph | 2-($NHCH_2C\equiv CH$) | 4-$CF_3$ | $C_3H_6$ |
| e-77 | Ph | 2-(NHAc) | 4-$CF_3$ | $C_3H_6$ |
| e-78 | Ph | 2-($NHSO_2CH_3$) | 4-$CF_3$ | $C_3H_6$ |
| e-79 | Ph | 2-($NHSO_2Ph$) | 4-$CF_3$ | $C_3H_6$ |
| e-80 | Ph | 2-($CONH_2$) | 4-$CF_3$ | $C_3H_6$ |
| e-81 | Ph | 2-(O—N=C($CH_3$)$_2$) | 4-$CF_3$ | $C_3H_6$ |
| e-82 | Ph | 2-(SPh) | 4-$CF_3$ | $C_3H_6$ |
| e-83 | Ph | 2-(S-(pyridin-3-yl)) | 4-$CF_3$ | $C_3H_6$ |
| e-84 | Ph | 2-(CS$^i$Pr) | 4-$CF_3$ | $C_3H_6$ |
| e-85 | Ph | 2-(CO(S$^i$Pr)) | 4-$CF_3$ | $C_3H_6$ |
| e-86 | Ph | 2-(CS(O$^i$Pr)) | 4-$CF_3$ | $C_3H_6$ |
| e-87 | Ph | 2-($CS_2$$^i$Pr) | 4-$CF_3$ | $C_3H_6$ |
| e-88 | Ph | 2-(Si($CH_3$)$_3$) | 4-$CF_3$ | $C_3H_6$ |
| e-89 | Ph | 2-$NO_2$ | 4-$CF_3$ | $C_3H_6$ |
| e-90 | Ph | 2-($OCH_2CO_2CH_3$) | 4-$CF_3$ | $C_3H_6$ |
| e-91 | Ph | 2-($OCH_2CH_2$)-3 | 4-$CF_3$ | $C_3H_6$ |
| e-92 | Ph | 2-($OCH_2CH_2O$)-3 | 4-$CF_3$ | $C_3H_6$ |
| e-93 | Ph | 2-($OCH_2O$)-3 | 4-$CF_3$ | $C_3H_6$ |
| e-94 | Ph | 2-($CH_2OCH_2CF_3$) | 4-$CF_3$ | $C_3H_6$ |
| e-95 | Ph | 2-($CH_2OCH_2CN$) | 4-$CF_3$ | $C_3H_6$ |
| e-96 | Ph | 2-($CH_2OCH_2OCH_3$) | 4-$CF_3$ | $C_3H_6$ |
| e-97 | Ph | 2-($CH_2OCH_2O^c$Pen) | 4-$CF_3$ | $C_3H_6$ |
| e-98 | Ph | 2-($CH_2OCH_2Ac$) | 4-$CF_3$ | $C_3H_6$ |
| e-99 | Ph | 2-($CH_2OCH_2CH(OCH_3)_2$) | 4-$CF_3$ | $C_3H_6$ |
| e-100 | Ph | 2-($CH_2OCH_2SO_2CH_3$) | 4-$CF_3$ | $C_3H_6$ |
| e-101 | Ph | 2-($CH_2OCH_2Ph$) | 4-$CF_3$ | $C_3H_6$ |
| e-102 | Ph | 2-($CH_2OCH_2$-(pyridin-3-yl)) | 4-$CF_3$ | $C_3H_6$ |
| e-103 | Ph | 2-($CH_2OCH_2$-[tetrahydrofuran-2-yl]) | 4-$CF_3$ | $C_3H_6$ |
| e-104 | Ph | 3-($OCH_2$$^i$Pr) | 4-$CF_3$ | $C_3H_6$ |
| e-105 | Ph | 3-($OCH_2$$^c$Pr) | 4-$CF_3$ | $C_3H_6$ |
| e-106 | Ph | 3-($CH_2OCH(OCH_3)CH_3$) | 4-$CF_3$ | $C_3H_6$ |
| e-107 | Ph | 3-($CO_2$$^i$Pr) | 4-$CF_3$ | $C_3H_6$ |
| e-108 | Ph | 3-(O$^n$Pr) | 4-$CF_3$ | $C_3H_6$ |
| e-109 | Ph | 2-($OCH_2$$^i$Pr) | 4-CN | $C_3H_6$ |
| e-110 | Ph | 2-($OCH_2$$^c$Pr) | 4-CN | $C_3H_6$ |
| e-111 | Ph | 2-($CH_2OCH(OCH_3)CH_3$) | 4-CN | $C_3H_6$ |
| e-112 | Ph | 2-($CO_2$$^i$Pr) | 4-CN | $C_3H_6$ |
| e-113 | Ph | 2-(O$^n$Pr) | 4-CN | $C_3H_6$ |

[Chemical formula 41]

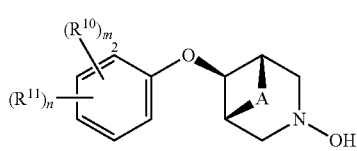

(IIIe)

TABLE 8

| No. | $(R^{10})_m$ | $(R^{11})_n$ | A |
|---|---|---|---|
| f-5 | 2-($OCH_2$$^i$Pr) | 4-$CF_3$ | $C_3H_6$ |
| f-6 | 2-($OCH_2$$^c$Pr) | 4-$CF_3$ | $C_3H_6$ |
| f-7 | 2-($CH_2OCH(OCH_3)CH_3$) | 4-$CF_3$ | $C_3H_6$ |
| f-8 | 2-($CO_2$$^i$Pr) | 4-$CF_3$ | $C_3H_6$ |
| f-9 | 2-($OCH_2$$^i$Pr) | 4-$CF_3$ | $CH_2OCH_2$ |
| f-10 | 2-($OCH_2$$^c$Pr) | 4-$CF_3$ | $CH_2OCH_2$ |
| f-11 | 2-($CH_2OCH(OCH_3)CH_3$) | 4-$CF_3$ | $CH_2OCH_2$ |
| f-12 | 2-($CO_2$$^i$Pr) | 4-$CF_3$ | $CH_2OCH_2$ |
| f-13 | 2-(OEt) | 4-$CF_3$ | $C_3H_6$ |
| f-14 | 2-OH | 4-$CF_3$ | $C_3H_6$ |
| f-15 | 2-(O$^n$Bu) | 4-$CF_3$ | $C_3H_6$ |
| f-16 | 2-([1,3]dioxolan-2-yl) | 4-$CF_3$ | $C_3H_6$ |
| f-17 | 2-($CH_2O$$^i$Pr) | 4-$CF_3$ | $C_3H_6$ |
| f-18 | 2-($CH_2OCH_3$) | 4-$CF_3$ | $C_3H_6$ |
| f-19 | 2-($CH_2OEt$) | 4-$CF_3$ | $C_3H_6$ |
| f-20 | 2-(NHCH$_2$$^i$Pr) | 4-$CF_3$ | $C_3H_6$ |
| f-21 | 2-(O$^i$Pr) | 4-$CF_3$ | $C_3H_6$ |
| f-22 | 2-(O$^s$Bu) | 4-$CF_3$ | $C_3H_6$ |
| f-23 | 2-($OCO_2$$^i$Pr) | 4-$CF_3$ | $C_3H_6$ |
| f-24 | 2-($OCH_2CF_3$) | 4-$CF_3$ | $C_3H_6$ |
| f-25 | 2-($OCH_2CH=CH_2$) | 4-$CF_3$ | $C_3H_6$ |
| f-26 | 2-($OCH_2CH=C(CH_3)_2$) | 4-$CF_3$ | $C_3H_6$ |
| f-27 | 2-($OCH_2$$^t$Bu) | 4-$CF_3$ | $C_3H_6$ |
| f-28 | 2-($OCH_2CH=CCl_2$) | 4-$CF_3$ | $C_3H_6$ |
| f-29 | 2-($OCH_2C\equiv CH$) | 4-$CF_3$ | $C_3H_6$ |
| f-30 | 2-($OCH_2C(CH_3)=CH_2$) | 4-$CF_3$ | $C_3H_6$ |
| f-31 | 2-($OCH_2$$^s$Bu) | 4-$CF_3$ | $C_3H_6$ |
| f-32 | 2-($OCH_2CN$) | 4-$CF_3$ | $C_3H_6$ |
| f-33 | 2-($OCH(CH_3)OCH_3$) | 4-$CF_3$ | $C_3H_6$ |
| f-34 | 2-($CO_2Et$) | 4-$CF_3$ | $C_3H_6$ |
| f-35 | 2-(OAc) | 4-$CF_3$ | $C_3H_6$ |
| f-36 | 2-($OCH_2[2,2-Cl_2-3-Ph-$$^c$Pr]) | 4-$CF_3$ | $C_3H_6$ |
| f-37 | 2-($OCH_2Ac$) | 4-$CF_3$ | $C_3H_6$ |
| f-38 | 2-($OCH_2CH(OH)CH_3$) | 4-$CF_3$ | $C_3H_6$ |
| f-39 | 2-($OCH_2CH(OCH_3)CH_3$) | 4-$CF_3$ | $C_3H_6$ |
| f-40 | 2-(O$^c$Pen) | 4-$CF_3$ | $C_3H_6$ |
| f-41 | 2-(OCONH$^i$Pr) | 4-$CF_3$ | $C_3H_6$ |

TABLE 8-continued

| No. | $(R^{10})_m$ | $(R^{11})_n$ | A |
|---|---|---|---|
| f-42 | 2-($OSO_2CF_3$) | 4-$CF_3$ | $C_3H_6$ |
| f-43 | 2-Ph | 4-$CF_3$ | $C_3H_6$ |
| f-44 | 2-(pyridin-3-yl) | 4-$CF_3$ | $C_3H_6$ |
| f-45 | 2-($S^nPr$) | 4-$CF_3$ | $C_3H_6$ |
| f-46 | 2-($CH_2CH=CH_2$) | 4-$CF_3$ | $C_3H_6$ |
| f-47 | 2-($O^nPr$) | 4-Cl | $C_3H_6$ |
| f-48 | 2-($OCH_2^iPr$) | 4-Cl | $CH_2OCH_2$ |
| f-49 | 2-$^nBu$ | 4-$CF_3$ | $C_3H_6$ |
| f-50 | 2-$^iPen$ | 4-$CF_3$ | $C_3H_6$ |
| f-51 | 2-($CH_2CH_2C\equiv CH$) | 4-$CF_3$ | $C_3H_6$ |
| f-52 | 2-(CH=N—OH) | 4-$CF_3$ | $C_3H_6$ |
| f-53 | 2-(CH=N—$OCH_3$) | 4-$CF_3$ | $C_3H_6$ |
| f-54 | 2-($OCH_2CH(OCH_3)_2$) | 4-$CF_3$ | $C_3H_6$ |
| f-55 | 2-($OCH_2CH_2SO_2CH_3$) | 4-$CF_3$ | $C_3H_6$ |
| f-56 | 2-($OCH_2Ph$) | 4-$CF_3$ | $C_3H_6$ |
| f-57 | 2-($OCH_2$-(pyridin-3-yl)) | 4-$CF_3$ | $C_3H_6$ |
| f-58 | 2-($OCH_2$-[tetrahydrofuran-2-yl]) | 4-$CF_3$ | $C_3H_6$ |
| f-59 | 2-($SCH_2CH=CH_2$) | 4-$CF_3$ | $C_3H_6$ |
| f-60 | 2-($SCH_2C\equiv CH$) | 4-$CF_3$ | $C_3H_6$ |
| f-61 | 2-($SO_2CH_3$) | 4-$CF_3$ | $C_3H_6$ |
| f-62 | 2-($SO_2CH_2CH=CH_2$) | 4-$CF_3$ | $C_3H_6$ |
| f-63 | 2-(OPh) | 4-$CF_3$ | $C_3H_6$ |
| f-64 | 2-(O-(pyridin-3-yl)) | 4-$CF_3$ | $C_3H_6$ |
| f-65 | 2-$NH_2$ | 4-$CF_3$ | $C_3H_6$ |
| f-66 | 2-(N($CH_3$)$^iPr$) | 4-$CF_3$ | $C_3H_6$ |
| f-67 | 2-($NHCH_2CH=CH_2$) | 4-$CF_3$ | $C_3H_6$ |
| f-68 | 2-($NHCH_2C\equiv CH$) | 4-$CF_3$ | $C_3H_6$ |
| f-69 | 2-(NHAc) | 4-$CF_3$ | $C_3H_6$ |
| f-70 | 2-($NHSO_2CH_3$) | 4-$CF_3$ | $C_3H_6$ |
| f-71 | 2-($NHSO_2Ph$) | 4-$CF_3$ | $C_3H_6$ |
| f-72 | 2-($CONH_2$) | 4-$CF_3$ | $C_3H_6$ |
| f-73 | 2-(O—N=C($CH_3$)$_2$) | 4-$CF_3$ | $C_3H_6$ |
| f-74 | 2-(SPh) | 4-$CF_3$ | $C_3H_6$ |
| f-75 | 2-(S-(pyridin-3-yl)) | 4-$CF_3$ | $C_3H_6$ |
| f-76 | 2-($CS^iPr$) | 4-$CF_3$ | $C_3H_6$ |
| f-77 | 2-(CO($S^iPr$)) | 4-$CF_3$ | $C_3H_6$ |
| f-78 | 2-(CS($O^iPr$)) | 4-$CF_3$ | $C_3H_6$ |
| f-79 | 2-($CS_2^iPr$) | 4-$CF_3$ | $C_3H_6$ |
| f-80 | 2-(Si($CH_3$)$_3$) | 4-$CF_3$ | $C_3H_6$ |
| f-81 | 2-$NO_2$ | 4-$CF_3$ | $C_3H_6$ |
| f-82 | 2-($OCH_2CO_2CH_3$) | 4-$CF_3$ | $C_3H_6$ |
| f-83 | 2-($OCH_2CH_2$)-3 | 4-$CF_3$ | $C_3H_6$ |
| f-84 | 2-($OCH_2CH_2O$)-3 | 4-$CF_3$ | $C_3H_6$ |
| f-85 | 2-($OCH_2O$)-3 | 4-$CF_3$ | $C_3H_6$ |
| f-86 | 2-($CH_2OCH_2CF_3$) | 4-$CF_3$ | $C_3H_6$ |
| f-87 | 2-($CH_2OCH_2CN$) | 4-$CF_3$ | $C_3H_6$ |
| f-88 | 2-($CH_2OCH_2OCH_3$) | 4-$CF_3$ | $C_3H_6$ |
| f-89 | 2-($CH_2OCH_2O^cPen$) | 4-$CF_3$ | $C_3H_6$ |
| f-90 | 2-($CH_2OCH_2Ac$) | 4-$CF_3$ | $C_3H_6$ |
| f-91 | 2-($CH_2OCH_2CH(OCH_3)_2$) | 4-$CF_3$ | $C_3H_6$ |
| f-92 | 2-($CH_2OCH_2SO_2CH_3$) | 4-$CF_3$ | $C_3H_6$ |
| f-93 | 2-($CH_2OCH_2Ph$) | 4-$CF_3$ | $C_3H_6$ |
| f-94 | 2-($CH_2OCH_2$-(pyridin-3-yl)) | 4-$CF_3$ | $C_3H_6$ |
| f-95 | 2-($CH_2OCH_2$-[tetrahydrofuran-2-yl]) | 4-$CF_3$ | $C_3H_6$ |
| f-96 | 3-($OCH_2^iPr$) | 4-$CF_3$ | $C_3H_6$ |
| f-97 | 3-($OCH_2^cPr$) | 4-$CF_3$ | $C_3H_6$ |
| f-98 | 3-($CH_2OCH(OCH_3)CH_3$) | 4-$CF_3$ | $C_3H_6$ |
| f-99 | 3-($CO_2^iPr$) | 4-$CF_3$ | $C_3H_6$ |
| f-100 | 3-($O^nPr$) | 4-$CF_3$ | $C_3H_6$ |
| f-101 | 2-($OCH_2^iPr$) | 4-CN | $C_3H_6$ |
| f-102 | 2-($OCH_2^cPr$) | 4-CN | $C_3H_6$ |
| f-103 | 2-($CH_2OCH(OCH_3)CH_3$) | 4-CN | $C_3H_6$ |
| f-104 | 2-($CO_2^iPr$) | 4-CN | $C_3H_6$ |
| f-105 | 2-($O^nPr$) | 4-CN | $C_3H_6$ |

Physical constants of some of the compounds in TABLES 7-8 are shown below.

Compound e-1: melting point [112-115° C.]
Compound e-2: melting point [118-123° C.]
Compound e-9: melting point [94-100° C.]
Compound e-11: melting point [105-110° C.]
Compound e-12: melting point [110-113° C.]
Compound e-13: $^1$H-NMR ($CDCl_3$, δ ppm, measuring temperature 20.2° C.) 8.02 (s, 1H), 7.70 (d, 1H), 7.05 (d, 1H), 5.70-5.66 (m, 1H), 3.96 (s, 3H), 3.52 (brs, 2H), 2.74-2.64 (m, 2H), 2.37-2.34 (m, 1H), 1.98-1.80 (m, 2H), 1.71-1.34 (m, 5H)

Compound e-14: $^1$H-NMR ($CDCl_3$, δ ppm, measuring temperature 20.4° C.) 7.34 (s, 1H), 7.23 (d, 1H), 6.95 (d, 1H), 5.21 (s, 2H), 5.08-5.00 (m, 1H), 3.56-3.51 (brs, s, total 5H), 2.70-2.60 (m, 2H), 2.38-2.26 (m, 1H), 2.02-1.96 (m, 2H), 1.71-1.57 (m, 3H), 1.40-1.33 (m, 2H)

Compound e-15: melting point [104-107° C.]
Compound e-16: melting point [112-115° C.]
Compound e-17: $^1$H-NMR ($CDCl_3$, δ ppm, measuring temperature 21.7° C.) 7.17 (d, 1H), 7.07 (d, 1H), 5.01-4.97 (m, 1H), 4.35 (t, 2H), 3.47 (brs, 2H), 2.65-1.23 (m, 12H), 1.03 (t, 3H)

Compound e-18: $^1$H-NMR ($CDCl_3$, δ ppm, measuring temperature 22.6° C.) 5.78 (s, 1H), 5.30-4.90 (m, 1H), 3.99 (t, 2H), 3.50 (brs, 2H), 2.66-2.29 (m, 3H), 1.96-1.15 (m, 11H), 0.95 (t, 3H)

Some preparation examples of the acaricide according to the present invention are shown below. However, additives and addition ratios are not limited to the preparation examples, and can be modified over a wide range. Moreover, the term "parts" used in the preparation examples indicates "weight parts."

Preparation Example 1

Wettable Powder

| | |
|---|---|
| Compound of the present invention | 40 parts |
| Diatom earth | 53 parts |
| Fatty alcohol sulfate | 4 parts |
| Alkylnaphtalene sulfonate | 3 parts |

The foregoing is uniformly mixed and finely pulverized to obtain a wettable powder including 40% of active ingredient.

Preparation Example 2

Emulsion

| | |
|---|---|
| Compound of the present invention | 30 parts |
| Xylene | 33 parts |
| Dimethylform amid | 30 parts |
| Polyoxyethylene alkylallyl ether | 7 parts |

The foregoing is mixed and dissolved to obtain an emulsion including 30% of active ingredient.

The following test examples demonstrate that the cyclic amine compound or salt thereof according to the present invention is useful as an active ingredient of an acaricide.

Test Example 1

Efficacy Test Against *Tetranychus urticae*

Seventeen organic phosphorous-resistant adult female *Tetranychus urticae* mites were inoculated onto the first leaves of a kidney bean plant planted in a No. 3 pot 7 to 10 days after germination. Next, an emulsion was prepared having the formula indicated in the aforementioned Preparation example 2. This emulsion was diluted with water to a compound concentration of 125 ppm after which the diluted liquids were sprayed onto the kidney bean plant. The kidney bean plant was then placed in a temperature-controlled room at a temperature of 25° C. and humidity of 65%. The adult insect mortality rates were investigated 3 days after spraying. The test was repeated twice.

The aforementioned test was carried out on emulsions respectively containing the cyclic amine compounds of Compound No. H-1, H-2, H-5, H-29, H-41, H-42, H-43, H-51, H-52, H-54, H-55, H-56, H-57, H-58, H-59, H-60, H-61, H-62, H-63, H-64, H-65, H-66, H-67, H-68, H-70, H-71, H-72, H-73, H-74, H-75, H-79, H-80, H-82, H-83, H-84, H-85, H-86, H-87, H-89, H-90, K-8, K-12, K-38, and K-39. As a result, the insect mortality rates for all of the compounds in the case of diluting to a concentration of 125 ppm were 80% or higher.

In addition, the insect mortality rate for Compound No. H-81 in the case of diluting to a concentration of 31 ppm was also 80% or higher.

Test Example 2

Efficacy Test Against Panonychus citri

Ten acaricide-resistant adult female Panonychus citri mites were inoculated onto a mandarin orange leaf placed in a Petri dish. Next, an emulsion was prepared having the formula indicated in the aforementioned Preparation example 2. This emulsion was diluted with water to a compound concentration of 125 ppm after which the diluted liquids were sprayed onto the mandarin orange leaf with a rotary spraying tower. The mandarin orange leaf was then placed in a temperature-controlled room at a temperature of 25° C. and a humidity of 65%. The adult insect mortality rates were investigated 3 days after spraying.

The aforementioned test was carried out on emulsions respectively containing the cyclic amine compounds of Compound No. H-1, H-2, H-5, H-29, H-41, H-42, H-43, H-51, H-55, H-57, H-58, H-62, H-64, H-66, H-69, H-72, H-73, H-74, H-75, H-81, H-82, H-83, H-84, H-85, H-87, H-89, H-90, K-8, K-12, K-38 and K-39. As a result, the insect mortality rates for all of the compounds in the case of diluting to a concentration of 125 ppm were 80% or higher.

In addition, the insect mortality rates for Compound No. H-54, H-56, H-59, H-60, H-61, H-63, H-68, H-70, and H-80 in the case of diluting to a concentration of 31 ppm were also 80% or higher.

Test Example 3

Ovicidal Activity Test Against Egg of Tetranychus urticae

An adult female Tetranychus urticae mite was inoculated onto a leaf of a kidney bean plant placed in a Petri dish to allow the mite to lay eggs for 1 day. Next, an emulsion was prepared having the formula indicated in the aforementioned Preparation example 2. This emulsion was diluted with water to a compound concentration of 125 ppm after which the diluted liquid was sprayed onto the leaf of kidney bean plant with a rotary spraying tower. The leaf of kidney bean plant was then placed in a temperature-controlled room at a temperature of 25° C. and a humidity of 65%. The egg mortality rate was calculated by investigating whether or not the eggs that are sprayed with the emulsion eclosed.

The aforementioned test was carried out on the emulsions containing the cyclic amine compounds of Compound No.: H-1, H-2, H-29, H-43, H-54, H-56, and H-73. As a result, the egg mortality rates for all of the compounds in the case of diluting to a concentration of 125 ppm were 80% or higher.

Test Example 4

Ovicidal Activity Test Against Egg of Panonychus citri

An adult female Panonychus citri mite was inoculated onto a mandarin orange leaf placed in a Petri dish to allow the mite to lay eggs for 1 day. Next, an emulsion was prepared having the formula indicated in the aforementioned Preparation example 2. This emulsion was diluted with water to a compound concentration to 125 ppm after which the diluted liquid was sprayed onto the mandarin orange leaf with a rotary spraying tower. The mandarin orange leaf was then placed in a temperature-controlled room at a temperature of 25° C. and a humidity of 65%. The egg mortality rate was calculated by investigating whether or not the eggs sprayed with the emulsion eclosed.

The aforementioned test was carried out on the emulsions including the cyclic amine compounds of Compound No.: H-1, H-2, H-29, H-43, H-54, H-56, and H-73. As a result, the egg mortality rates in the case of diluting to a concentration of 125 ppm for all of the compounds were 80% or higher.

Test Example 5

Insecticidal Potency Test Against Haemaphysalis longicornis

A compound of the present invention was diluted with acetone to prepare a drug solution having a concentration of 400 ppm. 118 µL of the drug solution was coated on an inner surface of a 20-mL glass vial, followed by volatilizing acetone to form a thin film of the compound of the present invention on the inner surface of the glass vial. Since the area of the glass vial was 47 cm$^2$, the coating amount of the drug solution per inner surface area was 1 µg/cm$^2$. Eight larval Haemaphysalis longicornis ticks were placed in the glass vial, followed by closing the glass vial and placing it in a temperature-controlled room at 25° C. The insect mortality rate was calculated after 5 days.

Insect mortality rate (%)=(the number of dead ticks/ the number of released ticks)×100

As a result, among the compounds under test, the following compounds demonstrated 80% or higher insect mortality rate.

Compound No.: H-5, H29, H-43, H-55, H-63, H-73, H-83, H-90, J-42, K-38, K-39.

Test Example 6

Insecticidal Potency Test Against Cat Flea

A compound of the present invention was diluted with acetone to prepare a drug solution having a concentration of 400 ppm. 118 µL of the drug solution was coated on an inner surface of a 20-mL glass vial, followed by volatilizing acetone to form a thin film of the compound of the present invention on the inner surface of the glass vial. Since the area of the glass vial was 47 cm$^2$, the coating amount of the drug solution per inner surface area was 1 µg/cm$^2$. Eight larval Cat fleas were placed in the glass vial, followed by closing the glass vial and placing it in a temperature-controlled room at 25° C. The insect mortality rate was calculated after 1 day.

Insect mortality rate (%)=(the number of dead insects/the number of released insects)×100

As a result, among the compounds under test, the following compounds demonstrated 80% or higher insect mortality rate.

Compound No.: H-73, K-38, K-39.

In view of the foregoing results, it is apparent that the cyclic amine compound or salt thereof according to the present invention has a superior insecticidal potency against acaricides.

INDUSTRIAL APPLICABILITY

The cyclic amine compound or salt thereof according to the present invention makes it possible to effectively prevent the acaricides which are harmful to agricultural crops or harmful in terms of hygiene.

The hydroxylamine compound or salt thereof according to the present invention makes it possible to easily synthesis the cyclic amine compound or salt thereof according to the present invention. Therefore, the present invention is industrially useful.

The invention claimed is:

1. A cyclic amine compound represented by formula (I) or salt thereof:

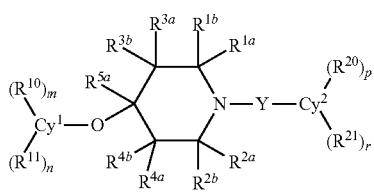

in formula (I),
- $Cy^1$ represents a phenyl group, a pyrazolyl group, a thiadiazolyl group, a pyridyl group, a pyrimidinyl group or a pyridazinyl group;
- $Cy^2$ represents a phenyl group, a pyrazolyl group, a thiadiazolyl group, a pyridyl group, a pyrimidinyl group, or a pyridazinyl group;
- $R^{1b}$, $R^{2b}$, $R^{3b}$, $R^{4b}$ and $R^{5a}$ independently represent a hydrogen atom or an unsubstituted or substituted C1-6 alkyl group;
- $R^{1a}$ and $R^{2a}$, or $R^{3a}$ and $R^{4a}$ bond together to form an unsubstituted or substituted C3 alkylene group, an unsubstituted or substituted C3 alkenylene group, or a group represented by formula: —CH$_2$C(=O)CH$_2$—;
- when $R^{1a}$ and $R^{2a}$ bond together, $R^{3a}$ and $R^{4a}$ independently represent a hydrogen atom or an unsubstituted or substituted C1-6 alkyl group;
- when $R^{3a}$ and $R^{4a}$ bond together, $R^{1a}$ and $R^{2a}$ independently represent a hydrogen atom or an unsubstituted or substituted C1-6 alkyl group;
- $R^{10}$ represents a C1-6 alkyl group, a C1-6 alkoxy C1-6 alkyl group, a C1-6 alkoxy C1-6 alkoxy C1-6 alkyl group, a C2-6 alkenyl group, a hydroxy group, a C1-6 alkoxy group, a C1-6 haloalkoxy group, a C3-8 cycloalkoxy group, a C2-6 alkenyloxy group, a C2-6 haloalkenyloxy group, a C2-6 alkynyloxy group, a C2-6 haloalkynyloxy group, a C1-6 alkoxy C1-6 alkoxy group, a C3-8 cycloalkyl C1-6 alkoxy group, a cyano C1-6 alkoxy group, a C1-7 acyl C1-6 alkoxy group, a hydroxy C1-6 alkoxy group, a C1-7 acyloxy group, a C1-6 alkoxycarbonyl group, a C2-6 alkenyloxycarbonyl group, a C2-6 alkynyloxycarbonyl group, a C1-6 alkoxycarbonyloxy group, a C1-6 alkyl aminocarbonyloxy group, a C6-10 aryl group, a heterocyclyl group, a C1-6 haloalkyl sulfonyloxy group, a C1-6 alkylidene aminooxy group, a C1-6 alkoxycarbonyl amino group, an unsubstituted or substituted C7-11 aralkyl group, an unsubstituted or substituted C7-11 aralkyloxy group, a C1-6 alkyl thio group or a nitro group;
- $R^{11}$ represents a cyano group, a halogen atom, a pentafluorosulfanyl group, a C1-6 haloalkyl group, a C2-6 haloalkenyl group or a C2-6 haloalkynyl group;
- $R^{20}$ represents a cyano group, a halogen atom, a pentafluorosulfanyl group, a C1-6 haloalkyl group, a C2-6 haloalkenyl group or a C2-6 haloalkynyl group; and
- $R^{21}$ represents a C1-6 alkyl group, a C1-6 alkoxy C1-6 alkyl group, a C1-6 alkoxy C1-6 alkoxy C1-6 alkyl group, a hydroxy group, a C1-6 alkoxy group, a C1-6 haloalkoxy group, a C2-6 haloalkenyloxy group, a C2-6 haloalkynyloxy group, a C1-6 alkoxy C1-6 alkoxy group, a C3-8 cycloalkyl C1-6 alkoxy group, a C1-6 alkoxycarbonyl group, a C2-6 alkenyloxycarbonyl group, a C2-6 alkynyloxycarbonyl group, a C1-6 alkylidene aminooxy group, a C1-6 alkoxycarbonyl amino group, an unsubstituted or substituted C7-11 aralkyl group, an unsubstituted or substituted C7-11 aralkyloxy group or a nitro group;
- m represents the number of $R^{10}$ and represents an integer of 0 to 5, when m is 2 or more, $R^{10}$s may be the same or different;
- n represents the number of $R^{11}$ and represents an integer of 0 to 5, when n is 2 or more, $R^{11}$s may be the same and different;
- p represents the number of $R^{20}$ and represents an integer of 0 to 5, when p is 2 or more, $R^{20}$s may be the same or different;
- r represents the number of $R^{21}$ and represents an integer of 0 to 5, when r is 2 or more, $R^{21}$s may be the same or different;
- Y represents an oxygen atom or a sulfur atom.

2. The cyclic amine compound or salt thereof according to claim 1, wherein
in formula (I), $Cy^1$ represents a phenyl group;
$R^{1b}$, $R^{2b}$, $R^{3a}$, $R^{3b}$, $R^{4a}$, $R^{4b}$ and $R^{5a}$ represent a hydrogen atom;
$R^{1a}$ and $R^{2a}$ bond together to form an unsubstituted or substituted C3-6 alkylene group, an unsubstituted or substituted C3-6 alkenylene group, a group represented by formula: —CH$_2$OCH$_2$—, a group represented by formula: —CH$_2$SCH$_2$—, a group represented by formula: —CH$_2$C(=O)CH$_2$— or a group represented by formula: —CH$_2$NR$^6$CH$_2$— (provided that $R^6$ represents a hydrogen atom, an unsubstituted or substituted C1-6 alkyl group, an unsubstituted or substituted C1-7 acyl group or an unsubstituted or substituted C1-6 alkoxycarbonyl group);
$Cy^2$ represents a pyridine-2-yl group;
Y represents an oxygen atom;
r represents 0; and
p represents an integer of 0 to 4.

3. A pest control agent comprising a liquid carrier and at least a compound selected from the cyclic amine compound or salt thereof according to claim 1 as an active ingredient.

* * * * *